(12) United States Patent
Robinson et al.

(10) Patent No.: US 11,363,956 B2
(45) Date of Patent: Jun. 21, 2022

(54) METHODS AND APPARATUSES FOR ASSESSMENT AND MANAGEMENT OF HEMODYNAMIC STATUS

(71) Applicant: Medici Technologies, LLC, Albuquerque, NM (US)

(72) Inventors: Mark Ries Robinson, Albuquerque, NM (US); Elena A Allen, Albuquerque, NM (US)

(73) Assignee: Medici Technologies LLC, Albuquerque, NM (US)

( * ) Notice: Subject to any disclaimer, the term of this patent is extended or adjusted under 35 U.S.C. 154(b) by 638 days.

(21) Appl. No.: 15/780,408

(22) PCT Filed: Dec. 6, 2016

(86) PCT No.: PCT/US2016/065140
§ 371 (c)(1),
(2) Date: May 31, 2018

(87) PCT Pub. No.: WO2017/100188
PCT Pub. Date: Jun. 15, 2017

(65) Prior Publication Data
US 2020/0288985 A1    Sep. 17, 2020

Related U.S. Application Data

(60) Provisional application No. 62/423,701, filed on Nov. 17, 2016, provisional application No. 62/375,431, (Continued)

(51) Int. Cl.
*A61B 5/0205* (2006.01)
*A61B 5/029* (2006.01)
(Continued)

(52) U.S. Cl.
CPC .......... *A61B 5/0205* (2013.01); *A61B 5/0024* (2013.01); *A61B 5/029* (2013.01);
(Continued)

(58) Field of Classification Search
CPC . A61B 5/0205; A61B 5/0024; A61B 5/02028; A61B 5/02405; A61B 5/029; A61B 5/091
(Continued)

(56) References Cited

U.S. PATENT DOCUMENTS

| 5,178,151 A | 1/1993 | Sackner |
| 5,778,879 A | 7/1998 | Ota |

(Continued)

OTHER PUBLICATIONS

Takehana et al "Effects of posture on heart rate and systolic time intervals in normal men"; The American Journal of Cardiology vol. 73, Issue 5, Feb. 15, 1994, pp. 411-414 (Year: 1994).*

(Continued)

*Primary Examiner* — Alex M Valvis
*Assistant Examiner* — Chanel J Jhin
(74) *Attorney, Agent, or Firm* — V Gerald Grafe

(57) ABSTRACT

Embodiments of the present invention provide reliable, convenient, and cost-effective methods and apparatuses to determine the hemodynamic status of the patent. The methods and apparatuses provide for the noninvasive determine of hemodynamic status by using systematic perturbations of venous return or trend observation over time. Embodiments do not require invasive pressure monitoring or the use of ventilator but instead can be an entirely noninvasive system.

11 Claims, 50 Drawing Sheets

Related U.S. Application Data filed on Aug. 15, 2016, provisional application No. 62/263,839, filed on Dec. 7, 2015.

(51) Int. Cl.

| | |
|---|---|
| *A61B 5/021* | (2006.01) |
| *A61B 5/091* | (2006.01) |
| *A61B 5/113* | (2006.01) |
| *A61B 5/024* | (2006.01) |
| *A61B 7/00* | (2006.01) |
| *A61B 5/00* | (2006.01) |
| *A61B 5/349* | (2021.01) |
| *A61B 5/11* | (2006.01) |
| *A61B 5/02* | (2006.01) |

(52) U.S. Cl.
CPC ...... *A61B 5/02125* (2013.01); *A61B 5/02416* (2013.01); *A61B 5/02427* (2013.01); *A61B 5/091* (2013.01); *A61B 5/113* (2013.01); *A61B 5/1126* (2013.01); *A61B 5/349* (2021.01); *A61B 7/00* (2013.01); *A61B 5/02028* (2013.01); *A61B 5/02405* (2013.01); *A61B 5/1116* (2013.01); *A61B 5/1118* (2013.01); *A61B 5/4561* (2013.01); *A61B 5/4812* (2013.01); *A61B 5/6826* (2013.01)

(58) Field of Classification Search
USPC .......................................................... 600/481
See application file for complete search history.

(56) References Cited

U.S. PATENT DOCUMENTS

| | | | | |
|---|---|---|---|---|
| 6,099,481 | A * | 8/2000 | Daniels ................. | A61B 5/083 128/204.23 |
| 6,893,402 | B2 | 5/2005 | Freund | |
| 7,616,110 | B2 | 11/2009 | Crump | |
| 7,742,808 | B2 | 6/2010 | Nissila | |
| 8,657,757 | B2 * | 2/2014 | Lazar ..................... | A61B 5/087 600/538 |
| 2002/0188205 | A1 | 12/2002 | Mills | |
| 2010/0049059 | A1 | 2/2010 | Ha | |
| 2011/0009764 | A1 * | 1/2011 | Lanier .................. | A61B 5/0836 600/532 |
| 2012/0053469 | A1 * | 3/2012 | Melker .................. | A61M 1/34 600/479 |
| 2014/0257050 | A1 | 9/2014 | Kuroda | |

OTHER PUBLICATIONS

Schumer et al "Diabetic autonomic neuropathy—part I: Autonomic nervous system data analysis by a computerized central unit in a multicenter trial"; The American Journal of Medicine vol. 85, Issue 5, Supplement 1, Nov. 28, 1988, pp. 137-143 (Year: 1988).*

Van Hoeyweghen, R.; Hanson, J.; Stewart, M. J.; Dethune, L.; Davies, I.; Little, R. A.; Horan, M. A.; Kirkman, E., Cardiovascular Response to Graded Lower Body Negative Pressure in Young and Elderly Man, 2001, Journal : Experimental Physiology.

Hassan, S.; Turner, P., Systolic time intervals: a review of the method in the non-invasive investigation of cardiac function in health, disease and clinical pharmacology., 1983, Journal : Postgraduate Medical Journal.

Harms, Mark P M; Wesseling, Karel H; Pott, Frank; Jenstrup, Morten; Goudoever, Jeroen Van; Secher, Niels H; Lieshout, Johannes J Van, Continuous stroke volume monitoring by modelling flow from non-invasive measurement of arterial pressure in humans under orthostatic stress, 1999, Journal : The Biochemical Society and the Medical Research Society.

Harley, Alexander; Starmer, C. Frank; Greenfield, Joseph C., Pressure-flow studies in man. An evaluation of the duration of the phases of systole, 1969, Journal : Journal of Clinical Investigation.

Günther, Sven; Sztrymf, Benjamin; Savale, Laurent; Lau, Edmund M.; Montani, David; Hervé, Philippe; Lador, Frédéric; Jaïs, Xavier; Parent, Florence; Simonneau, Gérald; Sitbon, Olivier; Humbert, Marc; Chemla, Denis, Relation between left ventricular ejection time and pulmonary hemodynamics in pulmonary hypertension, 2015, Journal : International Journal of Cardiology.

Grum, D. F.; Dauchot, P. J., Correlation of Systolic Time Intervals with Stroke Volume in Man, 1980, Book Section: Springer Berlin Heidelberg.

Gheorghiade, Mihai; Filippatos, Gerasimos; De Luca, Leonardo; Burnett, John, Congestion in Acute Heart Failure Syndromes: An Essential Target of Evaluation and Treatment, 2006, Journal : The American Journal of Medicine.

Boehmer, John P; Wariar, Ramesh; Zhang, Yi; Thompson, Julie A; Herro, Gerard; Sweeney, Robert J; Hatlestad, John; Thakur, Pramodsingh; Averina, Viktoria; An, Qi, Rationale and Design of the Multisensor Chronic Evaluations in Ambulatory Heart Failure Patients (MultiSENSE) Study, 2015, Journal : The Journal of Innovations in Cardiac Rhythm Management.

Early, Kirstin; Mankoff, Jennifer; Fienberg, Stephen E., Dynamic Question Ordering in Online Surveys, 2016, Journal : arXiv:1607.04209 [stat].

Braunschweig, F, Continous haemodynamic monitoring during withdrawal of diuretics in patients with congestive heart failure, 2002, Journal : European Heart Journal.

Bogert, L. W. J.; Wesseling, K. H.; Schraa, O.; Van Lieshout, E. J.; De Mol, B. A. J. M.; Van Goudoever, J.; Westerhof, B. E.; Van Lieshout, J. J., Pulse contour cardiac output derived from non-invasive arterial pressure in cardiovascular disease: Cardiac output derived from non-invasive arterial pressure, 2010, Journal : Anaesthesia.

Biering-Sørensen, Tor; Querejeta Roca, Gabriela; Hegde, Sheila M.; Shah, Amil M.; Claggett, Brian; Mosley, Thomas H.; Butler, Kenneth R.; Solomon, Scott D., Left ventricular ejection time is an independent predictor of incident heart failure in a community-based cohort: Systolic ejection time predicts heart failure, 2018, Journal : European Journal of Heart Failure.

Baker, Keith, Congestive Heart Failure, 2005, Journal : Harvard-MIT Division of Health Sciences and Technology.

Bain, R. J I; Tan, L B.; Murray, R G.; Davies, M. K; Littler, W. A, Central haemodynamic changes during lower body positive pressure in patients with congestive cardiac failure, 1989, Journal : Cardiovascular Research.

Chan, Gregory S H; Middleton, Paul M; Celler, Branko G; Wang, Lu; Lovell, Nigel H, Automatic detection of left ventricular ejection time from a finger photoplethysmographic pulse oximetry waveform: comparison with Doppler aortic measurement, 2007, Journal : Physiological Measurement.

Ameloot, Koen; Palmers, Pieter-Jan; Malbrain, Manu L.N.G., The accuracy of noninvasive cardiac output and pressure measurements with finger cuff: a concise review, 2015, Journal : Current Opinion in Critical Care.

Abraham, William T; Adamson, Philip B; Bourge, Robert C; Aaron, Mark F; Costanzo, Maria Rosa; Stevenson, Lynne W; Strickland, Warren; Neelagaru, Suresh; Ravel, Nirav; Krueger, Steven; Weiner, Stanislav; Shavelle, David; Jeffries, Bradley; Yadav, Jay S, Wireless pulmonary artery haemodynamic monitoring in chronic heart failure: a randomised controlled trial, 2011, Journal : The Lancet.

Sanchez Zambrano, Sergio; Spodick, David H., Comparative Responses to Orthostatic Stress in Normal and Abnormal Subjects, 1974, Journal : Chest.

Lewis, R P; Rittogers, S E; Froester, W F; Boudoulas, H, A critical review of the systolic time intervals., 1977, Journal : Circulation.

Weissler, Arnold M.; Harris, Willard S.; Schoenfeld, Clyde D., Systolic Time Intervals in Heart Failure in Man, 1968, Journal : Circulation.

Cziesler, Cody R, Using Least Variance for Robust Extraction of Systolic Time Intervals, 2014, Thesis: Rochester Institute of Technology.

Thomas, Michael; Shillingford, John, The Circulatory Response to a Standard Postural Change in ISCHiEMIC Heart Disease, 1965, Journal : British Heart Journal.

(56) References Cited

OTHER PUBLICATIONS

Tavel, Morton E.; Baugh, David O.; Feigenbaum, Harvey; Nasser, William K.; Stewart, Janie, Left Ventricular Ejection Time in Atrial Fibrillation, 1972, Journal : Circulation.

Stafford, R. W.; Harris, W. S.; Weissler, A. M., Left Ventricular Systolic Time Intervals as Indices of Postural Circulatory Stress in Man, 1970, Journal : Circulation.

Shi, X.; Crandall, C. G.; Raven, P. B., Hemodynamic responses to graded lower body positive pressure, 1993, Journal : American Journal of Physiology-Heart and Circulatory Physiology.

Quarry-Pigott, Veronica; Chirife, Raul; Spodick, David H., Ejection Time by Ear Densitogram and Its Derivative: Clinical and Physiologic Applications, 1973, Journal : Circulation.

Pellicori, Pierpaolo; Department of Cardiology, Castle Hill Hospital, Hull York Medical School (at University of Hull), Kingston upon Hull, UK; Kaur, Kuldeep; Department of Cardiology, Castle Hill Hospital, Hull York Medical School (at University of Hull), Kingston upon Hull, UK; Clark, Andrew L; Department of Cardiology, Castle Hill Hospital, Hull York Medical School (at University of Hull), Kingston upon Hull, UK, Fluid Management in Patients With Chronic Heart Failure, 2015, Journal : Cardiac Failure Review.

Patel, Ayan R.; Alsheikh-Ali, Alawi A.; Mukherjee, Jayanta; Evangelista, Antonietta; Quraini, Dima; Ordway, Linda J.; Kuvin, Jeffrey T.; DeNofrio, David; Pandian, Natesa G., 3D Echocardiography to Evaluate Right Atrial Pressure in Acutely Decompensated Heart Failure, 2011, Journal : JACC: Cardiovascular Imaging.

Nohria, Anju; Tsang, Sui W; Fang, James C; Lewis, Eldrin F; Jarcho, John A; Mudge, Gilbert H; Stevenson, Lynne W, Clinical assessment identifies hemodynamic profiles that predict outcomes in patients admitted with heart failure, 2003, Journal : Journal of the American College of Cardiology.

Boehmer, John P.; Hariharan, Ramesh; Devecchi, Fausto G.; Smith, Andrew L.; Molon, Giulio; Capucci, Alessandro; An, Qi; Averina, Viktoria; Stolen, Craig M.; Thakur, Pramodsingh H.; Thompson, Julie A.; Wariar, Ramesh; Zhang, Yi; Singh, Jagmeet P., A Multisensor Algorithm Predicts Heart Failure Events in Patients With Implanted Devices, 2017, Journal : JACC: Heart Failure.

Kimura, B. J.; Dalugdugan, R.; Gilcrease, G. W.; Phan, J. N.; Showalter, B. K.; Wolfson, T., The effect of breathing manner on inferior vena caval diameter, 2011, Journal : European Journal of Echocardiography.

Jansen, J.R.C.; Schreuder, J.J.; Mulier, J.P.; Smith, N.T.; Settels, J.J.; Wesseling, K.H., A comparison of cardiac output derived from the arterial pressure wave against thermodilution in cardiac surgery patients †, 2001, Journal : British Journal of Anaesthesia.

Abay, T. Y.; Kyriacou, P. A., Accuracy of reflectance photoplethysmography on detecting cuff-induced vascular occlusions, 2015, Conference: IEEE.

Addison, Paul S.; Wang, Rui; Uribe, Alberto A.; Bergese, Sergio D., Increasing signal processing sophistication in the calculation of the respiratory modulation of the photoplethysmogram (DPOP), 2015, Journal : Journal of Clinical Monitoring and Computing.

Alastruey, Jordi; Passerini, Tiziano; Formaggia, Luca; Peiró, Joaquim, Physical determining factors of the arterial pulse waveform: theoretical analysis and calculation using the 1-D formulation, 2012, Journal : Journal of Engineering Mathematics.

Alastruey, Jordi; Parker, Kim H; Sherwin, Spencer J, Arterial pulse wave haemodynamics, 2012, Conference:.

Allen, J; Murray, A, Age-related changes in peripheral pulse timing characteristics at the ears, fingers and toes, 2002, Journal : Journal of Human Hypertension.

Amoore, J. N; Santamore, W. P, Venous collapse and the respiratory variability in systemic venous return, 1994, Journal : Cardiovascular Research.

He, David Da; Winokur, Eric S.; Sodini, Charles G., An Ear-Worn Vital Signs Monitor, 2015, Journal : IEEE Transactions on Biomedical Engineering.

Gheorghiade, Mihai; Follath, Ferenc; Ponikowski, Piotr; Barsuk, Jeffrey H.; Blair, John E.A.; Cleland, John G.; Dickstein, Kenneth; Drazner, Mark H.; Fonarow, Gregg C.; Jaarsma, Tiny; Jondeau, Guillaume; Sendon, Jose Lopez; Mebazaa, Alexander; Metra, Marco; Nieminen, Markku; Pang, Peter S.; Seferovic, Petar; Stevenson, Lynne W.; van Veldhuisen, Dirk J.; Zannad, Faiez; Anker, Stefan D.; Rhodes, Andrew; McMurray, John J.V.; Filippatos, Gerasimos, Assessing and grading congestion in acute heart failure: a scientific statement from the Acute Heart Failure Committee of the Heart Failure Association of the European Society of Cardiology and endorsed by the European Society of Intensive Care Medicine, 2010, Journal : European Journal of Heart Failure.

Mandarino, William A; Pinsky, Michael R; Iii, John Gorcsan, Assessment of Left Ventricular Contractile State by Preload-Adjusted Maximal Power Using Echocardiographic Automated Border Detection 1, 1998, Journal : JACC.

Couceiro, Ricardo; Carvalho, P; Paiva, R P; Henriques, J; Quintal, I; Antunes, M; Muehlsteff, J; Eickholt, C; Brinkmeyer, C; Kelm, M; Meyer, C, Assessment of cardiovascular function from multi-Gaussian fitting of a finger photoplethysmogram, 2015, Journal : Physiological Measurement.

Awad, Aymen A.; Stout, Robert G.; Ghobashy, M. Ashraf M.; Rezkanna, Hoda A.; Silverman, David G.; Shelley, Kirk H., Analysis of the Ear Pulse Oximeter Waveform, 2006, Journal : Journal of Clinical Monitoring and Computing.

Barnas, Michel G W; Boer, Walther H; Koomans, Hein A, Hemodynamic Patterns and Spectral Analysis of Heart Rate Variability during Dialysis Hypotension, 1999, Journal : J Am Soc Nephrol.

Baruch, Martin C; Warburton, Darren ER; Bredin, Shannon SD; Cote, Anita; Gerdt, David W; Adkins, Charles M, Pulse Decomposition Analysis of the digital arterial pulse during hemorrhage simulation, 2011, Journal : Nonlinear Biomedical Physics.

Baruch, Martin C; Kalantari, Kambiz; Gerdt, David W; Adkins, Charles M, Validation of the pulse decomposition analysis algorithm using central arterial blood pressure, 2014, Journal : BioMedical Engineering OnLine.

Ashouri, Nazar; Orlandic, Lara; Inan, Omer, Unobtrusive Estimation of Cardiac Contractility and Stroke Volume Changes Using Ballistocardiogram Measurements on a High Bandwidth Force Plate, 2016, Journal : Sensors.

Zema, M J; Restivo, B; Sos, T; Sniderman, K W; Kline, S, Left ventricular dysfunction—bedside Valsalva manoeuvre., 1980, Journal : Heart.

Bendjelid, Karim, The pulse oximetry plethysmographic curve revisited:, 2008, Journal : Current Opinion in Critical Care.

Bendjelid, Karim; Suter, Peter M.; Romand, Jacques A., The respiratory change in preejection period: a new method to predict fluid responsiveness, 2004, Journal : Journal of Applied Physiology.

Bighamian, Ramin; Hahn, Jin-Oh, Relationship between Stroke Volume And Pulse Pressure during Blood Volume Perturbation: A Mathematical Analysis, 2014, Journal : BioMed Research International.

Bodson, Laurent; Vieillard-Baron, Antoine, Respiratory variation in inferior vena cava diameter: surrogate of central venous pressure or parameter of fluid responsiveness? Let the physiology reply, 2012, Journal : Critical Care.

Bogert, Lysander W. J.; van Lieshout, Johannes J., Non-invasive pulsatile arterial pressure and stroke volume changes from the human finger: noninvasive pressure and flow, 2005, Journal : Experimental Physiology.

Borlaug, Barry A.; Kass, David A., Ventricular—Vascular Interaction in Heart Failure, 2008, Journal : Heart Failure Clinics.

Bornstein, Abraham; Gaasch, William H.; Harrington, John, Assessment of the cardiac effects of hemodialysis with systolic time intervals and echocardiography, 1983, Journal : The American Journal of Cardiology.

Smith, D; Craige, E, Mechanism of the dicrotic pulse., 1986, Journal : Heart.

Bradley, T. Douglas; Holloway, Richard M.; McLaughlin, Peter R.; Ross, Bette L.; Walters, Janice; Liu, Peter P., Cardiac Output Response to Continuous Positive Airway Pressure in Congestive Heart Failure, 1992, Journal : American Review of Respiratory Disease.

(56) References Cited

OTHER PUBLICATIONS

Broccard, Alain F., Cardiopulmonary interactions and volume status assessment, 2012, Journal : Journal of Clinical Monitoring and Computing.

Bronzwaer, Anne-Sophie G. T.; Ouweneel, Dagmar M.; Stok, Wim J.; Westerhof, Berend E.; van Lieshout, Johannes J., Arterial Pressure Variation as a Biomarker of Preload Dependency in Spontaneously Breathing Subjects—A Proof of Principle, 2015, Journal : PLOS ONE.

Nieminen, T.; Koobi, T.; Turjanmaa, V., Can stroke volume and cardiac output be determined reliably in a tilt-table test using the pulse contour method?, 2000, Journal : Clinical Physiology.

Cannesson, Maxime; Attof, Yassin; Rosamel, Pascal; Desebbe, Olivier; Joseph, Pierre; Metton, Olivier; Bastien, Olivier; Lehot, Jean-Jacques, Respiratory Variations in Pulse Oximetry Plethysmographic Waveform Amplitude to Predict Fluid Responsiveness in the Operating Room:, 2007, Journal : Anesthesiology.

Cannesson, Maxime; Delannoy, Bertrand; Morand, Antoine; Rosamel, Pascal; Attof, Yassin; Bastien, Olivier; Lehot, Jean-Jacques, Does the Pleth Variability Index Indicate the Respiratory-Induced Variation in the Plethysmogram and Arterial Pressure Waveforms?:, 2008, Journal : Anesthesia & Analgesia.

Cannesson, Maxime; Aboy, Mateo; Hofer, Christoph K; Rehman, Mohamed, Pulse pressure variation: where are we today?, 2011, Journal : Journal of Clinical Monitoring and Computing.

De Wilde, R. B. P.; Schreuder, J. J.; van den Berg, P. C. M.; Jansen, J. R. C., An evaluation of cardiac output by five arterial pulse contour techniques during cardiac surgery, 2007, Journal : Anaesthesia.

Costanzo, Maria R.; Stevenson, Lynne W.; Adamson, Philip B.; Desai, Akshay S.; Heywood, J. Thomas; Bourge, Robert C.; Bauman, Jordan; Abraham, William T., Interventions Linked to Decreased Heart Failure Hospitalizations During Ambulatory Pulmonary Artery Pressure Monitoring, 2016, Journal : JACC: Heart Failure.

Cavallaro, Fabio; Sandroni, Claudio; Marano, Cristina; La Torre, Giuseppe; Mannocci, Alice; De Waure, Chiara; Bello, Giuseppe; Maviglia, Riccardo; Antonelli, Massimo, Diagnostic accuracy of passive leg raising for prediction of fluid responsiveness in adults: systematic review and meta-analysis of clinical studies, 2010, Journal : Intensive Care Medicine.

Chan, Gregory S. H.; Middleton, Paul M.; Celler, Branko G.; Wang, Lu; Lovell, Nigel H., Change in pulse transit time and pre-ejection period during head-up tilt-induced progressive central hypovolaemia, 2007, Journal : Journal of Clinical Monitoring and Computing.

Middleton, Paul M.; Chan, Gregory S.H.; O'Lone, Emma; Steel, Elizabeth; Carroll, Rebecca; Celler, Branko G.; Lovell, Nigel H., Changes in left ventricular ejection time and pulse transit time derived from finger photoplethysmogram and electrocardiogram during moderate haemorrhage, 2009, Journal : Clinical Physiology and Functional Imaging.

Chantler, Paul D.; Lakatta, Edward G., Arterial—Ventricular Coupling with Aging and Disease, 2012, Journal : Frontiers in Physiology.

Cheifetz, I. M., Cardiorespiratory Interactions: The Relationship Between Mechanical Ventilation and Hemodynamics, 2014, Journal : Respiratory Care.

Martin, C. Edwin; Shaver, James A.; Thompson, Mark E.; Reddy, P. Sudhakar; Leonard, James J., Direct Correlation of External Systolic Time Intervals with Internal Indices of Left Ventricular Function in Man, 1971, Journal : Circulation.

Sochowski, Randall A.; Dubbin, James D.; Naqvi, Salim Z., Clinical and hemodynamic assessment of the hepatojugular reflux, 1990, Journal : The American Journal of Cardiology.

Su, Ho-Ming; Lin, Tsung-Hsien; Hsu, Po-Chao; Chu, Chun-Yuan; Lee, Wen-Hsien; Chen, Szu-Chia; Lee, Chee-Siong; Voon, Wen-Chol; Lai, Wen-Ter; Sheu, Sheng-Hsiung, A Comparison between Brachial and Echocardiographic Systolic Time Intervals, 2013, Journal : PLoS ONE.

Convertino, Victor A.; Ratliff, Duane A.; Ryan, Kathy L.; Doerr, Donald F.; Ludwig, David A.; Muniz, Gary W.; Britton, Deanna L.; Clah, Savran D.; Fernald, Kathleen B.; Ruiz, Alicia F.; Lurie, Keith G.; Idris, Ahamed H., Hemodynamics associated with breathing through an inspiratory impedance threshold device in human volunteers:, 2004, Journal : Critical Care Medicine.

Convertino, Victor A.; Moulton, Steven L.; Grudic, Gregory Z.; Rickards, Caroline A.; Hinojosa-Laborde, Carmen; Gerhardt, Robert T.; Blackbourne, Lorne H.; Ryan, Kathy L., Use of Advanced Machine-Learning Techniques for Noninvasive Monitoring of Hemorrhage:, 2011, Journal : The Journal of Trauma: Injury, Infection, and Critical Care.

Convertino, Victor A.; Grudic, Greg; Mulligan, Jane; Moulton, Steve, Estimation of individual-specific progression to impending cardiovascular instability using arterial waveforms, 2013, Journal : Journal of Applied Physiology.

Convertino, Victor A.; Wirt, Michael D.; Glenn, John F.; Lein, Brian C., The Compensatory Reserve for Early and Accurate Prediction of Hemodynamic Compromise: A Review of the Underlying Physiology, 2016, Journal : SHOCK.

Coudray, Alice; Romand, Jacques-André; Treggiari, Miriam; Bendjelid, Karim, Fluid responsiveness in spontaneously breathing patients: A review of indexes used in intensive care:, 2005, Journal : Critical Care Medicine.

Dahl, Michael K; Vistisen, Simon T; Koefoed-Nielsen, Jacob; Larsson, Anders, Using an expiratory resistor, arterial pulse pressure variations predict fluid responsiveness during spontaneous breathing: an experimental porcine study, 2009, Journal : Critical Care.

Desebbe, Olivier; Cannesson, Maxime, Using ventilation-induced plethysmographic variations to optimize patient fluid status:, 2008, Journal : Current Opinion in Anaesthesiology.

Hoeksel, S. A. A. P., et al; J.A. Blom, PhD,3 and J.J. Schreuder,MD, PhD1, Detection of Dicrotic Notch in Arterial Pressure Signals, 1997, Journal : Journal of Clinical Monitoring.

Dong, Zhou-zhou, Passive leg raising as an indicator of fluid responsiveness in patients with severe sepsis, 2012, Journal : World Journal of Emergency Medicine.

Nandi, Priya S.; Pigott, Veronica M.; Spodick, David H., Sequential Cardiac Responses during the Respiratory Cycle: Patterns of Change in Systolic Intervals, 1973, Journal : Chest.

Martinez-Alajarin, Juan; Ruiz-Merino, Ramon, Efficient method for events detection in phonocardiographic signals, 2005, Conference:.

Eichhorn, V.; Trepte, C.; Richter, H.P.; Kubitz, J.C.; Goepfert, M.S.; Goetz, A.E.; Reuter, D.A., Respiratory systolic variation test in acutely impaired cardiac function for predicting volume responsiveness in pigs, 2011, Journal : British Journal of Anaesthesia.

Carvalho, P; Paiva, R P; Couceiro, R; Henriques, J; Antunes, M; Quintal, I; Muehlsteff, J; Aubert, X, Comparison of systolic time interval measurement modalities for portable devices, 2010, Conference: IEEE.

Jellema, Wilbert T.; Imholz, Ben P. M.; Oosting, Hans; Wesseling, Karel H.; van Lieshout, Johannes J., Estimation of beat-to-beat changes in stroke volume from arterial pressure: A comparison of two pressure wave analysis techniques during head-up tilt testing in young, healthy men, 1999, Journal : Clinical Autonomic Research.

Felker, G. Michael; Cuculich, Phillip S.; Gheorghiade, Mihai, The Valsalva Maneuver: A Bedside "Biomarker" for Heart Failure, 2006, Journal : The American Journal of Medicine.

Carsetti, Andrea; Cecconi, Maurizio; Rhodes, Andrew, Fluid bolus therapy: monitoring and predicting fluid responsiveness, 2015, Journal : Current Opinion in Critical Care.

Foo, Jong Y. A.; Lim, Chu S.; Wilson, Stephen J., Photoplethysmographic Assessment of Hemodynamic Variations Using Pulsatile Tissue Blood Volume, 2009, Journal : Angiology.

Javed, Faizan; Middleton, Paul M; Malouf, Philip; Chan, Gregory S H; Savkin, Andrey V; Lovell, Nigel H; Steel, Elizabeth; Mackie, James, Frequency spectrum analysis of finger photoplethysmographic waveform variability during haemodialysis, 2010, Journal : Physiological Measurement.

García, Manuel Ignacio Monge; Romero, Manuel Gracia; Cano, Anselmo Gil; Aya, Hollmann D; Rhodes, Andrew; Grounds, Robert Michael; Cecconi, Maurizio, Dynamic arterial elastance as a predictor of arterial pressure response to fluid administration: a validation study, 2014, Journal : Critical Care.

(56) References Cited

OTHER PUBLICATIONS

Geerts, Bart; de Wilde, Rob; Aarts, Leon; Jansen, Jos, Pulse Contour Analysis to Assess Hemodynamic Response to Passive Leg Raising, 2011, Journal : Journal of Cardiothoracic and Vascular Anesthesia.

Gomez, Hernando; Pinsky, Michael R, Ventilation on Heart—Lung Interactions, 2012, Book: McGraw Hill.

Electrophysiology, Task Force of the European Society of Cardiology the North American Society of Pacing, Heart rate variability: standards of measurement, physiological interpretation, and clinical use., 1996, Journal : Eur Heart J.

Guinot, P.-G.; de Broca, B.; Abou Arab, O.; Diouf, M.; Badoux, L.; Bernard, E.; Lorne, E.; Dupont, H., Ability of stroke volume variation measured by oesophageal Doppler monitoring to predict fluid responsiveness during surgery, 2013, Journal : British Journal of Anaesthesia.

Guinot, P.-G.; Godart, J.; de Broca, B.; Bernard, E.; Lorne, E.; Dupont, H., End-expiratory occlusion manoeuvre does not accurately predict fluid responsiveness in the operating theatre, 2014, Journal : British Journal of Anaesthesia.

Heenen, Sarah; Backer, Daniel De; Vincent, Jean-Louis, How can the response to volume expansion in patients with spontaneous respiratory movements be predicted?, 2006, Journal : Critical Care.

Préau, Sébastien; Dewavrin, Florent; Soland, Vincent; Bortolotti, Perrine; Coiling, Delphine; Chagnon, Jean-luc; Durocher, Alain; Saulnier, Fabienne, Hemodynamic Changes during a Deep Inspiration Maneuver Predict Fluid Responsiveness in Spontaneously Breathing Patients, 2012, Journal : Cardiology Research and Practice.

Hickey, Michelle; Phillips, Justin P.; Kyriacou, Panayiotis, Venous pooling and drainage affects photoplethysmographic signals at different vertical hand positions, 2015, Conference: SPIE BiOS.

Hinojosa-Laborde, Carmen; Rickards, Caroline A.; Ryan, Kathy L.; Convertino, Victor A., Heart Rate Variability during Simulated Hemorrhage with Lower Body Negative Pressure in High and Low Tolerant Subjects, 2011, Journal : Frontiers in Physiology.

Bui, Anh L.; Fonarow, Gregg C., Home Monitoring for Heart Failure Management, 2012, Journal : Journal of the American College of Cardiology.

Hong, D. M.; Lee, J. M.; Seo, J. H.; Min, J. J.; Jeon, Y.; Bahk, J. H., Pulse pressure variation to predict fluid responsiveness in spontaneously breathing patients: tidal vs forced inspiratory breathing, 2014, Journal : Anaesthesia.

Adamson, Philip B.; Smith, Andrew L.; Abraham, William T.; Kleckner, Karen J.; Stadler, Robert W.; Shih, Alex; Rhodes, Melissa M., Continuous Autonomic Assessment in Patients With Symptomatic Heart Failure: Prognostic Value of Heart Rate Variability Measured by an Implanted Cardiac Resynchronization Device, 2004, Journal : Circulation.

Cokkinos, D V; Heimonas, E T; Demopoulos, J N; Harralambakis, A; Tsartsalis, G; Gardikas, C D, Influence of heart rate increase on uncorrected pre-ejection period/left ventricular ejection time (PEP/LVET) ratio in normal individuals., 1976, Journal : Heart.

Mertens, H. M.; Mannebach, H.; Trieb, G.; Gleichmann, U., Influence of heart rate on systolic time intervals: Effects of atrial pacing versus dynamic exercise, 1981, Journal : Clinical Cardiology.

Jardin, François, Ventricular interdependence: how does it impact on hemodynamic evaluation in clinical practice?, 2003, Journal : Intensive Care Medicine.

Jellema, Wilbert Tjebbe, Cardiovascular dynamics in hypovolemic and septic shock, 2005, Thesis: s.n.].

Judson, Walter E.; Hatcher, J. D.; Wilkins, Robert W., Blood Pressure Responses to the Valsalva Maneuver in Cardiac Patients with and without Congestive Failure, 1955, Journal : Circulation.

Karpetas, A.; Sarafidis, P. A.; Georgianos, P. I.; Protogerou, A.; Vakianis, P.; Koutroumpas, G.; Raptis, V.; Stamatiadis, D. N.; Syrganis, C.; Liakopoulos, V.; Efstratiadis, G.; Lasaridis, A. N., Ambulatory Recording of Wave Reflections and Arterial Stiffness during Intra- and Interdialytic Periods in Patients Treated with Dialysis, 2015, Journal : Clinical Journal of the American Society of Nephrology.

Kavouras, Stavros A., Assessing hydration status:, 2002, Journal : Current Opinion in Clinical Nutrition and Metabolic Care.

Korner, P. I.; Tonkin, A. M.; Uther, J. B., Reflex and mechanical circulatory effects of graded Valsalva maneuvers in normal man, 1976, Journal : Journal of Applied Physiology.

Koutroumbas, Georgios; Georgianos, Panagiotis I.; Sarafidis, Pantelis A.; Protogerou, Athanase; Karpetas, Antonios; Vakianis, Pantelis; Raptis, Vassilios; Liakopoulos, Vassilios; Panagoutsos, Stylianos; Syrganis, Christos; Passadakis, Ploumis, Ambulatory aortic blood pressure, wave reflections and pulse wave velocity are elevated during the third in comparison to the second interdialytic day of the long interval in chronic haemodialysis patients, 2015, Journal : Nephrology Dialysis Transplantation.

Kuntamalla, Srinivas; Ram Gopal Reddy, L., An Efficient and Automatic Systolic Peak Detection Algorithm for Photoplethysmographic Signals, 2014, Journal : International Journal of Computer Applications.

Lamia, Bouchra; Chemla, Denis; Richard, Christian; Teboul, Jean-Louis, Clinical review: Interpretation of arterial pressure wave in shock states, 2005, Journal : BioMed Central Ltd.

Lamia, Bouchra; Ochagavia, Ana; Monnet, Xavier; Chemla, Denis; Richard, Christian; Teboul, Jean-Louis, Echocardiographic prediction of volume responsiveness in critically ill patients with spontaneously breathing activity, 2007, Journal : Intensive Care Medicine.

Langewouters, G.J.; Wesseling, K.H.; Goedhard, W.J.A., The static elastic properties of 45 human thoracic and 20 abdominal aortas in vitro and the parameters of a new model, 1984, Journal : Journal of Biomechanics.

Lansdorp, B.; Lemson, J.; van Putten, M.J.A.M.; de Keijzer, A.; van der Hoeven, J.G.; Pickkers, P., Dynamic indices do not predict volume responsiveness in routine clinical practice, 2012, Journal : British Journal of Anaesthesia.

Lanspa, Michael J.; Grissom, Colin K.; Hirshberg, Eliotte L.; Jones, Jason P.; Brown, Samuel M., Applying Dynamic Parameters to Predict Hemodynamic Response to Volume Expansion in Spontaneously Breathing Patients With Septic Shock:, 2013, Journal : Shock.

Laurent, Stephane; Cockcroft, John; Van Bortel, Luc; Boutouyrie, Pierre; Giannattasio, Cristina; Hayoz, Daniel; Pannier, Bruno; Vlachopoulos, Charalambos; Wilkinson, Ian; Struijker-Boudier, Harry, Abridged version of the expert consensus document on arterial stiffness, 2007, Journal : Artery Research.

Lee, Qim Y; Redmond, Stephen J; Chan, Gregory SH; Middleton, Paul M; Steel, Elizabeth; Malouf, Philip; Critoph, Cristopher; Flynn, Gordon; O'Lone, Emma; Lovell, Nigel H, Estimation of cardiac output and systemic vascular resistance using a multivariate regression model with features selected from the finger photoplethysmogram and routine cardiovascular measurements, 2013, Journal : BioMedical Engineering OnLine.

Levick, J. R., An introduction to cardiovascular physiology, 1991, Book: Butterworths.

Levine, B D; Lane, L D; Buckey, J C; Friedman, D B; Blomqvist, C G, Left ventricular pressure-volume and Frank-Starling relations in endurance athletes. Implications for orthostatic tolerance and exercise performance., 1991, Journal : Circulation.

Yinbo Liu; Poon, C.C.Y.; Yuan-Ting Zhang; Yip, G.W.K.; Cheuk-Man Yu, A novel method for assessing arterial stiffness by a hydrostatic approach, 2009, Conference: IEEE.

Luecke, Thomas; Pelosi, Paolo, Clinical review: Positive end-expiratory pressure and cardiac output, 2005, Journal : BioMed Central Ltd.

Magder, Sheldon, Bench-to-bedside review: An approach to hemodynamic monitoring—Guyton at the bedside, 2012, Journal : Critical Care.

Magder, Sheldon, Flow-directed vs. goal-directed strategy for management of hemodynamics:, 2016, Journal : Current Opinion in Critical Care.

Magder, S, From PV loop to Starling curve, 0, Presentation:.

Maizel, Julien; Airapetian, Norair; Lorne, Emmanuel; Tribouilloy, Christophe; Massy, Ziad; Slama, Michel, Diagnosis of central hypovolemia by using passive leg raising, 2007, Journal : Intensive Care Medicine.

(56) References Cited

OTHER PUBLICATIONS

Marik, Paul E., Techniques for Assessment of Intravascular Volume in Critically Ill Patients, 2009, Journal : Journal of Intensive Care Medicine.

Marik, Paul E.; Cavallazzi, Rodrigo; Vasu, Tajender; Hirani, Amyn, Dynamic changes in arterial waveform derived variables and fluid responsiveness in mechanically ventilated patients: A systematic review of the literature*:, 2009, Journal : Critical Care Medicine.

Marik, P.E.; Lemson, J., Fluid responsiveness: an evolution of our understanding, 2014, Journal : British Journal of Anaesthesia.

Marik, Paul E; Monnet, Xavier; Teboul, Jean-Louis, Hemodynamic parameters to guide fluid therapy, 2011, Journal : Annals of Intensive Care.

McGrath, Susan P.; Ryan, Kathy L.; Wendelken, Suzanne M.; Rickards, Caroline A.; Convertino, Victor A., Pulse Oximeter Plethysmographic Waveform Changes in Awake, Spontaneously Breathing, Hypovolemic Volunteers:, 2011, Journal : Anesthesia & Analgesia.

Albert, N. M., Fluid Management Strategies in Heart Failure, 2012, Journal : Critical Care Nurse.

Middleton, Paul M.; Chan, Gregory S. H.; O'Lone, Emma; Steel, Elizabeth; Carroll, Rebecca; Celler, Branko G.; Lovell, Nigel H., Spectral Analysis of Finger Photoplethysmographic Waveform Variability in a Model of Mild to Moderate Haemorrhage, 2008, Journal : Journal of Clinical Monitoring and Computing.

Millasseau, Sandrine C; Ritter, James M; Takazawa, Kenji; Chowienczyk, Philip J, Contour analysis of the photoplethysmographic pulse measured at the finger:, 2006, Journal : Journal of Hypertension.

Monge Garcia, Manuel Ignacio; Gil Cano, Anselmo; Gracia Romero, Manuel, Dynamic arterial elastance to predict arterial pressure response to volume loading in preload-dependent patients, 2011, Journal : Critical Care.

Monnet, Xavier; Rienzo, Mario; Osman, David; Anguel, Nadia; Richard, Christian; Pinsky, Michael R.; Teboul, Jean-Louis, Passive leg raising predicts fluid responsiveness in the critically ill*:, 2006, Journal : Critical Care Medicine.

Monnet, Xavier; Osman, David; Ridel, Christophe; Lamia, Bouchra; Richard, Christian; Teboul, Jean-Louis, Predicting volume responsiveness by using the end-expiratory occlusion in mechanically ventilated intensive care unit patients:, 2009, Journal : Critical Care Medicine.

Monnet, Xavier; Lamia, Bouchra; Teboul, Jean-Louis, Pulse oximeter as a sensor of fluid responsiveness: do we have our finger on the best solution?, 2005, Journal : Critical Care.

Monnet, Xavier; Pinsky, Michael R., Predicting the determinants of volume responsiveness, 2015, Journal : Intensive Care Medicine.

Monnet, Xavier; Teboul, Jean-Louis, Passive leg raising: five rules, not a drop of fluid!, 2015, Journal : Critical Care.

Moulton, Steven L.; Mulligan, Jane; Grudic, Greg Z.; Convertino, Victor A., Running on empty? The compensatory reserve index:, 2013, Journal : Journal of Trauma and Acute Care Surgery.

Muller, Laurent; Bobbia, Xavier; Toumi, Mehdi; Louart, Guillaume; Molinari, Nicolas; Ragonnet, Benoit; Quintard, Hervé; Leone, Marc; Zoric, Lana; Lefrant, Jean; the AzuRea group, Respiratory variations of inferior vena cava diameter to predict fluid responsiveness in spontaneously breathing patients with acute circulatory failure: need for a cautious use, 2012, Journal : Critical Care.

Najafi, B.; Aminian, K.; Paraschiv-Ionescu, A.; Loew, F.; Bula, C.J.; Robert, P., Ambulatory system for human motion analysis using a kinematic sensor: monitoring of daily physical activity in the elderly, 2003, Journal : IEEE Transactions on Biomedical Engineering.

Natalini, Giuseppe; Rosano, Antonio; Taranto, Maria; Faggian, Barbara; Vittorielli, Elena; Bernardini, Achille, Arterial Versus Plethysmographic Dynamic Indices to Test Responsiveness for Testing Fluid Administration in Hypotensive Patients: A Clinical Trial:, 2006, Journal : Anesthesia & Analgesia.

Saugel, B.; Cecconi, M.; Wagner, J.Y.; Reuter, D.A., Noninvasive continuous cardiac output monitoring in perioperative and intensive care medicine, 2015, Journal : British Journal of Anaesthesia.

Ahlström, Christer, Nonlinear phonocardiographic signal processing, 2008, Thesis: Department of Biomedical Engineering, Linköping University.

Zaidi, S N; Collins, S M, Orthostatic stress and area under the curve of photoplethysmography waveform, 2016, Journal : Biomedical Physics & Engineering Express.

Perel, Azriel; Minkovich, Leonid; Preisman, Sergey; Abiad, Michel; Segal, Eran; Coriat, Pierre, Assessing Fluid-Responsiveness by a Standardized Ventilatory Maneuver: The Respiratory Systolic Variation Test:, 2005, Journal : Anesthesia & Analgesia.

Perel, Azriel; Pizov, Reuven; Cotev, Shamay, Respiratory variations in the arterial pressure during mechanical ventilation reflect volume status and fluid responsiveness, 2014, Journal : Intensive Care Medicine.

Philip-Joët, Francois F.; Paganelli, Franck F.; Dutau, Hervé L.; Saadjian, Alain Y., Hemodynamic Effects of Bilevel Nasal Positive Airway Pressure Ventilation in Patients with Heart Failure, 1999, Journal : Respiration.

Meredith, D. J.; Clifton, D.; Charlton, P.; Brooks, J.; Pugh, C. W.; Tarassenko, L., Photoplethysmographic derivation of respiratory rate: a review of relevant physiology, 2012, Journal : Journal of Medical Engineering & Technology.

De Backer, Daniel; Pinsky, Michael R., Can one predict fluid responsiveness in spontaneously breathing patients?, 2012, Book Section: Springer Berlin Heidelberg.

Pinsky, Michael R; Brochard, Laurent; Mancebo, Jordi, Applied physiology in intensive care medicine, 2006, Book: Springer-Verlag Berlin Heidelberg.

Pizov, Reuven; Tamir, Ada; Gelman, Simon, Arterial and Plethysmographic Waveform Analysis in Anesthetized Patients with Hypovolemia, 2010, Journal : Anesthesiology.

Pizov, R.; Eden, A.; Bystritski, D.; Kalina, E.; Tamir, A.; Gelman, S., Hypotension during gradual blood loss: waveform variables response and absence of tachycardia, 2012, Journal : British Journal of Anaesthesia.

Reddy, K.A.; George, B.; Kumar, V.J., Use of Fourier Series Analysis for Motion Artifact Reduction and Data Compression of Photoplethysmographic Signals, 2009, Journal : IEEE Transactions on Instrumentation and Measurement.

Feissel, Marc; Teboul, Jean-Louis; Merlani, Paolo; Badie, Julio; Faller, Jean-Pierre; Bendjelid, Karim, Plethysmographic dynamic indices predict fluid responsiveness in septic ventilated patients, 2007, Journal : Intensive Care Medicine.

Feissel, Marc; Badie, Julio; Merlani, Paolo G.; Faller, Jean-Pierre; Bendjelid, Karim, Pre-ejection period variations predict the fluid responsiveness of septic ventilated patients:, 2005, Journal : Critical Care Medicine.

Preisman, S.; Kogan, S.; Berkenstadt, H.; Perel, A., Predicting fluid responsiveness in patients undergoing cardiac surgery: functional haemodynamic parameters including the Respiratory Systolic Variation Test and static preload indicators †, 2005, Journal : British Journal of Anaesthesia.

Gribbin, Brian; Steptoe, Andrew; Sleight, Peter, Pulse Wave Velocity as a Measure of Blood Pressure Change, 1976, Journal : Psychophysiology.

Raamat, Rein; Jagomägi, Kersti; Talts, Jaak, Calibrated photoplethysmographic estimation of digital pulse volume and arterial compliance, 2007, Journal : Clinical Physiology and Functional Imaging.

Rehberg, Sebastian; Ertmer, Christian; Westphal, Martin, Valsalva, Valsalva, may you give me a clue, who needs fluids in my ICU?, 2009, Journal : Intensive Care Medicine.

Cannesson, M.; Desebbe, O.; Hachemi, M.; Jacques, D.; Bastien, O.; Lehot, J.-J, Respiratory variations in pulse oximeter waveform amplitude are influenced by venous return in mechanically ventilated patients under general anaesthesia:, 2007, Journal : European Journal of Anaesthesiology.

Abraham, W. T., Disease management: remote monitoring in heart failure patients with implantable defibrillators, resynchronization devices, and haemodynamic monitors, 2013, Journal : Europace.

(56) References Cited

OTHER PUBLICATIONS

Walker, Rhonda L, Vigileo™/FloTrac™ Stroke Volume Variation and Hemodynamic Trends are Reliable for Acute, 2011, Thesis: Harris College of Nursing and Health Sciences.

Rickards, Caroline A.; Vyas, Nisarg; Ryan, Kathy L.; Ward, Kevin R.; Andre, David; Hurst, Gennifer M.; Barrera, Chelsea R.; Convertino, Victor A., Are you bleeding? Validation of a machine-learning algorithm for determination of blood volume status: application to remote triage, 2014, Journal : Journal of Applied Physiology.

Rosenkranz, S.; Mayer, C.; Kropf, J.; Wassertheurer, S., Intelligent multichannel sensors for pulse wave analysis, 2011, Journal : Mathematics and Computers in Simulation.

Rubins, Uldis, Finger and ear photoplethysmogram waveform analysis by fitting with Gaussians, 2008, Journal : Medical & Biological Engineering & Computing.

Sandberg, Frida; Bailon, Raquel; Hernando, David; Laguna, Pablo; Martinez, Juan Pablo; Solem, Kristian; Sornmo, Leif, Prediction of Intradialytic Hypotension using PPG and ECG, 2013, Journal : Computing in Cardiology.

Sandberg, Frida; Bailoón, Raquel; Hernando, David; Laguna, Pablo; Martínez, Juan Pablo; Solem, Kristian; Sörnmo, Leif, Prediction of hypotension in hemodialysis patients, 2014, Journal : Physiological Measurement.

Schafer, Kristin; Van Sickle, Christina; Hinojosa-Laborde, Carmen; Convertino, Victor A., Physiologic mechanisms underlying the failure of the "shock index" as a tool for accurate assessment of patient status during progressive simulated hemorrhage:, 2013, Journal : Journal of Trauma and Acute Care Surgery.

Scully, Christopher G.; Selvaraj, Nandakumar; Romberg, Frederick W.; Wardhan, Richa; Ryan, John; Florian, John P.; Silverman, David G.; Shelley, Kirk H.; Chon, Ki H., Using Time-Frequency Analysis of the Photoplethysmographic Waveform to Detect the Withdrawal of 900 mL of Blood:, 2012, Journal : Anesthesia & Analgesia.

Paukkunen, Mikko, Seismocardiography: Practical implementation and feasibility, 2014, Thesis: Aalto University.

Selvaraj, Nandakumar; Shelley, Kirk H.; Silverman, David G.; Stachenfeld, Nina; Galante, Nicholas; Florian, John P.; Mendelson, Yitzhak; Chon, Ki H., A Novel Approach Using Time—Frequency Analysis of Pulse-Oximeter Data to Detect Progressive Hypovolemia in Spontaneously Breathing Healthy Subjects, 2011, Journal : IEEE Transactions on Biomedical Engineering.

Selvaraj, N.; Scully, C. G.; Shelley, K. H.; Silverman, D. G.; Chon, K. H., Early detection of spontaneous blood loss using amplitude modulation of Photoplethysmogram, 2011, Conference: IEEE.

Seo, Hyungseok; Kong, Yu-Gyeong; Jin, Seok-Joon; Chin, Ji-Hyun; Kim, Hee-Yeong; Lee, Yoon-Kyung; Hwang, Jai-Hyun; Kim, Young-Kug, Dynamic Arterial Elastance in Predicting Arterial Pressure Increase After Fluid Challenge During Robot-Assisted Laparoscopic Prostatectomy: A Prospective Observational Study, 2015, Journal : Medicine.

Shelley, Kirk H; Murray, W Bosseau; Chang, David, Arterial-Pulse Oximetry Loops: A New Method of Monitoring Vascular Tone, 1997, Journal : Journal of Clinical Monitoring.

Shibata, Shigeki; Hastings, Jeff L.; Prasad, Anand; Fu, Qi; Bhella, Paul S.; Pacini, Eric; Krainski, Felix; Palmer, M. Dean; Zhang, Rong; Levine, Benjamin D., Congestive heart failure with preserved ejection fraction is associated with severely impaired dynamic Starling mechanism, 2011, Journal : Journal of Applied Physiology.

Smorenberg, Annemieke; Lust, Erik J.; Beishuizen, Albertus; Meijer, Jan H.; Verdaasdonk, Ruud M.; Groeneveld, A.B. Johan, Systolic time intervals vs invasive predictors of fluid responsiveness after coronary artery bypass surgery †, 2013, Journal : European Journal of Cardio-Thoracic Surgery.

Solem, Kristian; Olde, Bo; Sörnmo, Leif, Prediction of Intradialytic Hypotension Using Photoplethysmography, 2010, Journal : IEEE Transactions on Biomedical Engineering.

Solus-Biguenet, H.; Fleyfel, M.; Tavernier, B.; Kipnis, E.; Onimus, J.; Robin, E.; Lebuffe, G.; Decoene, C.; Pruvot, F.R.; Vallet, B., Non-invasive prediction of fluid responsiveness during major hepatic surgery † ‡, 2006, Journal : British Journal of Anaesthesia.

Soubrier, Stéphane; Saulnier, Fabienne; Hubert, Hervé; Delour, Pierre; Lenci, Hélène; Onimus, Thierry; Nseir, Saad; Durocher, Alain, Can dynamic indicators help the prediction of fluid responsiveness in spontaneously breathing critically ill patients?, 2007, Journal : Intensive Care Medicine.

Stewart, Camille L.; Mulligan, Jane; Grudic, Greg Z.; Convertino, Victor A.; Moulton, Steven L., Detection of low-volume blood loss: Compensatory reserve versus traditional vital signs, 2014, Journal : Journal of Trauma and Acute Care Surgery.

Stewart, Camille L.; Mulligan, Jane; Grudic, Greg Z.; Pyle, Laura; Moulton, Steven L., A Noninvasive Computational Method for Fluid Resuscitation Monitoring in Pediatric Burns: A Preliminary Report, 2015, Journal : Journal of Burn Care & Research.

Ahmed, S. Sultan; Levinson, Gilbert E.; Schwartz, Carl J.; Ettinger, Philip O., Systolic Time Intervals as Measures of the Contractile State of the Left Ventricular Myocardium in Man, 1972, Journal : Circulation.

Tavakolian, Kouhyar; Dumont, Guy A.; Houlton, Geoffrey; Blaber, Andrew P., Precordial Vibrations Provide Noninvasive Detection of Early-Stage Hemorrhage:, 2014, Journal : Shock.

Chaudhry, Sarwat I.; Mattera, Jennifer A.; Curtis, Jeptha P.; Spertus, John A.; Herrin, Jeph; Lin, Zhenqiu; Phillips, Christopher O.; Hodshon, Beth V.; Cooper, Lawton S.; Krumholz, Harlan M., Telemonitoring in Patients with Heart Failure, 2010, Journal : New England Journal of Medicine.

Klersy, Catherine; De Silvestri, Annalisa; Gabutti, Gabriella; Regoli, François; Auricchio, Angelo, A Meta-Analysis of Remote Monitoring of Heart Failure Patients, 2009, Journal : Journal of the American College of Cardiology.

Wilkins, Robert W.; Halperin, Meyer H.; Litter, Julius, The Effect of the Dependent Position upon Blood Flow in the Limbs, 1950, Journal : Circulation.

Hickey, M; Phillips, J P; Kyriacou, P A, The effect of vascular changes on the photoplethysmographic signal at different hand elevations, 2015, Journal : Physiological Measurement.

Pan, Rémy C Martin-Du; Benoit, Raymond; Girardier, Lucia, The role of body position and gravity in the symptoms and treatment of various medical diseases, 2004, Journal : Swiss Med Wkly.

Suehiro, Koichi; Okutani, Ryu, Influence of tidal volume for stroke volume variation to predict fluid responsiveness in patients undergoing one-lung ventilation, 2011, Journal : Journal of Anesthesia.

Grubb, Blair P.; Kosinski, Daniel, Tilt Table Testing: Concepts and Limitations, 1997, Journal : Pacing and Clinical Electrophysiology.

Klein, Liviu, Treating Hemodynamic Congestion is the Key to Prevent Heart Failure Hospitalizations *, 2016, Journal : JACC: Heart Failure.

Trepte, C.J.C.; Eichhorn, V.; Haas, S.A.; Stahl, K.; Schmid, F.; Nitzschke, R.; Goetz, A.E.; Reuter, D.A., Comparison of an automated respiratory systolic variation test with dynamic preload indicators to predict fluid responsiveness after major surgery, 2013, Journal : British Journal of Anaesthesia.

Uretzky, G; Palti, Y, A method for comparing transmitted and reflected light photoelectric plethysmography., 1971, Journal : Journal of Applied Physiology.

Jayasree, V K, Selected Cardiovascular Studies Based on Photoplethysmography Technique, 2009, Thesis: Cochin University of Science and Technology.

Little, William C, Altered elfect of the Valsalva maneuver on left ventricular volume in patients with cardiomyopathy, 1985, Journal :.

Greenfield, Joseph C.; Cox, Ronnie L.; Hernandez, Rafael R.; Thomas, Corinna; Schoonmaker, Fred W., Pressure-Flow Studies in Man During the Valsalva Maneuver with Observations on the Mechanical Properties of the Ascending Aorta, 1967, Journal : Circulation.

Raj, Satish R.; Robertson, David; Biaggioni, Italo; Diedrich, André, Abnormal Valsalva Maneuver is Not Always a Sign of Congestive Heart Failure, 2007, Journal : The American Journal of Medicine.

Van Sickle, Christina; Schafer, Kristin; Mulligan, Jane; Grudic, Gregory Z.; Moulton, Steven L.; Convertino, Victor A., A Sensitive Shock Index for Real-Time Patient Assessment During Simulated Hemorrhage, 2013, Journal : Aviation, Space, and Environmental Medicine.

(56) References Cited

OTHER PUBLICATIONS

Vistisen, Simon Tilma; Juhl-Olsen, Peter; Frederiksen, Christian Alcaraz; Kirkegaard, Hans, Variations in the pre-ejection period induced by deep breathing do not predict the hemodynamic response to early haemorrhage in healthy volunteers, 2014, Journal : Journal of Clinical Monitoring and Computing.
Vistisen, S. T.; Struijk, J. J.; Larsson, A., Automated pre-ejection period variation indexed to tidal volume predicts fluid responsiveness after cardiac surgery, 2009, Journal : Acta Anaesthesiologica Scandinavica.
Wang, Chien-Hao; Lu, Cheng-Wei; Lin, Tzu-Yu; Abbod, Maysam F; Shieh, Jiann-Shing, An Assessment of Pulse Transit Time for Detecting Heavy Blood Loss During Surgical Operation, 2012, Journal : The Open Biomedical Engineering Journal.
Wang, Lu; Xu, Lisheng; Feng, Shuting; Meng, Max Q.-H.; Wang, Kuanquan, Multi-Gaussian fitting for pulse waveform using Weighted Least Squares and multi-criteria decision making method, 2013, Journal : Computers in Biology and Medicine.
Michard, Fr??d??ric, Changes in Arterial Pressure during Mechanical Ventilation:, 2005, Journal : Anesthesiology.
Antonelli, L.; Ohley, W.; Khamlach, R., Dicrotic notch detection using wavelet transform analysis, 1994, Conference: IEEE.
Di Rienzo, M.; Meriggi, P.; Vaini, E.; Castiglioni, P.; Rizzo, F., 24h seismocardiogram monitoring in ambulant subjects, 2012, Conference: IEEE.
Chaudhry, Sarwat I.; Wang, Yongfei; Concato, John; Gill, Thomas M.; Krumholz, Harlan M., Patterns of Weight Change Preceding Hospitalization for Heart Failure, 2007, Journal : Circulation.
Weissler, Arnold M.; Peeler, Robert G.; Roehll, Walter H., Relationships between left ventricular ejection time, stroke volume, and heart rate in normal individuals and patients with cardiovascular disease, 1961, Journal : American Heart Journal.
Lisheng Xu; Shuting Feng; Yue Zhong; Cong Feng; Meng, Max Q. H.; Huaicheng Yan, Multi-Gaussian fitting for Digital Volume Pulse using Weighted Least Squares method, 2011, Conference: IEEE.
Zimmermann, Markus; Feibicke, Thomas; Keyl, Cornelius; Prasser, Christopher; Moritz, Stefan; Graf, Bernhard M; Wiesenack, Christoph, Accuracy of stroke volume variation compared with pleth variability index to predict fluid responsiveness in mechanically ventilated patients undergoing major surgery:, 2009, Journal : European Journal of Anaesthesiology.
Zöllei, Éva; Bertalan, Viktória; Németh, Andrea; Csábi, Péter; László, Ildikó; Kaszaki, József; Rudas, László, Non-invasive detection of hypovolemia or fluid responsiveness in spontaneously breathing subjects, 2013, Journal : BMC Anesthesiology.
Paiva, R.P.; Carvalho, P.; Aubert, X.; Muehlsteff, J.; Henriques, J.; Antunes, M., Assessing PEP and LVET from heart sounds: Algorithms and evaluation, 2009, Conference: IEEE.
Tavakolian, Kouhyar; Dumont, Guy A; Blaber, Andrew P, Analysis of Seismocardiogram Capability for Trending Stroke Volume Changes: A Lower Body Negative Pressure Study, 2012, Journal : computing in cardiology.
Gaddum, N. R.; Alastruey, J.; Beerbaum, P.; Chowienczyk, P.; Schaeffter, T., A Technical Assessment of Pulse Wave Velocity Algorithms Applied to Non-invasive Arterial Waveforms, 2013, Journal : Annals of Biomedical Engineering.
Critchley, Lester A.; Yang, Xiao X.; Lee, Anna, Assessment of Trending Ability of Cardiac Output Monitors by Polar Plot Methodology, 2011, Journal : Journal of Cardiothoracic and Vascular Anesthesia.
Akhtar, Shamsuddin; Matei, Veronica; London, Martin J.; Barash, Paul G., Electrocardiographic Monitoring, 2011, Book Section: Elsevier BV.
Moeslund, Thomas B.; Hilton, Adrian; Krüger, Volker, A survey of advances in vision-based human motion capture and analysis, 2006, Journal : Computer Vision and Image Understanding.
Poppe, Ronald, A survey on vision-based human action recognition, 2010, Journal : Image and Vision Computing.

Hager, David N.; Fuld, Mathew; Kaczka, David W.; Fessler, Henry E.; Brower, Roy G.; Simon, Brett A., Four methods of measuring tidal volume during high-frequency oscillatory ventilation:, 2006, Journal : Critical Care Medicine.
Mijovic, B.; Vos, M. De; Gligorijevic, I.; Taelman, J.; Huffel, S. Van, Source Separation From Single-Channel Recordings by Combining Empirical-Mode Decomposition and Independent Component Analysis, 2010, Journal : IEEE Transactions on Biomedical Engineering.
Parry Fung; Dumont, G.; Ries, C.; Mott, C.; Ansermino, M., Continuous noninvasive blood pressure measurement by pulse transit time, 2004, Conference:.
Jessup, Mariell; Sutton, Martin St.John; Weber, Karl T; Janicki, Joseph S, The effect of chronic pulmonary hypertension on left ventricular size, function, and interventricular septal motion, 1987, Journal : American Heart Journal.
Ambrosi, C.; Chabrillat, Y.; Duport, G.; Valeix, B.; Berthet-Bondet, M.; Gérard, R., [Calculation of the ejection fraction from simultaneously recorded systolic intervals and angiography. Comparative study], 1981, Journal : Archives Des Maladies Du Coeur Et Des Vaisseaux.
Spodick, David H.; Doi, Yoshinori L.; Bishop, Richard L.; Hashimoto, Tetsuo, Systolic time intervals reconsidered: Reevaluation of the preejection period: Absence of relation to heart rate, 1984, Journal : The American Journal of Cardiology.
Li, X.; Chen, J.; Zhao, G.; Pietikäinen, M., Remote Heart Rate Measurement from Face Videos under Realistic Situations, 2014, Conference:.
McDuff, D.; Gontarek, S.; Picard, R. W., Remote Detection of Photoplethysmographic Systolic and Diastolic Peaks Using a Digital Camera, 2014, Journal : IEEE Transactions on Biomedical Engineering.
Teboul, J. -L.; Lamia, B.; Monnet, X., Assessment of Fluid Responsiveness in Spontaneously Breathing Patients, 2007, Conference: Springer Berlin Heidelberg.
Monge García, Manuel Ignacio; Gil Cano, Anselmo; Diaz Monrové, Juan Carlos, Arterial pressure changes during the Valsalva maneuver to predict fluid responsiveness in spontaneously breathing patients, 2008, Journal : Intensive Care Medicine.
Buda, A. J.; Pinsky, M. R.; Ingels, N. B.; Daughters, G. T.; Stinson, E. B.; Alderman, E. L., Effect of intrathoracic pressure on left ventricular performance, 1979, Journal : The New England Journal of Medicine.
Amoroso, P.; Greenwood, R. N., Posture and central venous pressure measurement in circulatory volume depletion, 1989, Journal : Lancet.
Cavallaro, F; Sandroni, Claudio; Antonelli, Massimo, Functional hemodynamic monitoring and dynamic indices of fluid responsiveness, 2008, Journal : Minerva anestesiologica.
Hickey, Michelle; Phillips, Justin P.; Kyriacou, Panayiotis A., Investigation of peripheral photoplethysmographic morphology changes induced during a hand-elevation study, 2016, Journal : Journal of Clinical Monitoring and Computing.
Mitchell, Jamie R.; Wang, Jiun-Jr, Expanding application of the Wiggers diagram to teach cardiovascular physiology, 2014, Journal : Advances in Physiology Education.
Permutt, S.; Riley, R. L., Hemodynamics of collapsible vessels with tone: the vascular waterfall, 1963, Journal : Journal of Applied Physiology.
Magder, Sheldon, Clinical Usefulness of Respiratory Variations in Arterial Pressure, 2004, Journal : American Journal of Respiratory and Critical Care Medicine.
Magder, S., More respect for the CVP, 1998, Journal : Intensive Care Medicine.
Bendjelid, Karim; Romand, Jacques-A., Fluid responsiveness in mechanically ventilated patients: a review of indices used in intensive care, 2003, Journal : Intensive Care Medicine.
Ansari, B. M.; Zochios, V.; Falter, F.; Klein, A. A., Physiological controversies and methods used to determine fluid responsiveness: a qualitative systematic review, 2016, Journal : Anaesthesia.
Kumar, Dinesh, Automatic Heart Sound Analysis for Cardiovascular Disease -annotated.pdf, 2014, Thesis: University of Coimbra.

(56) References Cited

OTHER PUBLICATIONS

Sterns, Richard; Emmett, Michael, Etiology, clinical manifestations, and diagnosis of volume depletion in adults, 2019, Document: UpToDate.

Pinsky, Michael R., Heart-lung interactions, 2007, Journal : Current Opinion in Critical Care.

Michard, Frédéric; Teboul, Jean-Louis, Predicting Fluid Responsiveness in ICU Patients, 2002, Journal : Chest.

Weissler, Arnold M.; Harris, Leonard C.; White, George D., Left ventricular ejection time index in man, 1963, Journal : Journal of Applied Physiology.

Stevenson, Lynne Warner; Perloff, Joseph K., The Limited Reliability of Physical Signs for Estimating Hemodynamics in Chronic Heart Failure, 1989, Journal : JAMA.

Lewin, Jennifer; Ledwidge, Mark; O'Loughlin, Christina; McNally, Clare; McDonald, Ken, Clinical deterioration in established heart failure: What is the value of BNP and weight gain in aiding diagnosis?, 2005, Journal : European Journal of Heart Failure.

Han, Fei; Reily, Brian; Hoff, William; Zhang, Hao, Space-time representation of people based on 3D skeletal data: A review, 2017, Journal : Computer Vision and Image Understanding.

Tamura, Toshiyo; Maeda, Yuka; Sekine, Masaki; Yoshida, Masaki, Wearable Photoplethysmographic Sensors—Past and Present, 2014, Journal : Electronics.

Sokwoo Rhee; Boo-Ho Yang; Asada, H.H., Artifact-resistant power-efficient design of finger-ring plethysmographic sensors, 2001, Journal : IEEE Transactions on Biomedical Engineering.

Sola, Josep; Chetelat, Olivier, Combination of multiple light paths in pulse oximetry: the finger ring example, 2007, Conference: IEEE.

Maeda, Yuka; Sekine, Masaki; Tamura, Toshiyo, The Advantages of Wearable Green Reflected Photoplethysmography, 2011, Journal : Journal of Medical Systems.

De Paula, Erich Vinicius, Tides within ourselves: how posture can affect blood volume, blood cells and clinical reasoning, 2017, Journal : Revista Brasileira de Hematologia e Hemoterapia.

Wiens, Andrew D, Detecting Aortic Valve Opening and Closing from Distal Body Vibrations, 2016, Journal : rXiv preprint arXiv:.

O'Rourke, Michael F; Gallagher, David E, Pulse wave analysis., 1996, Journal : Journal of hypertension. Supplement: official journal of the International Society of Hypertension.

Fan, Zhaopeng; Zhang, Gong; Lia, Simon, Pulse Wave Analysis, 2011, Book Section: IntechOpen.

Di Rienzo, Marco, Wearable seismocardiography for the beat-to-beat assessment of cardiac intervals during sleep, 2014, Conference:.

Weissler, Arnold M., Systolic-time intervals, 1977, Journal : New England Journal of Medicine.

Levick, J. Rodney, An introduction to cardiovascular physiology, 2013, Book Section: Butterworth-Heinemann.

Sami, A., et al., Passive leg rising and pulse contour monitoring, 2006, Conference:.

Weissler, Arnold M., Leonard C. Harris, and George D. White, Left Ventricular Ejection Time in man, 1963, Journal : Journal of applied physiology.

Cherpanath, Thomas GV, et a, Predicting fluid responsiveness by passive leg raising: a systematic review and meta-analysis of 23 clinical trials., 2016, Journal : Critical care medicine.

Abbas, Abbas K., and Rasha Bassam, Phonocardiography signal processing, 2009, Journal : Synthesis Lectures on Biomedical Engineering.

Kenny, Jon Emile, ICU Physiology in 1,000 Words_Stroke Volume Variation nd the Concept of Dose-Response, 2014, Blog Post: https://pulmccm.org/review-articles/icu-physiology-1000-words-stroke-volume-variation-concept-dose-response/.

Feihl, François, and Alain F. Broccard, Interactions between respiration and systemic hemodynamics. Part II: practical implications in critical care, 2009, Journal : Applied Physiology in Intensive Care Medicine.

Ajith Kumar, P. C., & Ananthapadmanabha, T. V., Ajith Kumar, P. C., and T. V. Ananthapadmanabha. Heart rate variability using Shannon energy, digital signal and image processing centre, 2006, Journal : MSRSAS.

Frazier, John; Hatib, Feras, Getting ml beat from mmHg: Arterial Pressure-based Cardiac Output, 2008, Document: Edwards Lifesciences.

\* cited by examiner

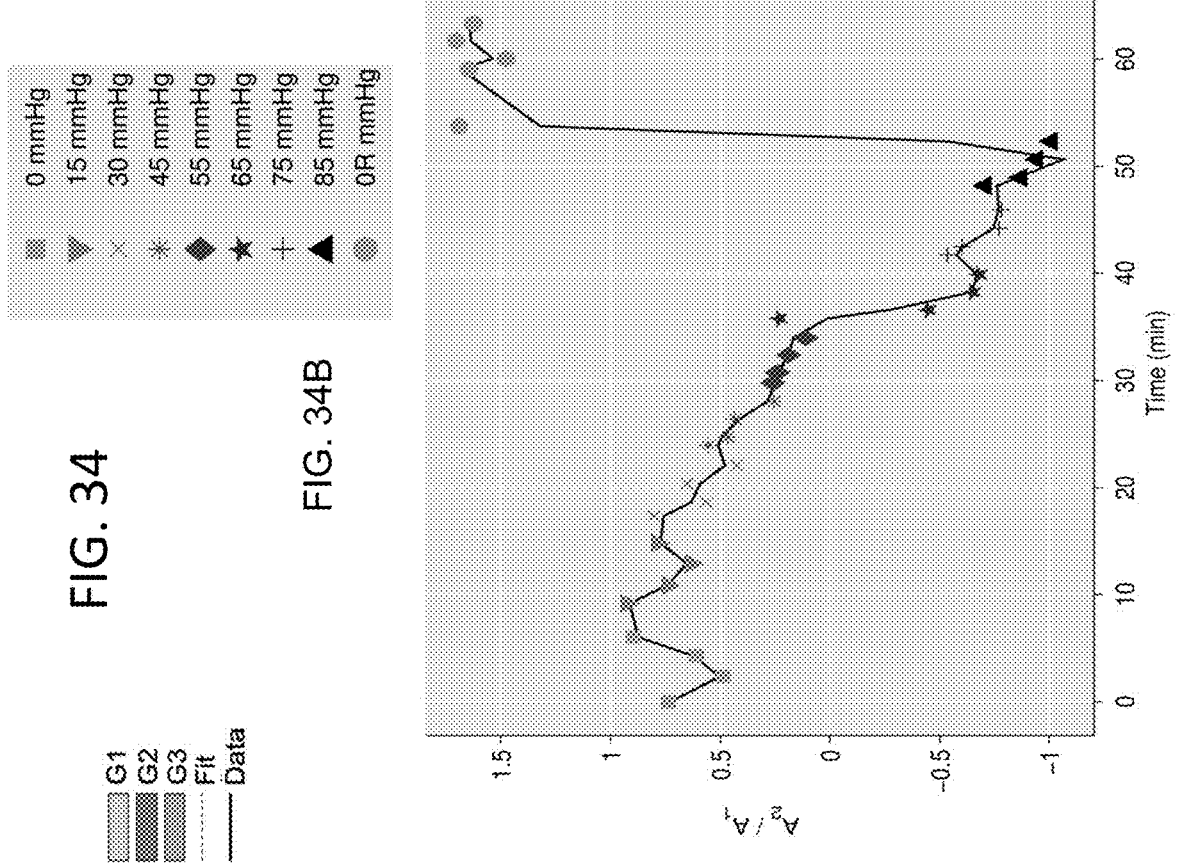
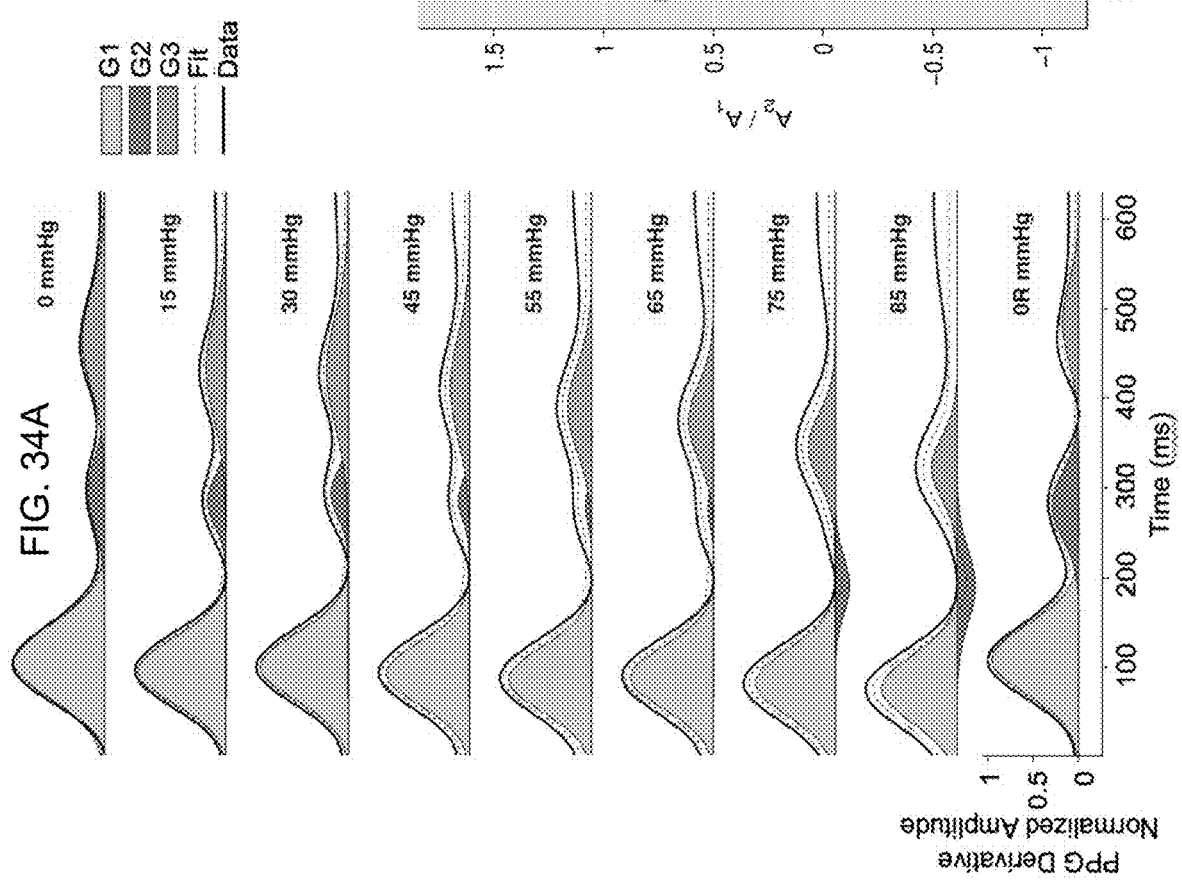
FIG. 34
FIG. 34A
FIG. 34B

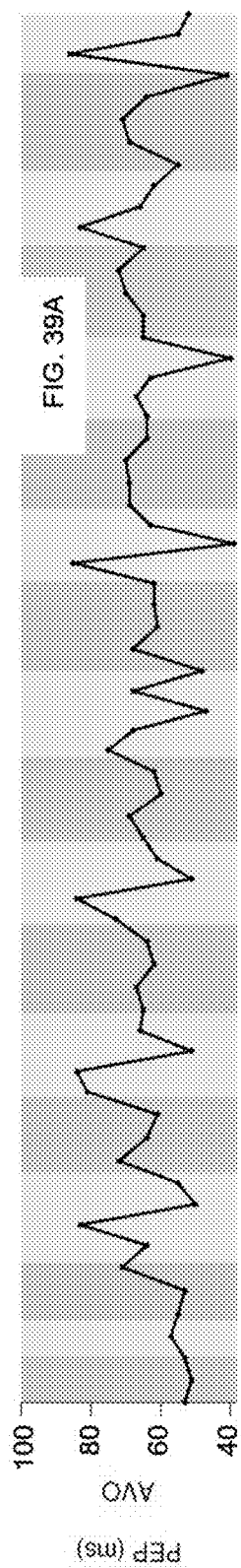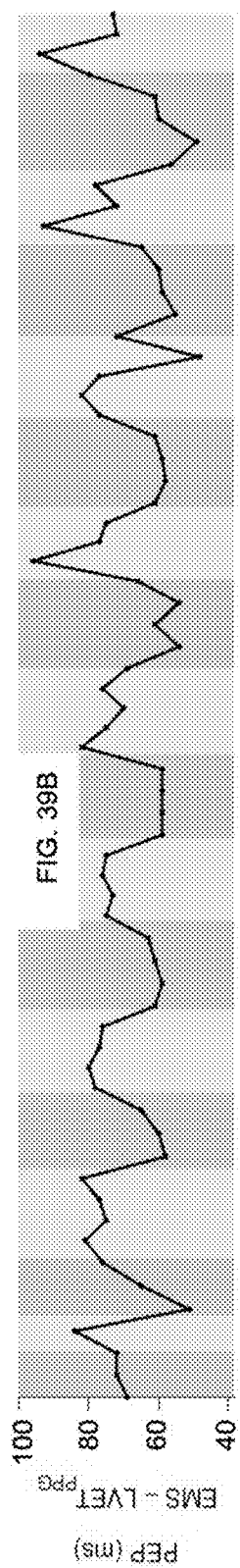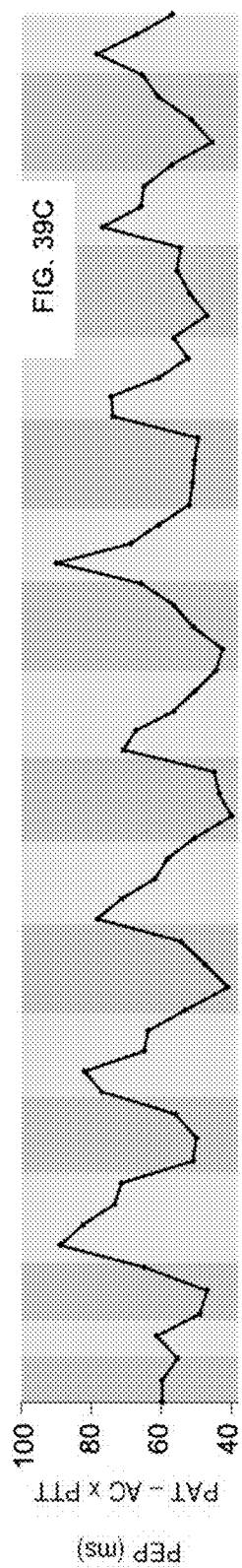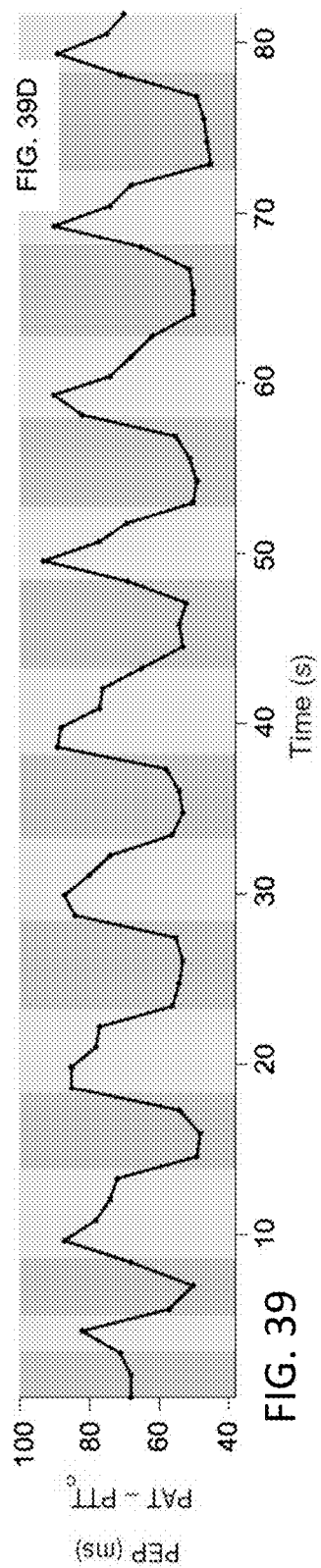
FIG. 39

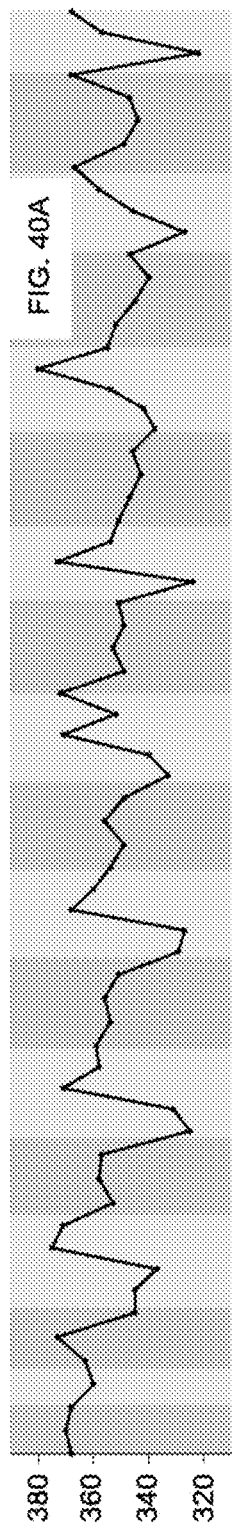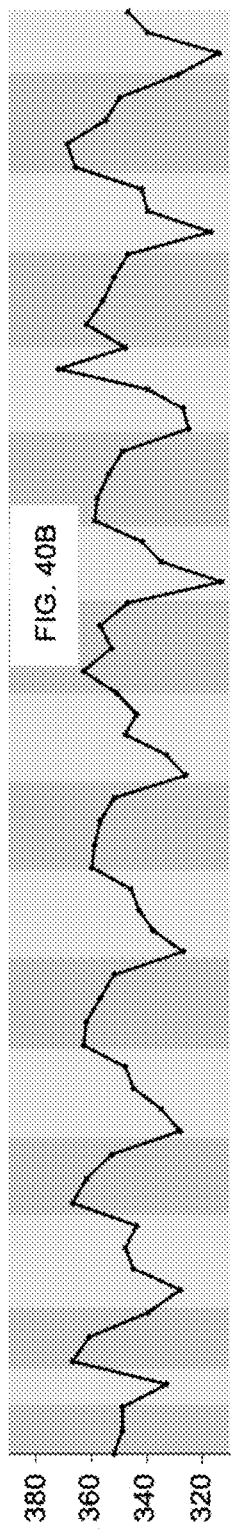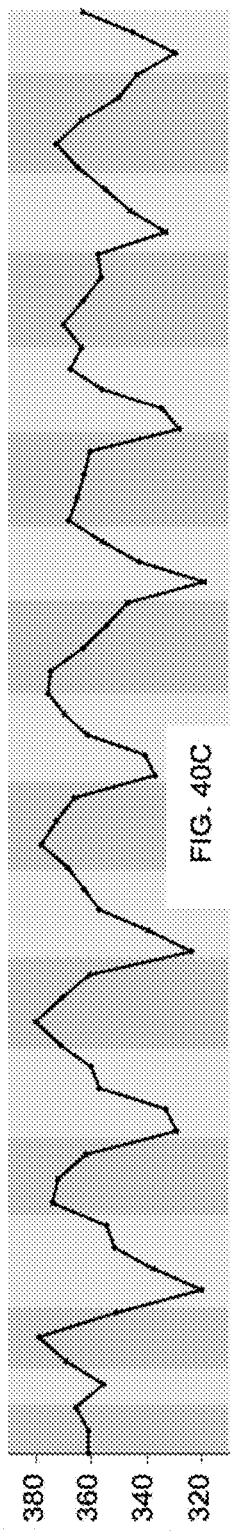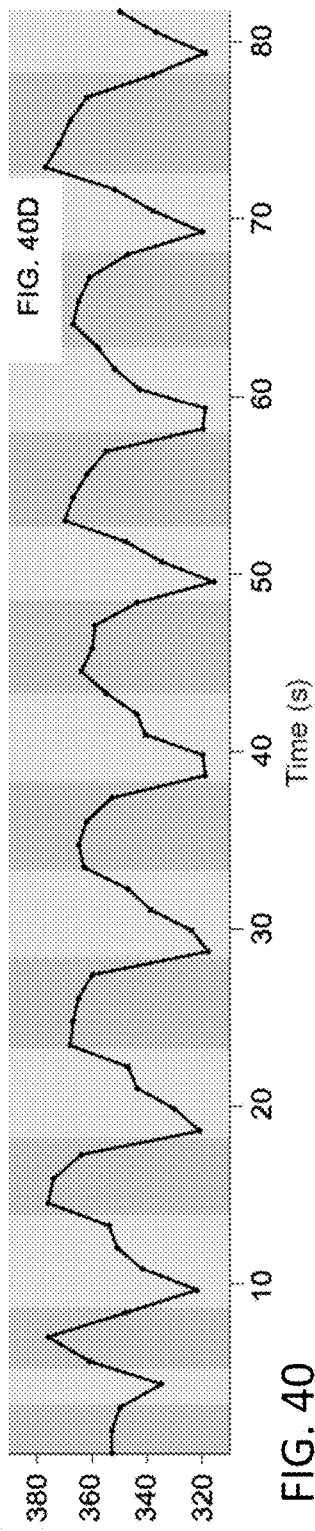
FIG. 40

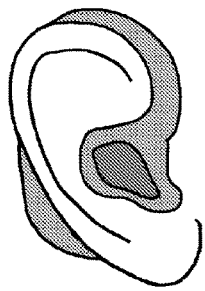
Figure 47
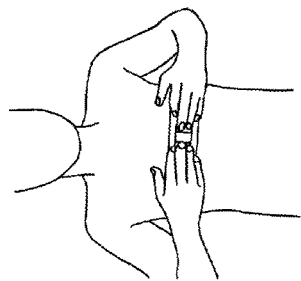
Figure 48
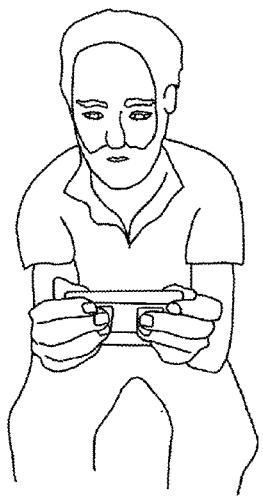
Figure 49
Figure 51
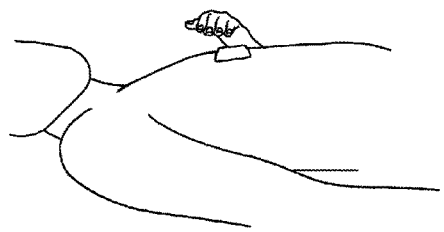
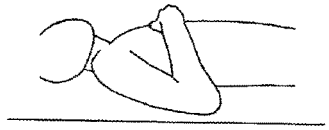
Figure 50

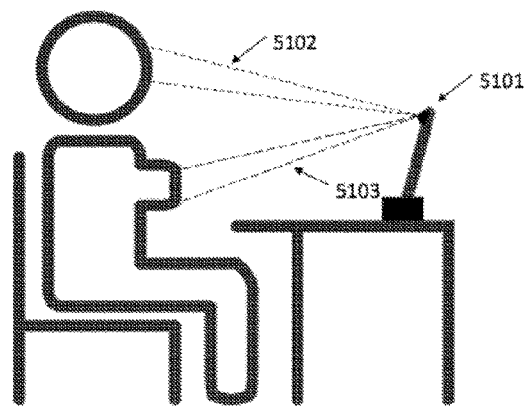
Figure 52
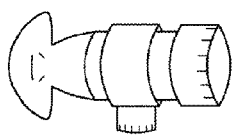
Figure 53
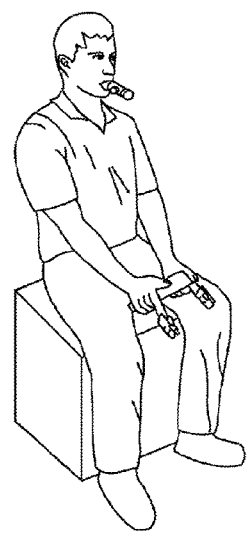
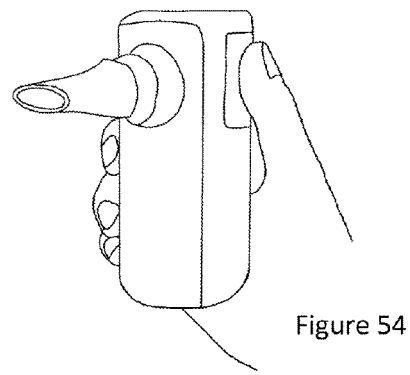
Figure 54

METHODS AND APPARATUSES FOR ASSESSMENT AND MANAGEMENT OF HEMODYNAMIC STATUS

CROSS-REFERENCE TO RELATED APPLICATIONS

This application is a national stage application under 35 U.S.C. 371 of PCT application PCT/US2016/065140, filed 2016 Dec. 6, which claims priority to U.S. provisional applications 62/263,839, filed 2015 Jul. 12, 62/375,431 filed 2016 Aug. 15, and 62/423,701 filed 2016 Nov. 17. Each of the foregoing is incorporated by reference herein.

BACKGROUND OF THE INVENTION

The determination of hemodynamic status and subsequent treatment of hemodynamically compromised patients is challenging. Treatment decisions are often based upon the performance of two critical physiological processes: cardiac function and venous return function, which is determined by the return of blood to the heart. The management of cardiac output is dependent upon changes to one or both of these two functions. Pinsky has simplified the complex therapeutic decision process to two functional performance-based questions: (1) Will blood flow to the body increase (or decrease) if the patient's intravascular volume is increased (or decreased), and if so, by how much, and (2) Is any decrease in arterial pressure due to loss of vascular tone or merely due to inadequate blood flow? These two questions can be summarized as the determination of fluid responsiveness and the determination of vascular tone, respectively.

Various publications are referenced in the description that can aid in understanding the present invention. Each of these publications is incorporated herein by reference.

Fluid Responsiveness

In hemodynamically compromised patients, volume expansion is frequently used to improve the hemodynamic profile and restore adequate blood pressure when an absolute or relative hypovolemia is suspected. Hemodynamic measurements (right atrial pressure [Rap], pulmonary artery occlusion pressure [Ppao], and cardiac output [CO]) are routinely used to evaluate volume status. These measurements are often referred to as static measurement parameters. However, many studies have demonstrated that these indices are not reliable predictors of fluid responsiveness (FR), i.e., whether or not the patient will respond positively to administered fluids. The results of these studies highlight that more informative indices are needed to correctly predict the response to volume therapy.

According to the Starling law, which describes a positive relation between cardiac muscle fiber length and contractility, fluid administration is thought to improve CO by increasing preload. However, as shown in FIG. 1, the Starling curve reaches a plateau beyond its ascending limb. Further fluid administration can be deleterious, leading to right ventricular overload and/or pulmonary edema. Patients that respond to additional volume with improved CO are referred to as volume responders where as those that do not respond are referred to as volume non-responders. The identification of volume responders is critical because only 40-70% of critically ill patients respond to fluid administration with a clinically significant increase in stroke volume (SV) and cardiac output (CO). Michard F, Teboul J L. Predicting fluid responsiveness in ICU patients: a critical analysis of the evidence. Chest. 2002; 121(6): 2000-8.

Static indices such as right atrial pressure (Rap), pulmonary artery occlusion pressure (Ppao), right ventricular end-diastolic volume index (RVEDVI), and left ventricular end-diastolic volume index (LVEDVI) have not been found to accurately predict fluid responsiveness in mechanically ventilated patients. Bendjelid K, Romand J A: Fluid responsiveness in mechanically ventilated patients: A review of indices used in intensive care. Intensive Care Med 2003; 29:352-360. In contrast, dynamic or functional indices (which are based on variations in systolic pressure, pulse pressure, pre-ejection period, left ventricular ejection time, and stroke volume) have been shown to be reliable predictors of fluid responsiveness.

The determination of preload dependency or fluid responsiveness is done by examining stroke volume variation (SVV) by assessment of secondary markers of stroke volume to include systolic pressure variation (SPV) and pulse pressure variation (PPV). These dynamic indices are based on respiration-induced changes in venous return. Pinsky M R. Heart-lung interactions. CurrOpinCrit Care. 2007; 13(5): 528-31. and associated variations in left ventricular preload that cause arterial pressure variances.

Although it has been demonstrated in previous studies that dynamic indices are of clinical value, their application remains limited to patients who are mechanically ventilated with high tidal volumes. Lansdorp B, Lemson J, van Putten M J, de K A, van der Hoeven J G, Pickkers P. Dynamic indices do not predict volume responsiveness in routine clinical practice. BrJ Anaesth. 2011.

In contrast, in spontaneously breathing critically ill patients, both PPV and SPV are not accurate in predicting fluid responsiveness due to insufficient sensitivity (63% and 47%, respectively). Soubrier S, Saulnier F, Hubert H, Delour P, Lenci H, Onimus T, et al. Can dynamic indicators help the prediction of fluid responsiveness in spontaneously breathing critically ill patients? Intensive Care Med. 2007; 33(7): 1117-24. Similarly, in mechanically ventilated patients with spontaneous breathing, PPV does not identify responders to fluid administration. Heenen S, De B D, Vincent J L. How can the response to volume expansion in patients with spontaneous respiratory movements be predicted? Crit Care. 2006; 10(4): R102. This lack of performance in spontaneously breathing subjects is because the physiological variations used in dynamic indices depends on the heart-lung interactions produced during well-defined and stable positive-pressure mechanical ventilation cycles. Spontaneous breathing conditions differ from positive pressure ventilation in deeply sedated patients because (1) intrathoracic pressure is negative during inspiration. Magder S: More respect for the CVP. Intensive Care Med 1998; 24:651-653. Magder S: Clinical usefulness of respiratory variations in arterial pressure. Am J Respir Crit Care Med 2004; 169: 151-155. (2) respiratory rate is variable, and (3) the amplitude of the intrathoracic pressure swings are much lower in spontaneous breathing than in mechanical ventilation. In spontaneous breathing the magnitude of the respiratory induced preload alterations is typically considered as being too small and variable between consecutive breaths and therefore unable to predict volume responsiveness. Thus, as stated by Coudray et al., dynamic indexes are valid only when measured in deeply sedated mechanically ventilated patients in sinus rhythm, since in that condition they result from heart-lung interaction during well-defined, stable, positive-pressure ventilation. Coudray, Alice, et al. "Fluid responsiveness in spontaneously breathing patients: a review of indexes used in intensive care." CRITICAL CARE MEDICINE-BALTIMORE-33.12 (2005): 2757. Bendjelid K, Romand J A: Fluid responsiveness in mechanically ventilated patients: A review of indices used in intensive care. Intensive Care Med 2003; 29:352-360.

Vascular Tone

Effective management of hemodynamically compromised patient should be aimed at achieving not only adequate cardiac output but also sufficient mean arterial pressure (MAP) to guarantee adequate tissue perfusion pressure. Since the arterial pressure response to volume expansion or fluid loading depends on arterial tone, knowing whether a patient is fluid responsive or preload-dependent provides only a partial solution to the problem. Stated simply, a patient can exhibit symptoms associated with hypovolemia due to vasodilation of the vascular system (i.e., the system capacity is large due to vasodilation) or due to low vascular volume (i.e., the system is not adequately filled).

An important concept for the understanding of venous return is that of stressed and unstressed volume. The venous system, like any other elastic structure, will fill with a certain volume, called the 'unstressed' volume, without changing the pressure or causing distention of the structures. Unstressed volume represents as much as 25% of total blood volume and constitutes a significant reservoir for internally recruiting volume into the system. The difference between the total volume in the system and the unstressed volume is the relevant volume for causing pressure in the filling chamber, the stressed volume. A determinant in venous return is the stressed volume (i.e. the difference between total volume and unstressed volume), which is associated with vascular tone. Specifically, vasoconstriction by contraction of smooth muscles in these vessels due to neurosympathetic activation or exogenous catecholamines can decrease venous capacitance by converting unstressed volume into stressed volume, thus raising mean systemic pressure. Magder S, Scharf S: Venous return. In Respiratory-Circulatory Interactions in Health and Disease. Edited by Scharf S M, Pinsky M R, Magder S. New York: Marcel Dekker, Inc.; 2001:93-112.

Dynamic arterial elastance (Eadyn), defined as the pulse pressure variation (PPV) to stroke volume variation (SVV) ratio has been used to predict the hemodynamic response in mean arterial blood pressure to fluid administration. For example, subjects who are preload-responsive and also have decreased vasomotor tone as defined by dynamic arterial elastance will not increase their mean arterial pressure with volume expansion alone. Tissue hypoperfusion will persist with isolated volume expansion, thus vasopressor combined with fluid resuscitation is the recommended treatment. In contrast, subjects who are not preload-responsive but have reduced vasomotor tone need only vasopressor therapy to sustain organ perfusion pressure. This scenario exists with classic neurogenic shock following volume expansion, but can be a sustaining quality of volume expansion in septic shock.

Chronic Heart Disease

Fluid overload is one of the primary causes of CHF-related hospitalizations. Regular monitoring of the symptoms of fluid overload, such as shortness of breath, swelling, fatigue, and weight gain, is a common component of CHF management, however these symptoms are not sensitive enough to reflect early pathophysiologic changes that increase the risk of decompensation. Lewin J, Ledwidge M, O'Loughlin C, McNally C, McDonald K. Clinical deterioration in established heart failure: what is the value of BNP and weight gain in aiding diagnosis? Eur J Heart Fail. 2005; 7(6):953-957. Stevenson L, Perloff J K. The limited reliability of physical signs for estimating hemodynamics in chronic heart failure. JAMA. 1989; 261(6):884-888. Several studies have demonstrated that elevations in pulmonary artery pressure closely correlate with worsening heart failure and can increase several days or weeks before signs and symptoms manifest. Chaudhry S I, Wang Y, Concato J, Gill T M, Krumholz H M. Patterns of weight change preceding hospitalization for heart failure. *Circulation.* 2007; 116(14): 1549-1554.

The pathophysiology of fluid retention is complex and involves both hemodynamic and clinical congestion. Hemodynamic congestion occurs when cardiac output (the mathematical product of stroke volume and heart rate) is insufficient in meeting the oxygen demands of the body. The causes of CHF are well known, and typically include coronary heart disease, valvular heart disease, diabetes, hypertension, obesity, and smoking. The common characteristic is elevation of the pressure within the left atrium at the end of its contraction cycle, or left ventricular end-diastolic pressure (LVEDP). Chronic elevation of LVEDP causes transudation of fluid from the pulmonary veins into the lungs, resulting in shortness of breath (dyspnea), rapid breathing (tachypnea), and fatigue with exertion due to the mismatch of oxygen delivery and oxygen demand throughout the body. Early compensatory mechanisms include increased respiratory rate and heart rate. As cardiac output is compromised, the kidneys respond by retaining sodium and water, leading to an increase in intravascular volume. As the LVEDP rises, pulmonary venous congestion worsens. Body weight increases incrementally and fluid may shift into the lower extremities. Medications for heart failure aim to interrupt the kidneys' hormonal responses to diminished perfusion, and also work to help excrete excess sodium and water from the body. Nonetheless, this is an extremely delicate balance. An increase in blood pressure (which relates to afterload), or fluid retention (which relates to preload), or a significant change in heart rate due to a tachyarrhythmia can lead to decompensated CHF. Decompensated CHF is characteristically unresponsive to oral medications, thus admission to a hospital is often necessary for intravenous diuretic therapy.

Heart failure occurs due to inadequate cardiac output which is directly related to stroke volume. Management goals are thus focused on the optimization of stroke volume by. Stroke volume is critically dependent on the volume of blood in the left ventricle at the end of diastole, the end diastolic volume. FIG. 2 is a graphical representation of patient with heart failure. The overall performance of the heart as defined by stroke volume is decreased with increased end diastolic filling pressures. Additionally, the cardiac output of the heart failure patient can decrease with fluid overload. The limited range of optimal performance as labeled "target volume" is a fluid management challenge as depicted using the Frank-Starling curve. Thus, fluid management in these patients is critical; too little fluid leads to decreases stroke volume while fluid overload also leads to decreased stroke volume.

Accurate Monitoring of Fluid Status is Difficult

Decreases in stroke volume with heart failure are associated with hemodynamic congestion. Hemodynamic congestion is defined as an increase in left ventricular filling and/or intravascular pressures and decrease stroke volume. Hemodynamic congestion is a form of fluid retention that occurs earlier than does clinical congestion. Even when signs and symptoms of clinical congestion are relieved, patients may still have hemodynamic congestion that could lead to progression of heart failure and worsening prognosis. Physical findings associated with clinical congestion are weight gain, nocturia, elevated jugular venous pressure, lower extremity edema, positive hepatojugular reflux, paroxysmal nocturnal dyspnea, and crackles. The inability to determine the presence of clinical congestion is a significant problem in the management of patients with congestive heart failure. This fundamental problem is shown in FIG. 3. Clinical congestion begins to occur prior to the development of physical findings such as weight gain. Research indicates that weight lags hemodynamic congestion changes by as much as 1 to 2 weeks. Stated another way, the most common method for monitoring volume, weight increase, may indicate that CHF is present but at a point that does not allow effective intervention.

Although ventricular filling pressures can be accurately assessed using pulmonary artery catheterization, this approach is highly invasive and associated with significant risks, making it an impractical means of assessing volume status in the majority of patients with heart failure. Physical examination may provide important clues to filling pressures, but is also associated with substantial limitations and poor sensitivity. In addition, physical findings of volume overload, such as peripheral edema and elevated jugular venous pressure, are late signs that are often not present until ventricular filling pressures are extremely elevated, particularly in patients with long-standing chronic heart failure. Thus, there is a disassociation between "hemodynamic congestion" (i.e., elevation of left ventricular filling pressures) and "clinical congestion" (i.e., physical signs of volume overload). An accurate, reliable, inexpensive, and noninvasive means of quantifying "hemodynamic congestion" would be a major advance in heart failure management. The current invention addresses this deficiency in heart failure monitoring.

SUMMARY OF THE INVENTION

The present invention is related to U.S. provisional applications 62/263,839, 62/375,431, and 62/423,701, each of which is incorporated herein by reference. Embodiments of the present invention provide reliable, convenient, and cost-effective methods and apparatuses to determine the hemodynamic status of the patent. The methods and apparatuses provide for the noninvasive determine of hemodynamic status by using systematic perturbations of venous return or trend observation over time. Embodiments do not require invasive pressure monitoring or the use of ventilator but instead can be an entirely noninvasive system. The present invention represents a departure from prior approaches by using mini-Mueller and mini-Valsalva controlled breathing activities or patient-initiated changes in body position to create systematic changes in venous return. These changes in cardiac function are then evaluated on a beat-to-beat basis with awareness of the phase of the breathing (inhale or exhale), the position of the patient, or both. The system provides important information on fluid responsiveness including dynamic and static parameters for hemodynamic assessment for treatment of patients in the emergency department and urgent care, the dialysis clinic, as well as the home of the patient. Embodiments of the invention allow the care provider to determine if blood flow to the body will increase (or decrease) if the patient's intravascular volume is increased (or decreased), and whether any decrease in arterial pressure is due to loss of vascular tone or due to inadequate blood flow. Additionally, the system is able to determine the onset of hemodynamic congestion prior to the development of physical symptoms and to characterize the degree of heart failure through analysis of the subject's response to a systematic perturbation in venous return.

BRIEF DESCRIPTION OF THE DRAWINGS

FIG. 34 is a plot of invention-derived pulse contour changes during lower body negative pressure.

FIG. 39 compares PEP estimates between several embodiments.

FIG. 40 compares LVET estimates between several embodiments.

FIG. 47 is a schematic of a hemodynamic assessment system using a head PPG sensor.

FIG. 48 is a mobile device measurement system.

FIG. 49 is a mobile device measurement system doing remote PPG measurements.

FIG. 50 is a schematic representation of the mobile device doing SCG measurements.

FIG. 51 is a mobile device measurement system with PCG attachment.

FIG. 52 is a schematic illustration of a position determination system

FIG. 53 is a schematic representation of patient with device doing controlled breathing.

FIG. 54 is a schematic of a variable pressure hemodynamic system.

DESCRIPTION OF THE INVENTION

Figure 1:
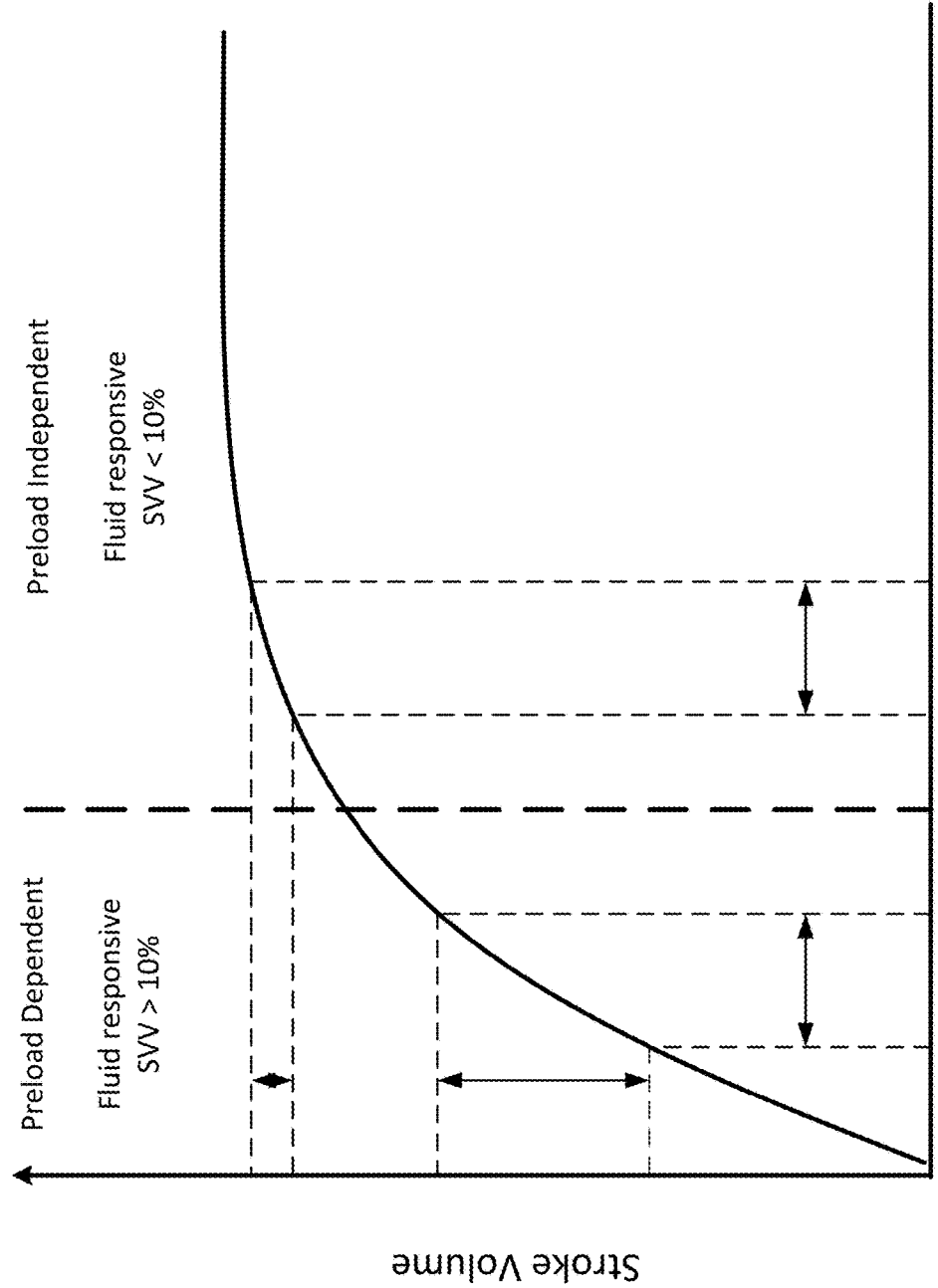
FIG. 1 is a schematic representation shows fluid responsive area of the Frank-Starling curve.

Embodiments of the present invention provide methods and apparatuses for the assessment of hemodynamic status. The system can use an electrocardiogram (ECG), photoplethysmogram (PPG) and/or phonocardiogram (PCG) to estimate parameters associated with vascular tone and stroke volume based upon heart ejection periods, pulse wave velocity, and pulse amplitudes. Systematic changes in venous return can be generated by using mini-Mueller and mini-Valsalva activities. Patient initiated changes in body position can also be used to create venous return perturbations. The system records and subsequently processes the necessary physiological signals for determination of clinically relevant information needed to effectively diagnose and treat hemodynamic conditions. The parameters measured provide the care provider with static information regarding general blood volume status but also include dynamic parameters. Specifically, the system can provide information on heart-lung phase relationship, stroke volume variance, dynamic arterial elastance, percent change in stroke volume, an estimation of heart failure, and the patient's location on the Frank-Starling curve.

Definitions

As used herein, "volume assessment" includes but is not limited to the general assessment of volume in the human body including intravascular volume, extra vascular volume, dehydration, total body water, extracellular volume, and plasma volume. In medicine, intravascular volume status refers to the volume of blood in a patient's circulatory system, and is essentially the blood plasma component of the overall volume status of the body, which otherwise includes both intracellular fluid and extracellular fluid. The intravascular component is usually of primary interest, and volume status is sometimes used synonymously with intravascular volume status.

Hemodynamic congestion is defined as an increase in left ventricular filling and/or intravascular pressures and decrease stroke volume. Hemodynamic congestion is a form of fluid retention that occurs earlier than does clinical congestion.

The Frank-Starling law of the heart (also known as Starling's law or the Frank-Starling mechanism or Maestrini heart's law) states that the stroke volume of the heart increases in response to an increase in the volume of blood filling the heart (the end diastolic volume) when all other factors remain constant. In a healthy heart, a larger volume of blood flowing into the ventricle stretches the walls of the heart, causing a greater expansion during diastole. This in turn increases the force of the contraction during systole and thus the quantity of blood that is pumped into the aorta.

End-diastolic volume (EDV) is the volume of blood in the right and/or left ventricle at the end of filling (diastole), or the amount of blood in the ventricles just before systole. End-diastolic volume is often used synonymously with preload.

As used herein, photoplethysmography (PPG) is an optical measurement technique that can be used to detect blood volume changes in tissue or has a signal that is related to the cardiac cycle.

Arterial compliance refers to the general ability of a blood vessel wall to expand and contract passively with changes in pressure and includes a multitude of metrics and terms used to refer to related properties such a stiffness, elastance, Young's modulus, elastic modulus, distensibility, and other parameters.

Resistance breathing is a general term that applies to any method that increases, decreases, or changes intrathoracic pressure over normal breathing. A resistance breathing test can include inhalation resistance breathing or exhalation resistance breathing, independently or in combination. The use of exhalation resistance breathing creates an increase in intrathoracic pressure while the use of inhalation resistance breathing creates decreased intrathoracic pressures. Additionally, the system can use different levels of resistance over the course of the protocol. The system can create and monitor if needed the inspiratory pressure and expiratory pressure of the subject so that highly repeatable results are obtained. The process can be coupled with a paced breathing system with control over both pressure and the depth of breathing. Additionally, the term resistance breathing covers the process of creating a change in intrathoracic pressure where little or no air movement occurs. The creation of an occlusion pressure either increased or decreased is encompassed as part of the broad definition of resistance breathing. Resistance breathing is a method that can be used to change venous return to the heart and influence end diastolic volume.

Paced breathing is a breathing pattern with defined criteria on rate and can include depth of breathing as well. Typically, paced breathing is slow breathing at a rate between 5 and 7 breaths per minute. With normal breathing, the rate is about 12 to 14 breaths a minute. Paced breathing can include defined changes in the rate as well as an asymmetric breathing profile, for example the exhale is 8 seconds while the inhale is 5 seconds. Paced breathing can be used independently or in combination with resistance breathing.

Controlled breathing is the process of combining elements of paced breathing with resistance breathing. The "controlled" aspect is a system or method of breathing that dictates breathing rate and creates an intrathoracic pressure change that is greater than normal breathing. Examples of controlled breathing include but are not limited to a mini-Mueller inhale against resistance followed by a mini-Valsalva against resistance at a rate of 6 breaths per minute. Controlled breathing can also be done without the application of additional resistance since controlled breathing is defined as a process that dictates breathing rate and creates greater intrathoracic pressure changes than normal breathing.

Hydrostatic positional change is a general term that applies to any process that changes the hydrostatic pressure in a vessel due to positional changes.

Pulse wave velocity is a general term relating to the speed of travel of a pulse wave in the vasculature. Pulse travel time is related to pulse wave velocity and is simply the time associated with the propagation of a pulse wave between two points.

The term "signal" as used herein is meant to and include without limitation, an analog electrical waveform or digital representation thereof, which is collected or transmitted by a biological or physiological sensor, such as a PPG, ECG, SCG or PCG.

The term "pre-ejection period" as used herein, is meant to mean and include the time from the onset of ventricular depolarization to the opening of the aortic valve during the cardiac cycle.

General Physiology

Figure 4:
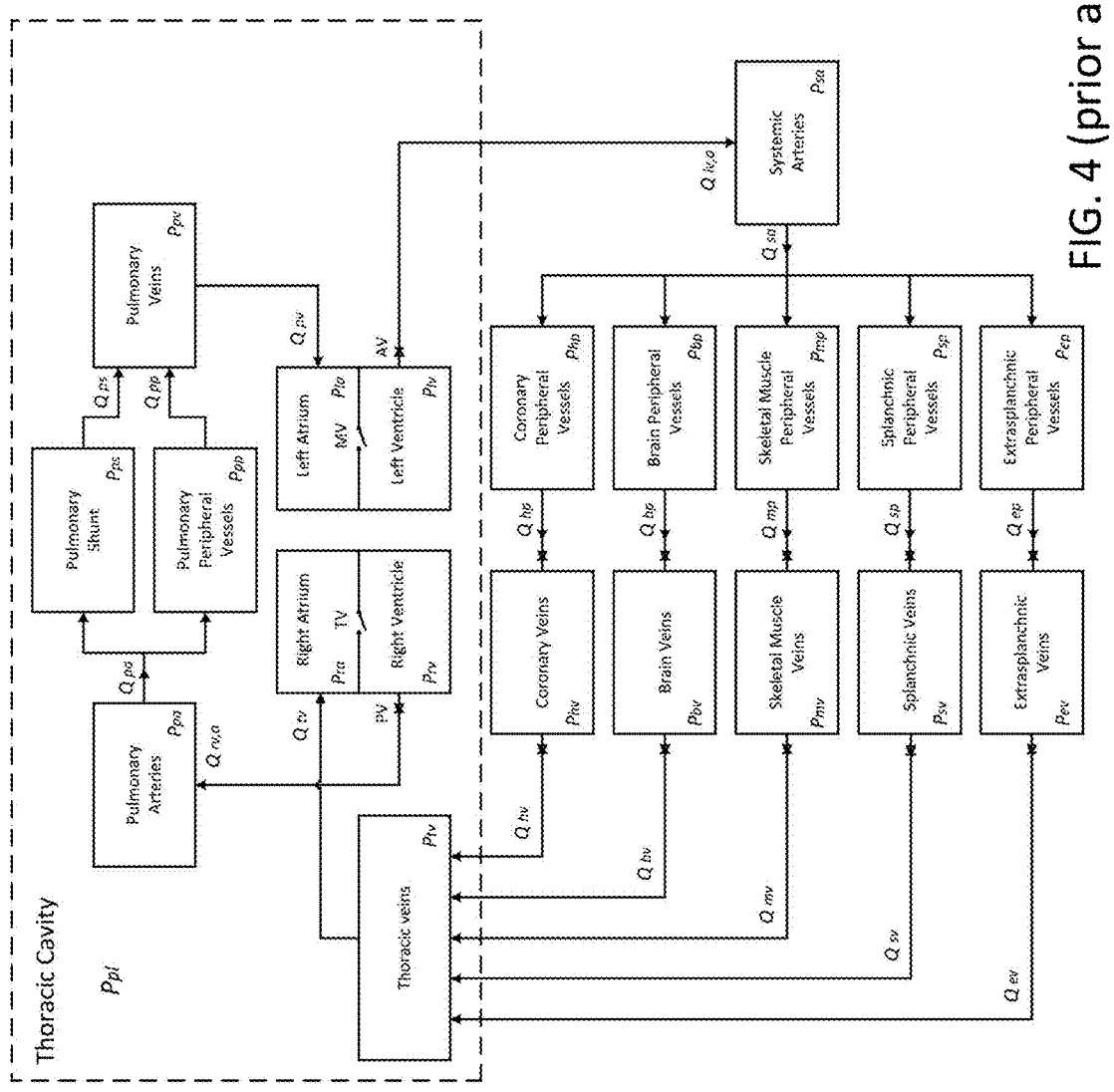
FIG. 4 is a schematic representation of the cardiovascular system.
Figure 5:
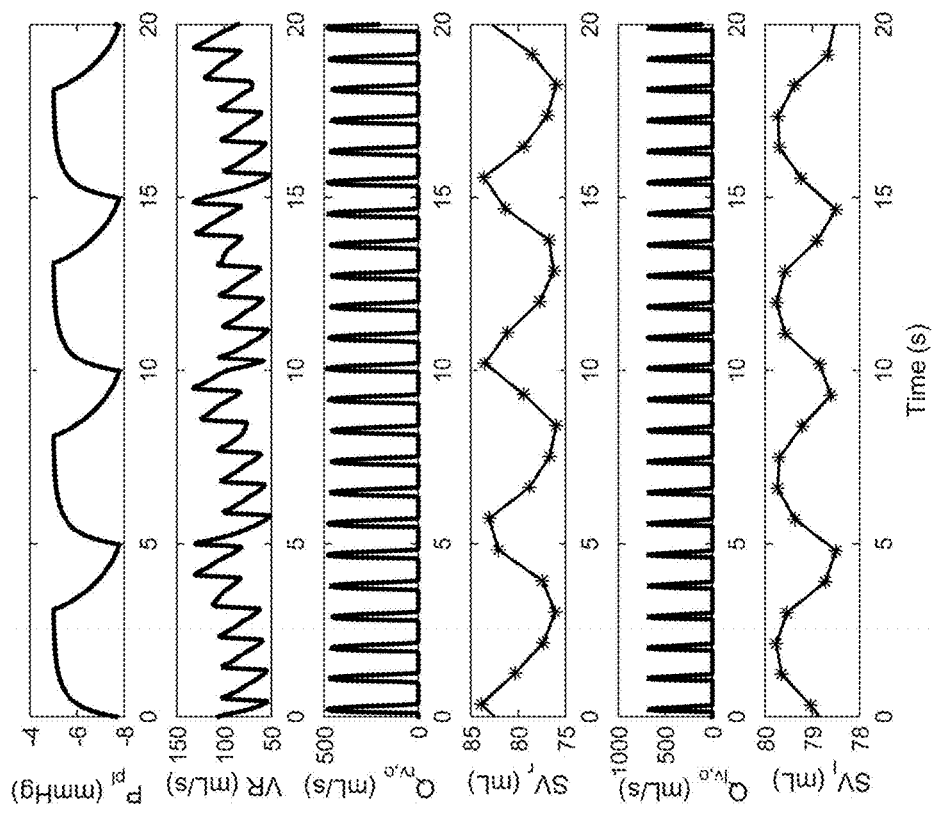
FIG. 5 is a diagram of the time relationships of several cardiac variables.

Heart-Lung Interactions. Important to assessing fluid responsiveness and determination of treatment is a simple understanding of cardiovascular physiology and heart-lung interactions. Albanese et al provide an excellent review. Albanese, Antonio, et al. "An integrated mathematical model of the human cardiopulmonary system: model development." American Journal of Physiology-Heart and Circulatory Physiology 310.7 (2016): H899-H921. on the interactions due to the effects of intrathoracic pressure on venous return and cardiac function. During spontaneous inhalation, venous return increases due to the decreasing intrathoracic pressure that produces a shift in blood volume from the systemic to the pulmonary circulation. Variations in venous return are associated with variations in cardiac performance: the increased venous return during inhalation improves right-ventricular filling and preload, generating an increase in right-ventricular output flow and stroke volume according to the Frank-Starling mechanism. The immediate effects of inspiration on the left ventricle are in the opposite direction: the decreasing intrathoracic pressure affects the pulmonary vasculature, which acts as a capacitance reservoir that holds more blood so that left-ventricular filling is reduced with the consequent drop in left-ventricular output flow and stroke volume via the Frank-Starling mechanism. The immediate effects are reversed during expiration, when intrathoracic pressure returns to baseline. In this case, venous return and right-ventricular output flow are reduced, whereas more blood is forced from the pulmonary vasculature into the left heart, and hence, left-ventricular output flow is increased. The variations of intrathoracic pressure associated with the respiratory events also have effects on systemic arterial pressure. Systolic, diastolic, and pulse arterial pressures are lowest during inspiration and highest at the peak of expiration. These variations result partially from transmission of intrathoracic pressure to the ascending and thoracic aorta and partially from the respiratory-related changes in left-ventricular output flow. FIG. 4 is a schematic representation of the cardiovascular system and shows which elements of the cardiovascular system are resident within the thoracic cavity. Increased intrathoracic pressure, for example, will impact the thoracic veins. It also important to appreciate the close and connected relationships between the right heart, lung and left heart. A change in the right heart propagates through the other two systems. FIG. 5 is a plot of the temporal profiles of venous return, left- and right-ventricular output flow, and stroke volume, along with the intrathoracic pressure (also known as pleural pressure) waveform over few representative respiratory cycles during spontaneous breathing. Helpful in understanding the invention is an appreciation of the phase relationships between intrathoracic pressure (input stimulus) and the stroke volume of the heart with particular focus on the left ventricular stroke volume. As shown in the diagram at 5 seconds, inhalation is maximal as evidenced by the lowest point on the pleural pressure tracing, venous return to the right heart is maximal, stroke volume for the right heart is almost maximal and stroke volume from the left heart is almost minimal. The schematic demonstrates the inverted relationship between the right and left heart as well as the fact that the system has some time delays. As will be described later, the phasic relationships shown in the figure are modified in heart failure and provide a basis for a diagnostic test described later.

Embodiments of the invention provide a method for creating a repeatable perturbation in venous return coupled with a noninvasive measurement system for quantifying the impact of such a perturbation for the purpose of assessing hemodynamic status. The invention relies on a number of physiological mechanisms or relationships. For efficiency and clarity of presentation, important diagrams that explain the physiological transfer functions will be presented first, followed by the specifics regarding the example embodiments. The discussed transfer functions include (1) the relationship between intrathoracic pressure and lung volume, as described by the so-called Campbell diagram (FIG.

Figure 12:
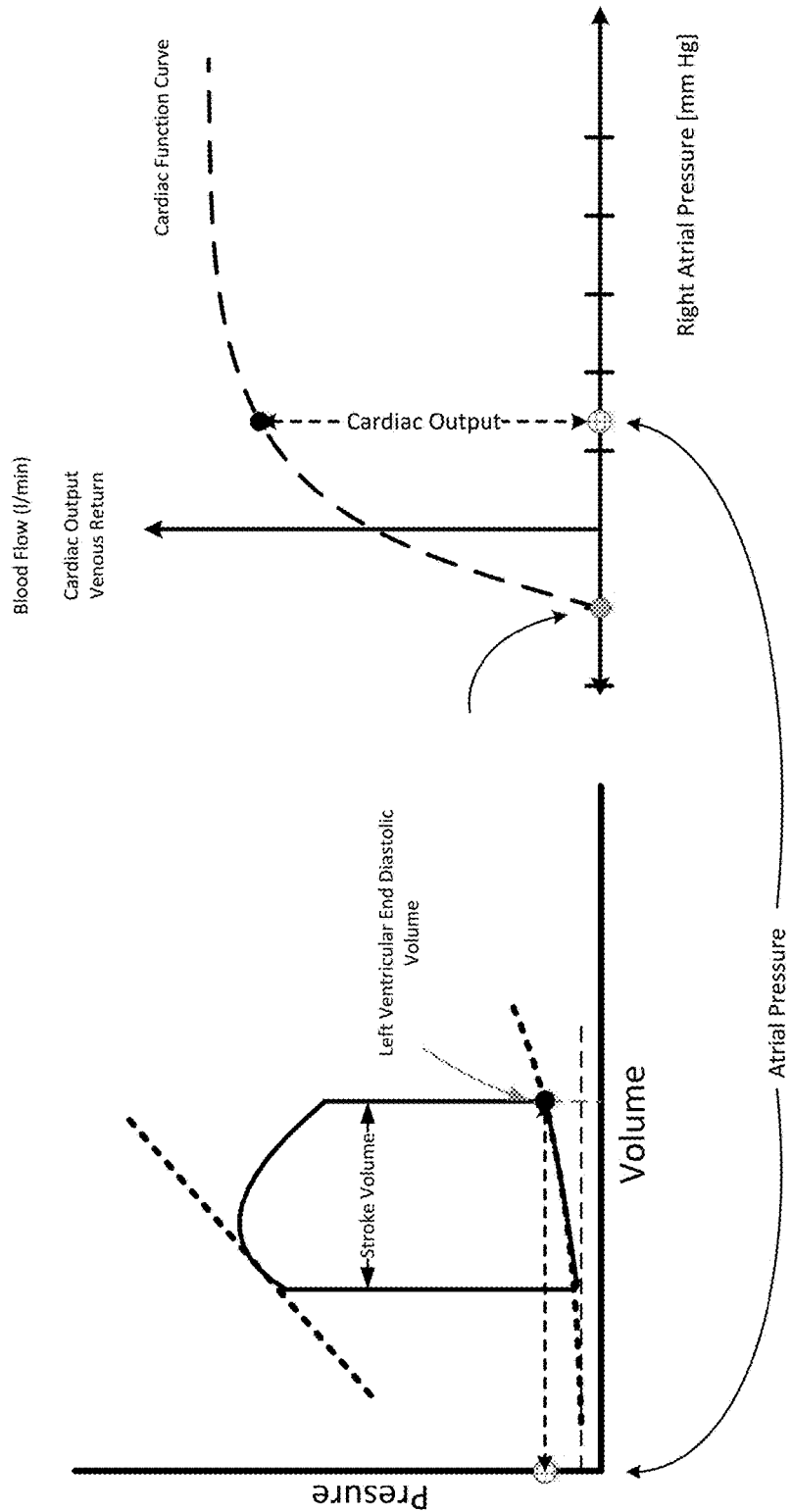
FIG. 12 is a schematic representation showing the relationship between the Frank-Starling curve and the Sagawa pressure volume curve.
Figure 13:
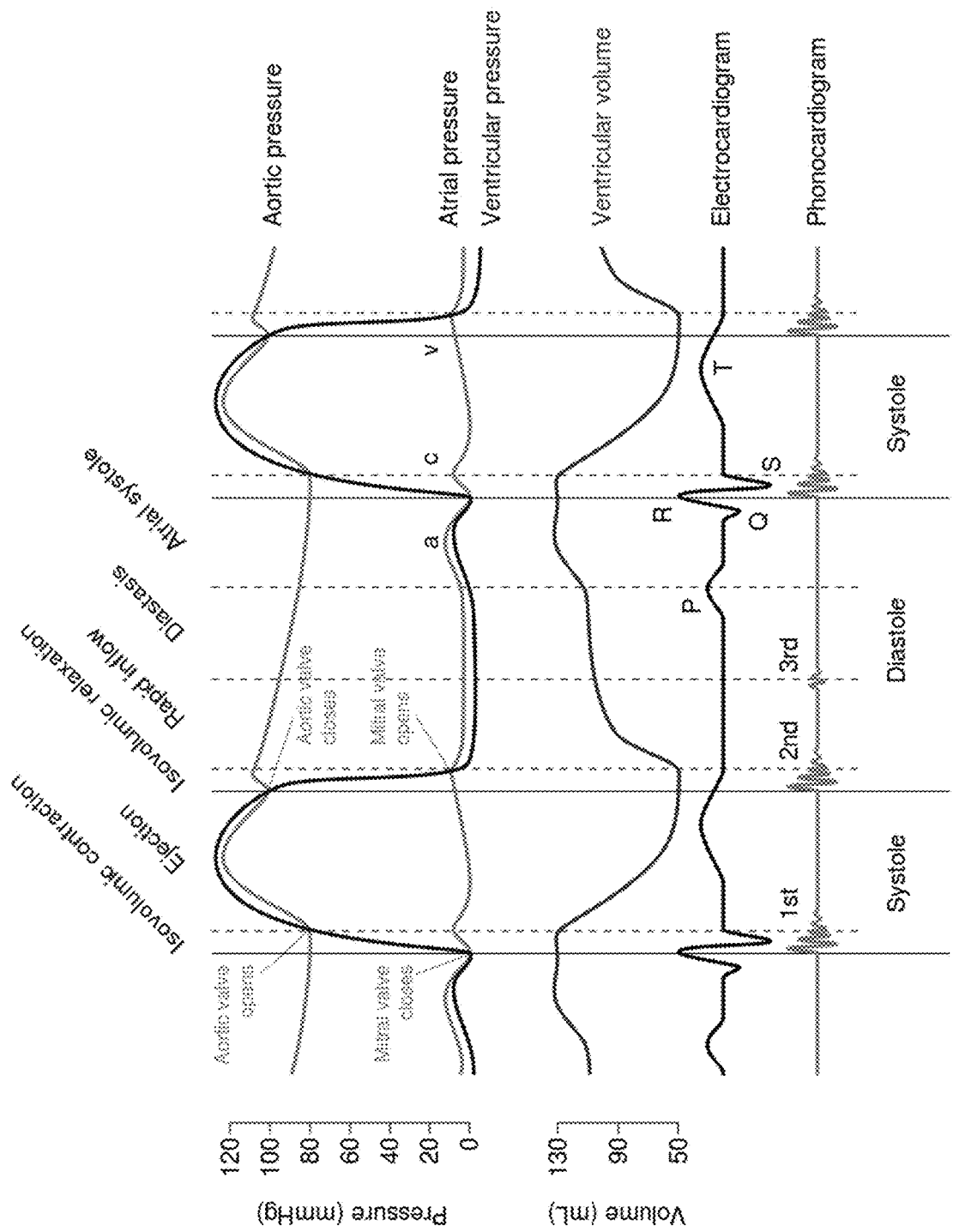
FIG. 13 is a schematic representation of the Wiggers diagram.

6), (2) the effect of intrathoracic pressure on venous return, which is illustrated by the Guyton diagram (FIG. 7, FIG. 8 and FIG. 9), (3) the impact of venous return on heart function via the Frank Starling curve (FIG. 1), (4) the resulting cardiac cycle changes represented on the Sagawa pressure-volume curve (FIG. 11 and FIG. 12), and (5) the transformation of changes in the cardiac cycle into the time domain, as visualized with a Wiggers diagram (FIG. 13). The Wiggers diagram establishes the relationship between key cardiac electro-mechanical intervals and measurable parameters. The measurable parameters are the electrocardiogram (ECG), pulse photoplethysmogram (PPG) and phonocardiogram (PCG). The key elements of these physiological transfer functions are described below.

Figure 6:
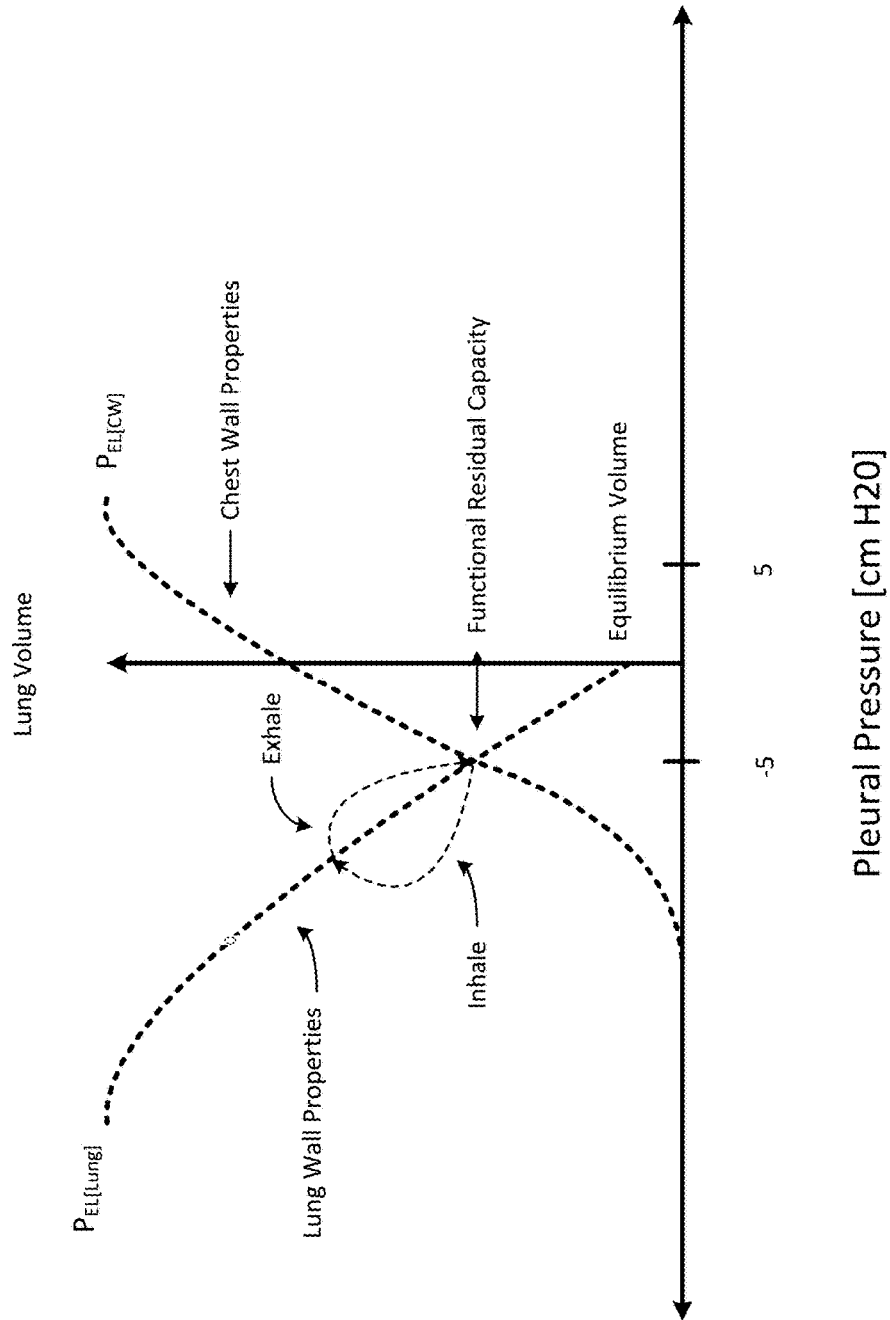
FIG. 6 is a schematic representation of the Campbell diagram.

Campbell Diagram. The Campbell diagram as shown in FIG. 6 is a graphical means of assessing the relationship between intrathoracic pressure (or pleural pressure) and lung volume as a function of airway resistance, lung compliance and chest wall compliance. Lung elastance curve is shown as $P_{EL[lung]}$ and Chest wall elastance is shown as the $P_{EL[CW]}$ curve. The diagram effectively shows both static and dynamic properties of the lung and demonstrates the relationship between changes in pleural pressure and lung volume. Changes in pleural pressure and lung volume are the key mechanical mediators of heart-lung interactions. The diagram also shows a standard respiratory cycle to include inspiration and exhalation. During tidal breathing with normal airway resistance and thoracic compliance, the plural pressure varies between −5 and −10 cm H2O. Functional residual capacity is the volume of air present in the lungs at the end of passive expiration.

Guyton Diagram and Frank-Starling Curve. The work of Guyton is helpful to understanding the invention because it defines in a graphical form the interaction between cardiac function and venous return. For purposes of explanation, the venous return curve will be discussed first followed by the addition of the Frank-Starling cardiac function curve. The discussion will conclude with the representation of different volume states on the Guyton diagram.

Figure 7:
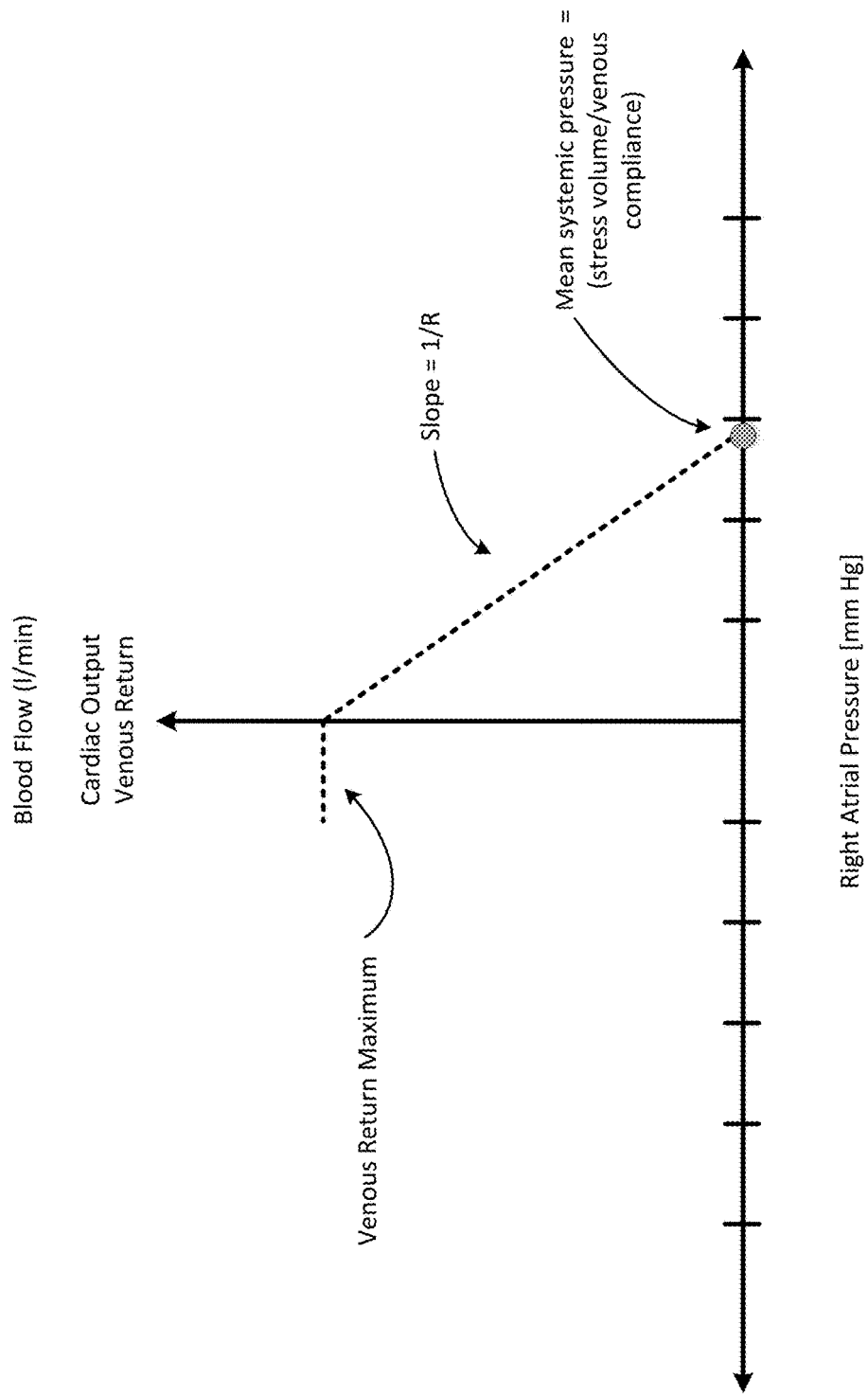
FIG. 7 is a schematic representation of the venous return curve.

Arthur Guyton identified three key determinants of venous return: means systemic filling pressure, venous resistance, and right atrial pressure. The venous return function is graphically represented by placing right atrial pressure on the x-axis, because right atrial pressure is regulated by the function of the heart, and venous flow, which in the steady state is equal to the cardiac output, on the y-axis (FIG. 7). Venous return increases when right atrial pressure decreases. The slope of this relationship is inversely related to vascular resistance: for a given atrial pressure, venous return will increase with a decrease in resistance. When venous flow is zero, the right atrial pressure will equal the mean systemic filing pressure (MSFP) after equilibrium. MSFP is the pressure in the vasculature when venous return is zero and is dependent upon the stressed vascular volume and venous compliance. It is important to note that there is a maximal limit to venous return which occurs when the pressure inside the vessels entering the thorax is less than the pressure outside, this condition limits but does not stop flow because the vessels flutter between opening and closing in what is called a vascular waterfall. Permutt S, Riley S: Hemodynamics of collapsible vessels with tone: the vascular waterfall. J Appl Physiol 1963, 18:924-932.

Figure 2:
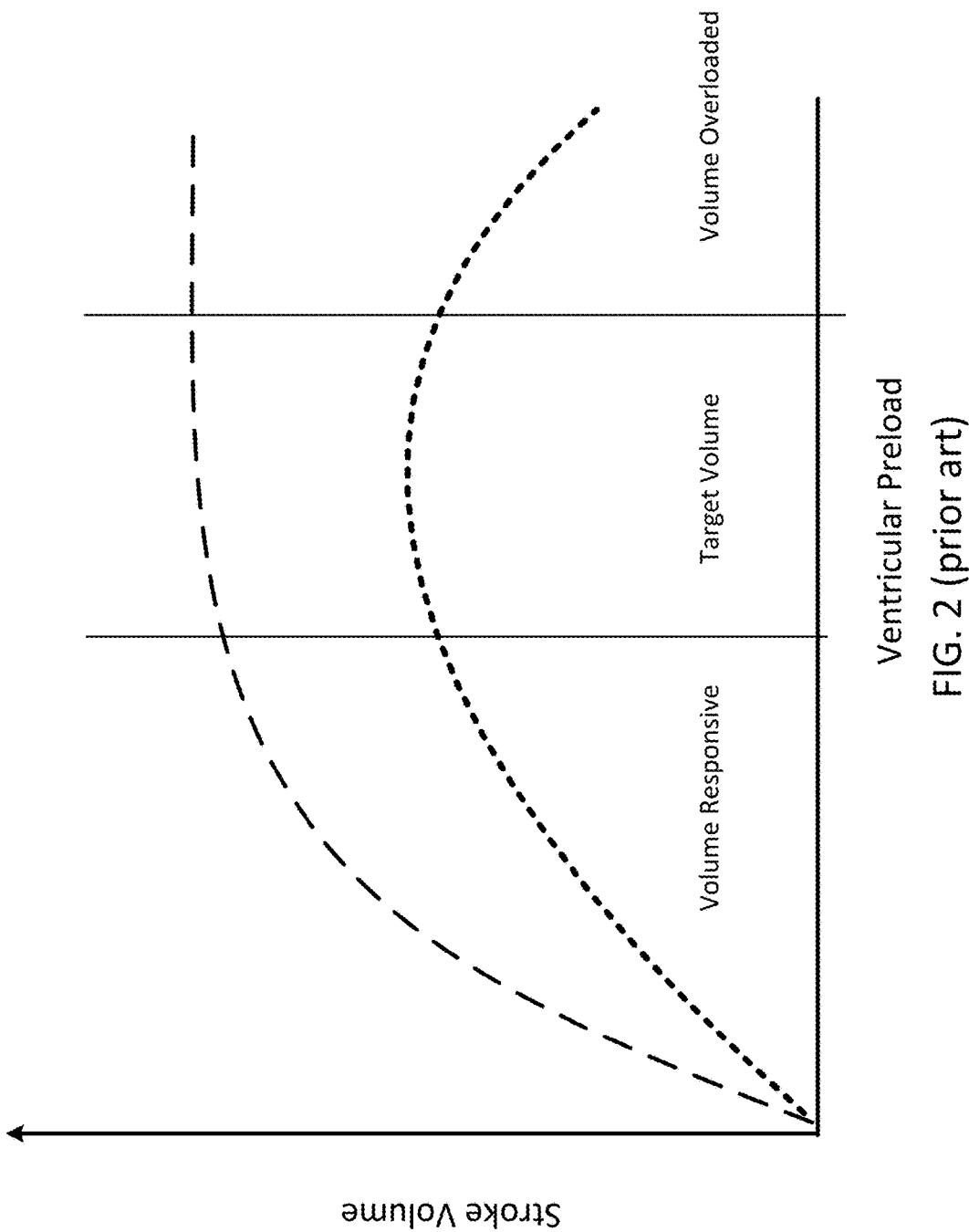
FIG. 2 is a schematic representation of the volume management problem resident in heart failure patients.

The amount of venous return as defined by the Guyton curve has a direct influence of cardiac performance via the Frank-Starling curve. Frank-Starling curves show how changes in ventricular preload lead to changes in stroke volume. The relationship states that the stroke volume of the heart increases in response to an increase in the volume of blood filling the heart (the end diastolic volume) when all other factors remain constant. In other words, as a larger volume of blood flows into the ventricle, the blood will stretch the walls of the heart, causing a greater expansion during diastole, which in turn increases the force of the contraction and thus the quantity of blood that is pumped into the aorta during systole. The increased volume of blood stretches the ventricular wall, causing cardiac muscle to contract more forcefully (the so-called Frank-Starling mechanisms). FIG. 1 and FIG. 2 are example representations of the Frank-Starling curve. The slope of the Frank-Starling is determined by overall cardiac performance.

Figure 8:
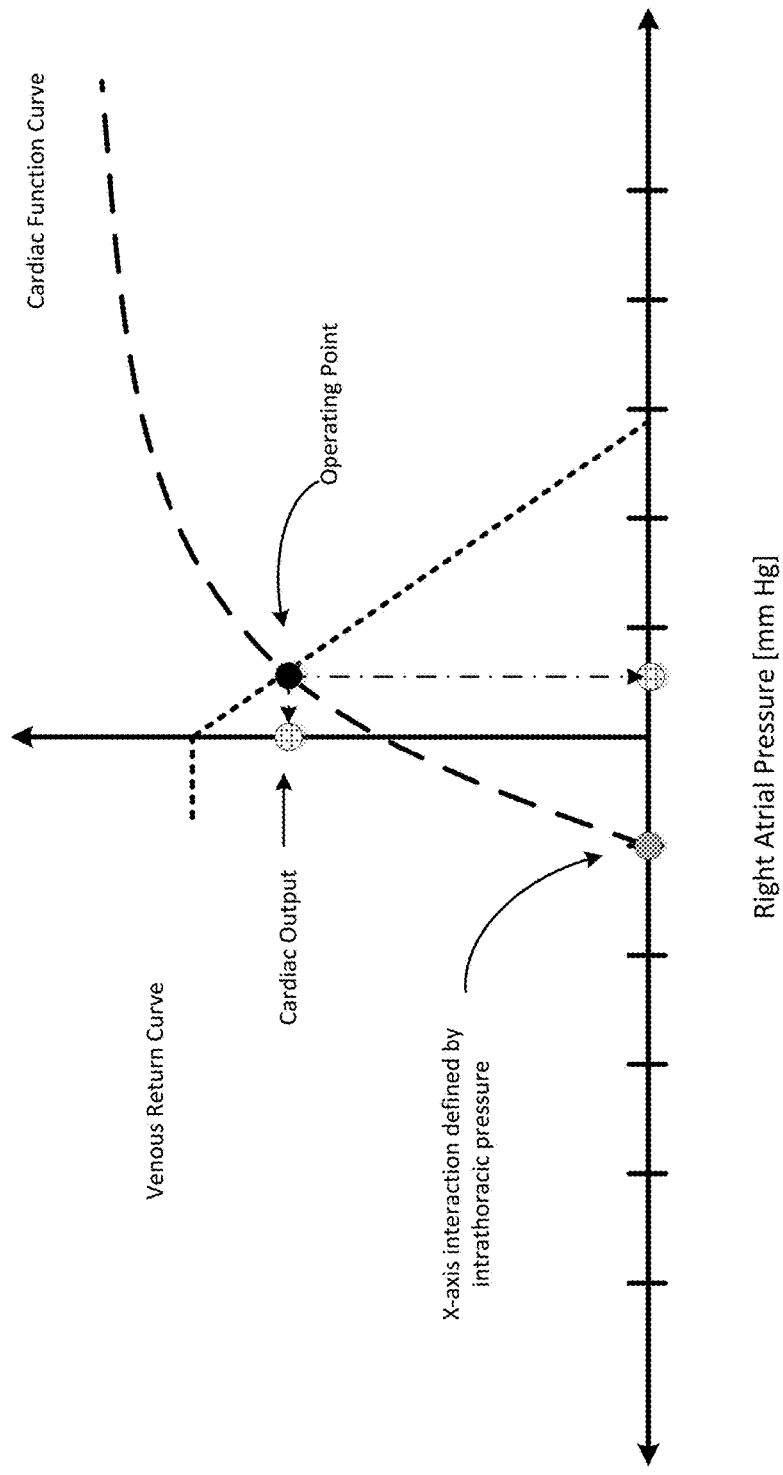
FIG. 8 is a schematic representation of the Guyton Diagram.

FIG. 8 displays the Guyton Diagram with incorporation of the Frank-Starling curve, providing a method of assessing the relationship between right atrial pressure (or central venous pressure) and cardiac output as a function of both venous return and cardiac function. The intersection of the venous return curve and the Frank-Starling curve represents the 'operating point' of the cardiovascular system (black dot). This point defines the central venous pressure and right atrial pressure (cross-hatched dot projected onto the x-axis) and cardiac output (cross-hatched dot projected onto the y-axis) for a given physiological state. The intersection of the Frank-starling curve with the x-axis defines a zero blood flow condition and approximates the intrathoracic pressure (gray dot). This intersection point is important because intrathoracic pressure is a key mediator of overall heart-lung function.

Figure 9:
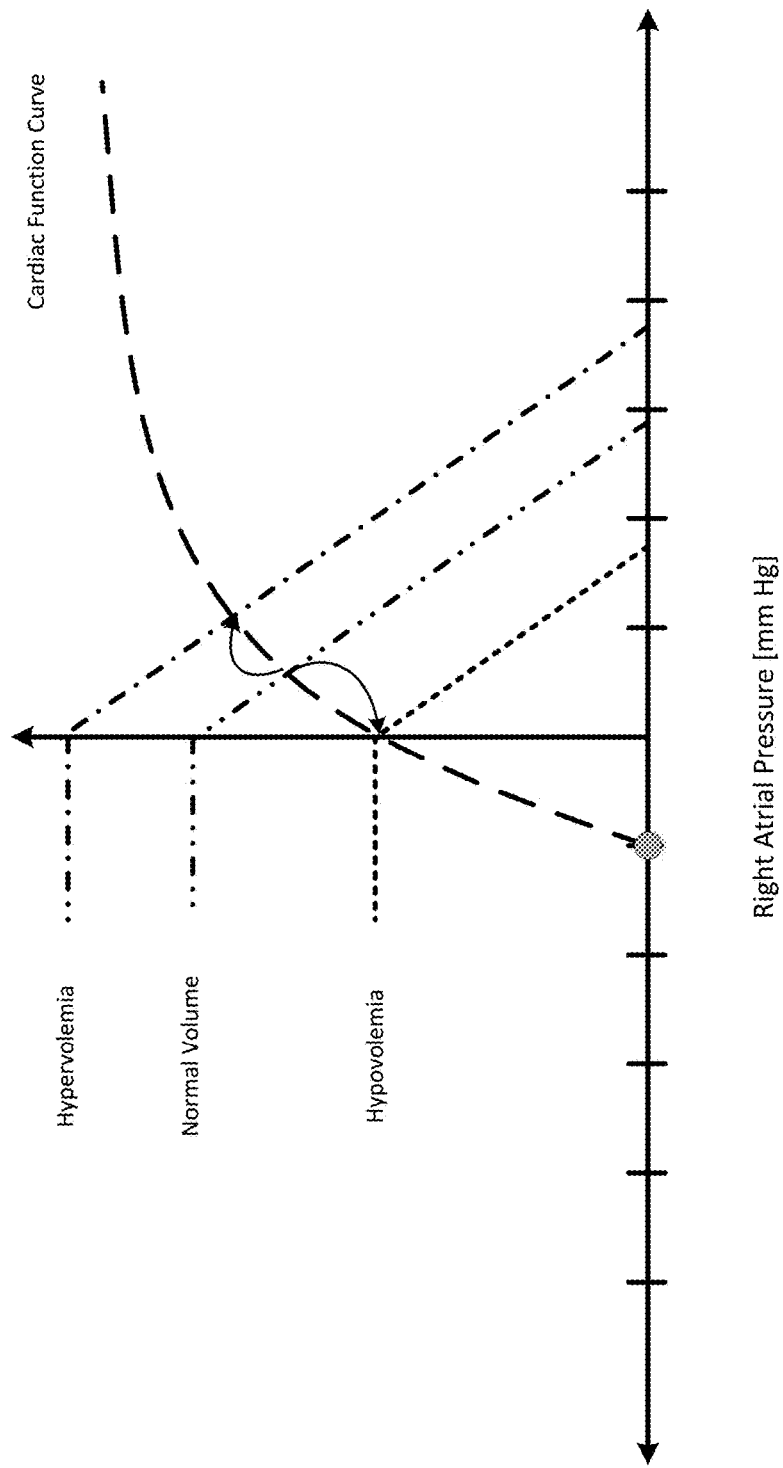
FIG. 9 is a schematic representation of the Guyton Diagram shows different volume conditions.

FIG. 9 shows the influence of volume changes within the context of the Guyton diagram. For example, intravenous fluid administration will increase mean systemic pressure and shift the venous return curve right-wards as shown by the hypervolemia venous return curve. Assuming a normal cardiac function curve, cardiac output increases (fluid responsive patient). Note, as shown, the "subject" is operating on the fluid responsive portion of the Frank-Starling curve. In the case of hypovolemia, the loss of volume will shift the venous return curve to the left. As shown in the figure, the operating point for the cardiovascular system (intersection of venous return and cardiac function curves) exhibits a decreased cardiac output relative to the normal volume condition. Note that further decreases in right atrial pressure will not increase cardiac output as maximal venous return has been obtained and the thoracic veins are starting to collapse. The heart can never pump out more than it receives from the venous reservoir, and the volume the heart receives is limited by venous collapse. The point of venous collapse is directly related to the venous return curve and will occur at different cardiac outputs and shown in the figure.

Figure 10:
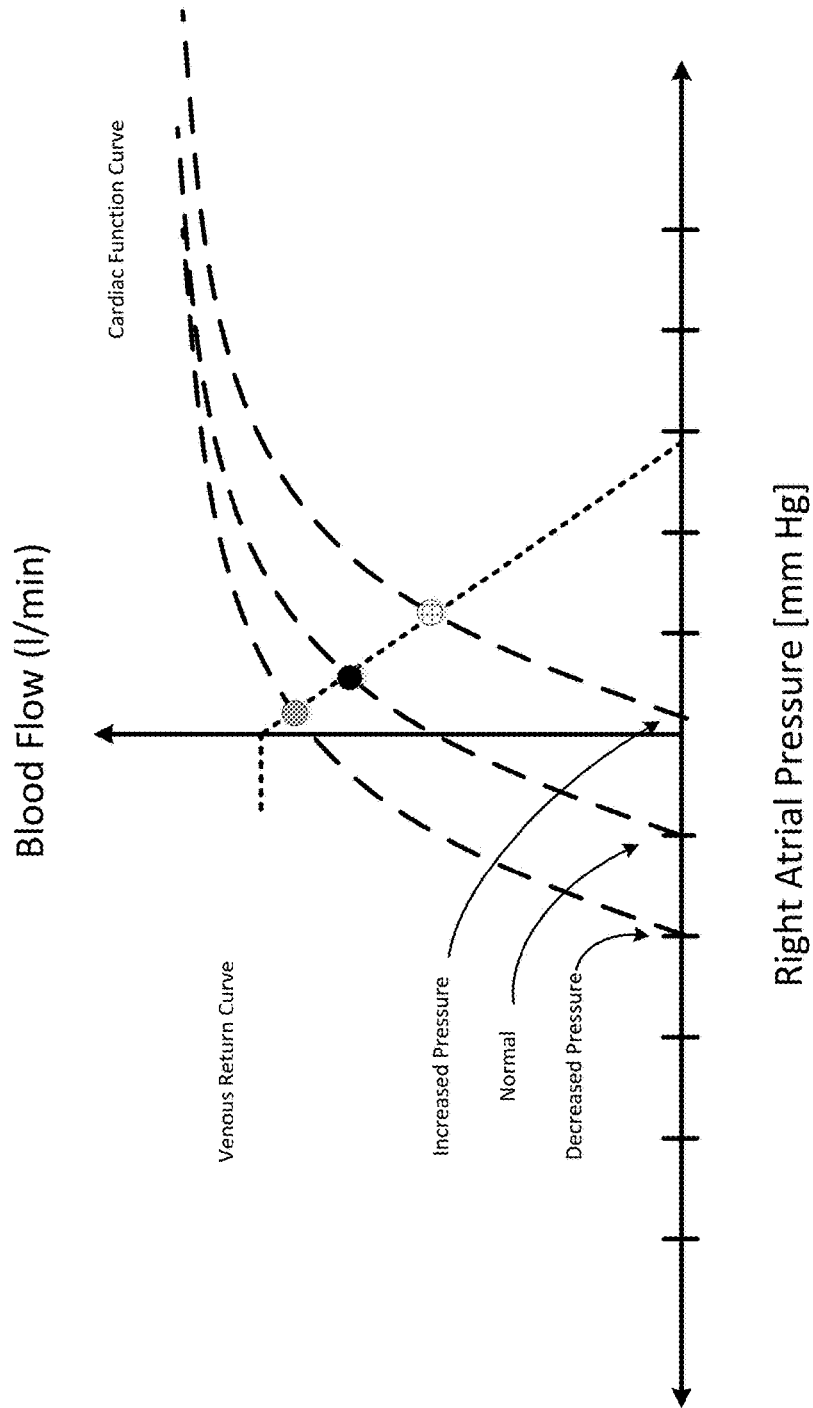
FIG. 10 is a schematic representation of the Guyton Diagram showing intrathoracic pressure changes.

The Guyton diagram can also be used to predict the influence of changes in intrathoracic pressure as shown in FIG. 10. A decrease in intrathoracic pressure due to a large inhale or inhalation against resistance will shift the cardiac function curve to the left, labeled as "Decreased Pressure". This acts as an effective increase in venous return (e.g. like a small fluid bolus) with the arterial pressure change resulting in an increase in cardiac output, see gray circle on figure. An increase in intrathoracic pressure via a Valsalva maneuver (labeled as "Increased Pressure") shifts the cardiac function curve to the right resulting in decreased cardiac output. As evident from the Guyton diagram, changes in intrathoracic pressure have a direct influence on cardiac output and will be leveraged by the invention for the determination of volume status and responsiveness.

The Guyton analysis framework is a powerful tool to understating heart-lung interactions. The nuances of these interactions are exploited in the invention as explained below. The above description has focused on volume status and intrathoracic pressure but analysis can be expanded to explain most aspects of cardiac function. The method explains cardiac performance, including the diastolic function, as it relates to contractility, and afterload of both ventricles, as well as heart rate.

Figure 11:
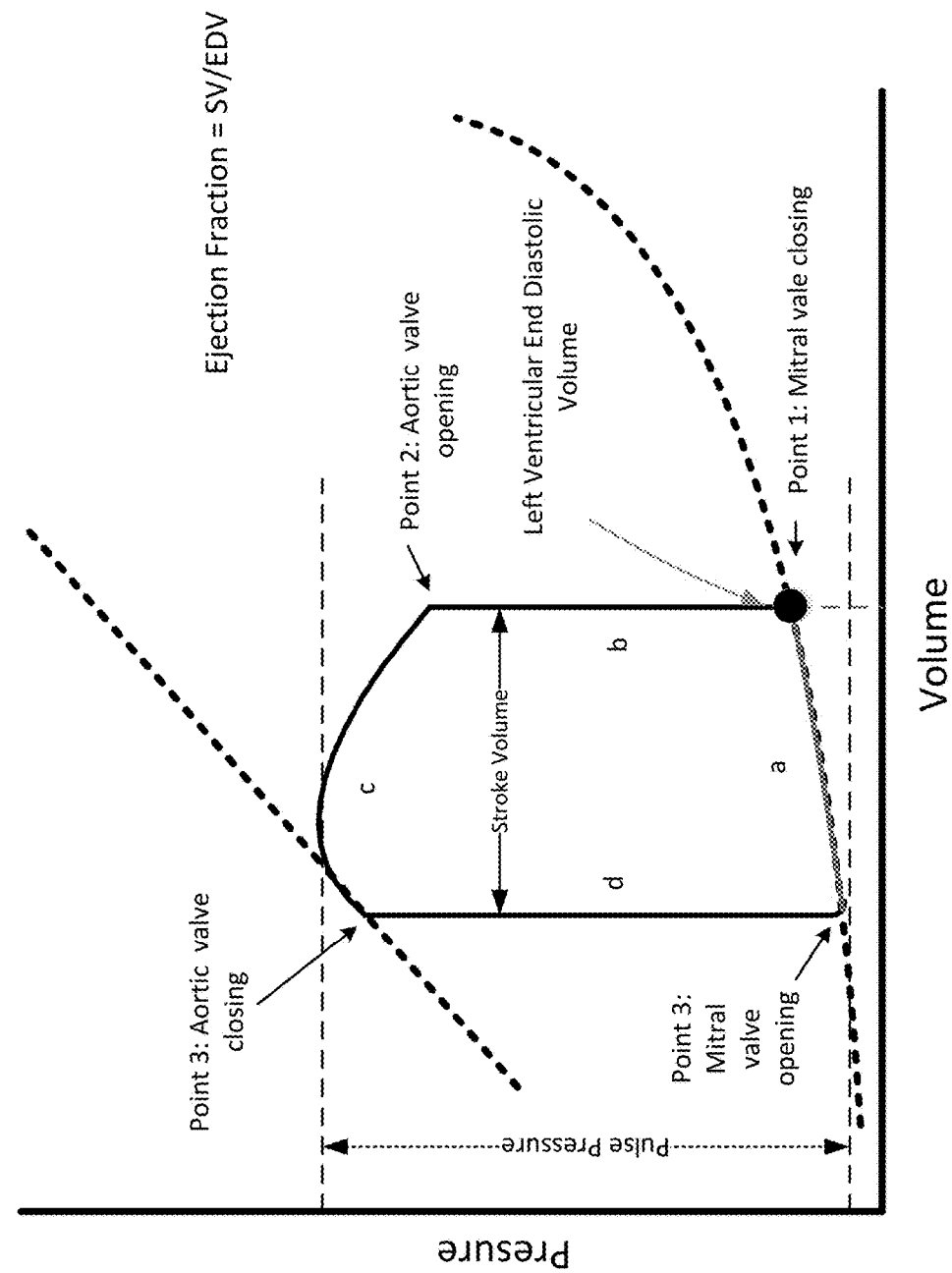
FIG. 11 is a schematic representation of the Sagawa pressure-volume curve.

Sagawa Pressure-Volume Curve. The stroke volume defined by the Frank-Starling curve can be appreciated from an integrated cardiac cycle perspective by examination of the Sagawa pressure-volume curve. Pressure-volume (PV) loops can be developed for both the right and left ventricle but are typically derived for the left ventricle. To generate a pressure volume loop for the left ventricle, the left ventricular pressure (LVP) is plotted against left ventricular (LV) volume at multiple time points during a complete cardiac cycle. When this is done, a PV loop is generated, as shown in FIG. 11. A single cardiac cycle can be divided into four basic phases: ventricular filling (phase a; diastole), isovolumetric contraction (phase b), ejection (phase c), and isovolumetric relaxation (phase d). Point 1 on the PV loop is the pressure and volume at the end of ventricular filling (diastole), and therefore represents the end-diastolic pressure and end-diastolic volume (EDV) for the ventricle. As the ventricle begins to contract isovolumetrically (phase b), the LVP increases but the LV volume remains the same, therefore resulting in a vertical line (all valves are closed). Once LVP exceeds aortic diastolic pressure, the aortic valve opens (point 2) and ejection (phase c) begins. During this phase the LV volume decreases as LVP increases to a peak value (peak systolic pressure) and then decreases as the ventricle begins to relax. When the aortic valve closes (point 3), ejection ceases and the ventricle relaxes isovolumetrically. The LV volume at this time is the end-systolic (i.e., residual) volume (ESV). When the LVP falls below left atrial pressure, the mitral valve opens (point 4) and the ventricle begins to fill. Initially, the LVP continues to fall as the ventricle fills because the ventricle is still relaxing. However, once the ventricle is fully relaxed, the LVP gradually increases as the LV volume increases. The width of the loop represents the difference between EDV and ESV, which is by definition the stroke volume (SV). The relationship between the pressure volume curve and the Frank-Starling curve is shown in FIG. 12. Note the common cardiac filling pressure points and the stroke volume shown in the figure.

Wiggers Diagram. The Wiggers diagram (FIG. 13) depicts events for the left ventricle, left atrium, aorta, aortic valve, mitral valve, electrocardiogram and phonocardiogram. Mitchell, Jamie R., and Jiun-Jr Wang. "Expanding application of the Wiggers diagram to teach cardiovascular physiology." Advances in physiology education 38.2 (2014): 170-175. As it relates to this invention, the Wiggers diagram is a key element in translating the information for the Franks-Starling curve and Pressure-Volume curves into a time dependent framework. Specifically, the isovolumic contraction period shown as phase b in FIG. 11 is now measurable based upon the time interval between electrical activity and heart sounds. The left ventricular ejection period is also measurable based upon heart sounds. These electro-mechanical activities generate a pulse wave as shown in the diagram as aortic pressure. The change in aortic pressure creates a pulse wave that travels to the periphery and can be detected noninvasively with PPG. Changes in preload will by necessity create changes in the electro-mechanical time intervals. For example, an increase in preload will increase the rate of change in left ventricular filling pressure (dP/dt) and thus shorten the isovolumic contraction interval because less time is required for the ventricular pressure to reach the aortic pressure. An increase in preload will also lengthen the left ventricular ejection interval because more time is needed to eject a larger volume of blood from the ventricle.

Figure 14:
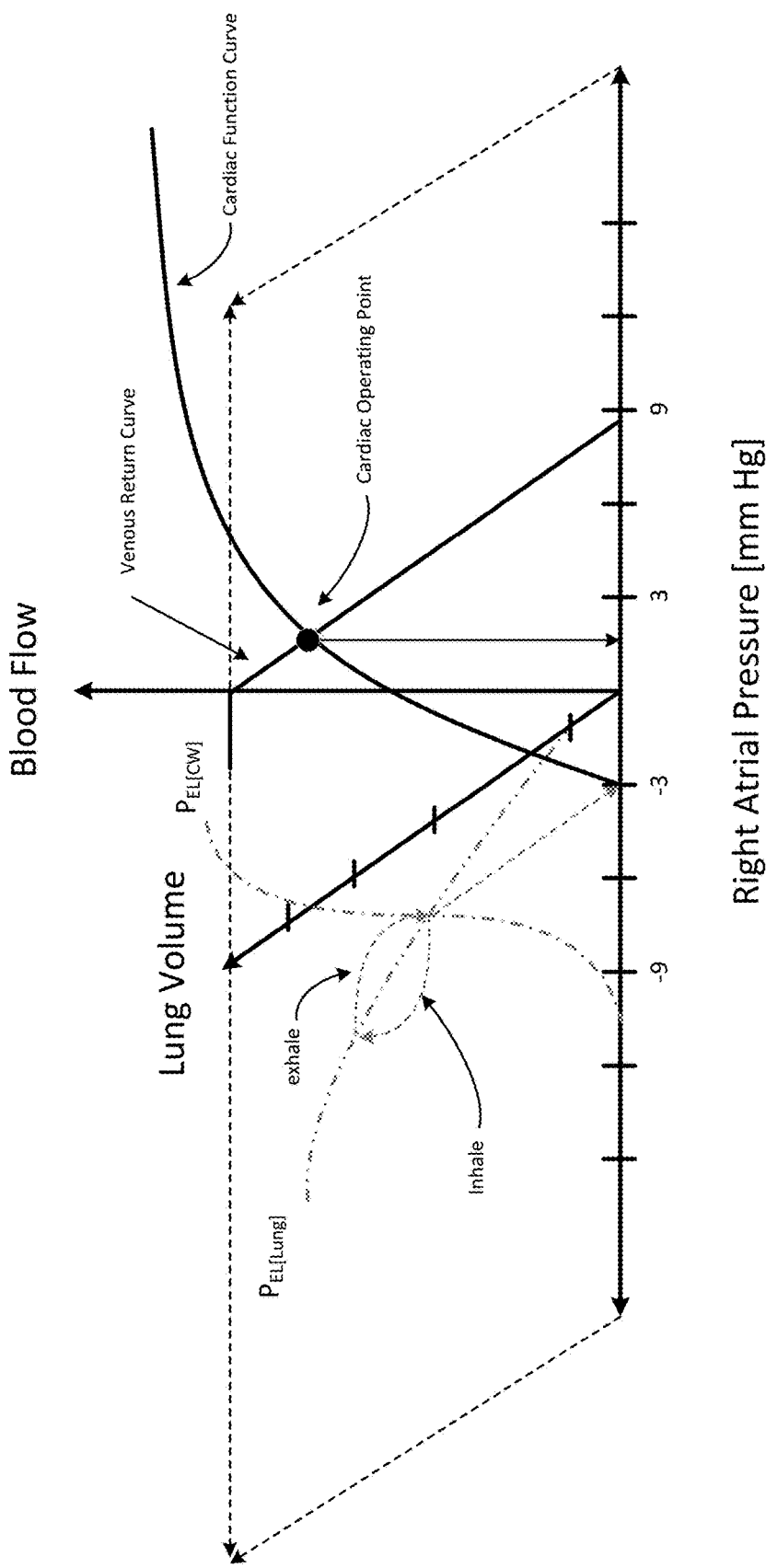
FIG. 14 is a schematic representation of the combined heart-lung interaction diagram in normal volume.

Combined Heart-Lung Interaction Diagram. Although presented as independent diagrams, the Campbell diagram, Guyton diagram and the Frank-Starling curve can be presented simultaneously on a combined graph referred to hereafter as the combined heart-lung interaction graph, see FIG. 14. This graphical representation relates changes of thoracic volume and intrathoracic pressure to alterations in cardiac function and venous return. The diagram communicates that the two most prominent mechanical mediators of heart-lung interaction are changes in thoracic volume and intrathoracic pressure. These are depicted on the Campbell Diagram projected into the page [on the x, z axes]. The elements of the diagram associated with the Campbell diagram are in gray. The Campbell diagram shows a typical inhale with a corresponding exhale. The Guyton Diagram remains on the x, y axes and includes the venous return curve as well as the cardiac function curve. Because the x-intercept of the cardiac function curve assumes intrathoracic pressure, changes in intrathoracic pressure are represented by lateral shifts in the cardiac function curve. The distending pressure or 'trans-mural' pressure of the right atrium is defined by the central venous pressure minus the intrathoracic pressure. The heart-lung interaction diagram will be used to explain several inventive elements of the current invention.

Figure 15:
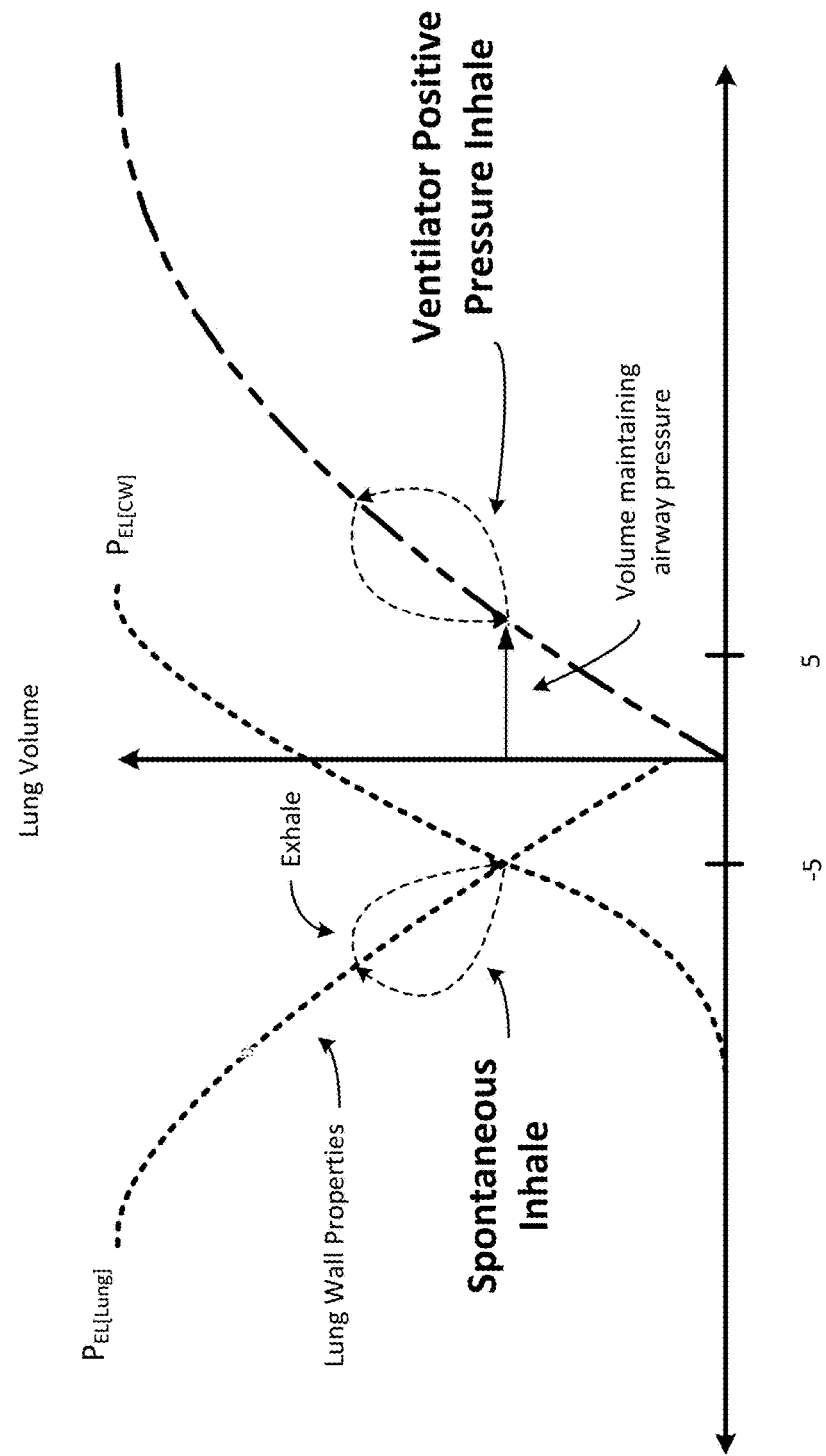
FIG. 15 is a Campbell diagram showing differences in normal breathing versus mechanical ventilation.

Comparison with Mechanical Ventilation. As a final element of background physiology, a comparison between mechanical ventilation and normal breathing is presented in FIG. 15. In normal breathing, inspiration occurs via a decrease in intrathoracic pressure whereas the opposite occurs with mechanical ventilation. Positive pressure and an increase in intrathoracic pressure occurs with mechanical inspiration. The result is a dramatic alteration in intrathoracic pressure and its corresponding influence on venous return. FIG. 15 shows a Campbell diagram showing the differences in pulmonary airway pressure for a general patient on these two types on air exchange. Mechanical ventilation shifts the curve to the right with positive airway pressures. The positive airway pressure is a combination of both static and dynamic pressures. For any given volume of inspiration, there is a portion of the airway pressure invested in the static volume to maintain lung volume while a second portion is associated with dynamic pressures needed for inhale. The relationship between these pressures is dependent on the patient and disease state. Regardless of the static versus dynamic relationship, the peak airway pressure on mechanical ventilation is akin to the pleural pressure during spontaneous breathing, but is positive in mechanical ventilation. Examination of FIG. 15 demonstrates the substantial difference between mechanical ventilation and normal breathing. Re-examination of FIG. 10 enables one to appreciate the influence of mechanical ventilation on venous return, the cardiac function, and venous collapse.

Prior Art Technology Limitations. The methods and apparatuses described herein address deficiencies of prior systems by creating a truly noninvasive system that utilizes a non-ventilated breathing protocol while creating multiple measurement points for improved accuracy, minimizing the influence of tidal volume, and providing the care provider both vascular tone and volume assessment information. To fully appreciate the inventive elements, a review of current technology as well as the prior art is provided Conventional Volume Responsiveness Testing. The literature in the area of predicting fluid responsiveness is significant, but a solid summary is provided in a recent review by Carsetti et al. Carsetti, Andrea, Maurizio Cecconi, and Andrew Rhodes. "Fluid bolus therapy: monitoring and predicting fluid responsiveness." Current opinion in critical care 21.5 (2015): 388-394. Functional hemodynamic monitoring assesses the functional state of the cardiovascular system by measuring a response to a defined stress, typically a change in intrathoracic pressure due to mechanical ventilation. The requirement of a controlled stress is the reason why studies of functional hemodynamic monitoring are linked to patients who were completely passive with the ventilator and receiving relatively high tidal volumes. In the review article by Coudray et al., the authors state that "dynamic indices, however, are valid only when measured in deeply sedated mechanically ventilated patients in sinus rhythm, since they result from heart-lung interaction during well-defined, stable, positive-pressure ventilation cycles. Coudray, Alice, et al. "Fluid responsiveness in spontaneously breathing patients: a review of indexes used in intensive care." CRITICAL CARE MEDICINE-BALTIMORE—33.12 (2005): 2757.

In addition to the above referenced publications, the work of Cavallaro et al. Cavallaro, Fabio, Claudio Sandroni, and Massimo Antonelli. "Functional hemodynamic monitoring and dynamic indices of fluid responsiveness." Minerva anestesiologica 74.4 (2008): 123-135. titled "Functional hemodynamic monitoring and dynamic indices of fluid responsiveness" provides an excellent overview of the actual current technology calculations used for determination of fluid responsiveness. Examination of Table II of this publication shows that the calculations are generally based on minimum and maximum calculation of a defined period of time, typically several respiratory cycles.

Figure 17:
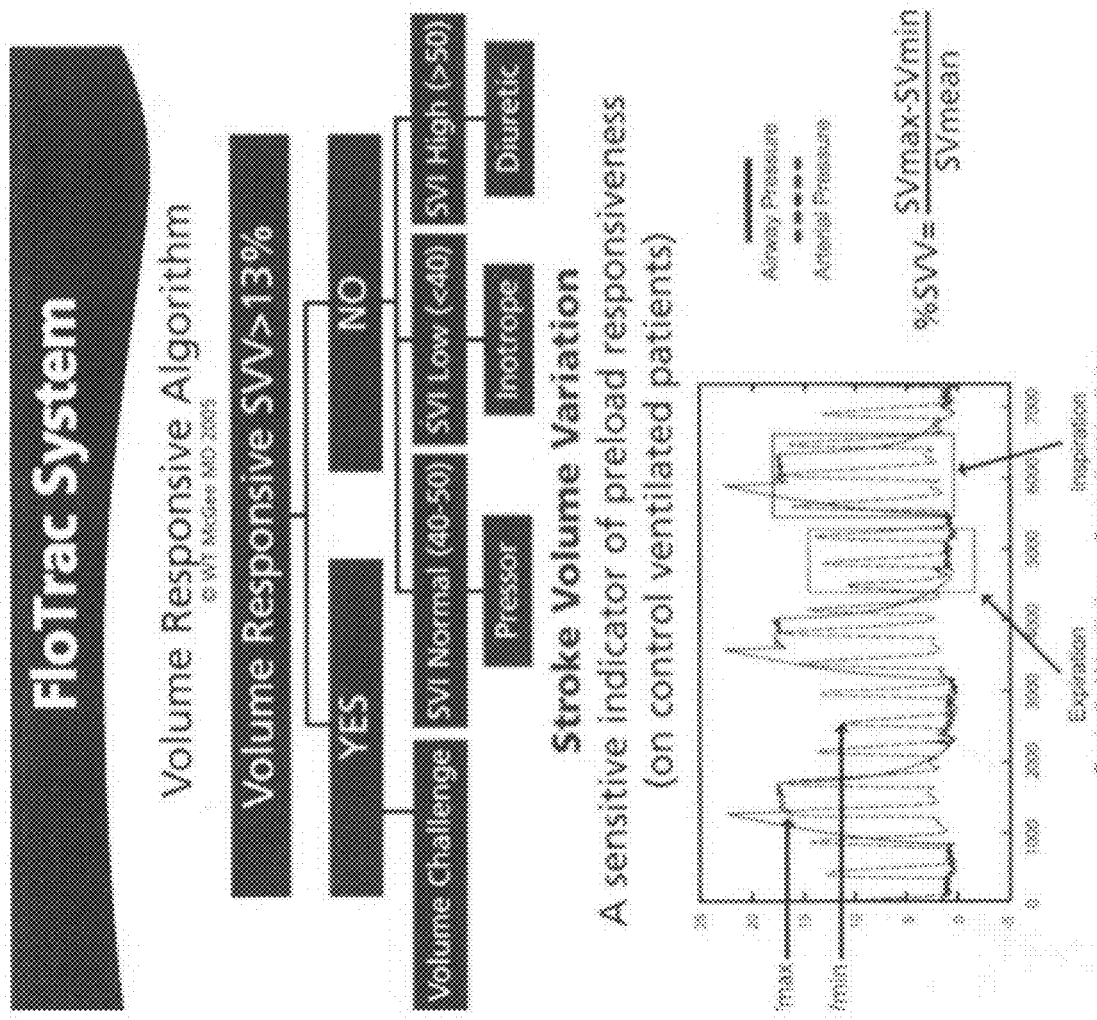
FIG. 17 is a schematic representation of the FloTrac Response Algorithm.

Edward's system. The Edward's Vigileo™/FloTrac™ is a system for volume assessment that satisfies the above criteria and uses a defined stress as it requires an invasive arterial pressure monitoring system and mechanical ventilation. The system utilizes an existing radial or femoral arterial line that is attached to a monitoring unit. Stroke volume is calculated by 3 different variables: arterial pulsatility, resistance, and compliance. Arterial pulsatility is the standard deviation of the pulse pressure and is multiplied by the constant Khi (K) to obtain stroke volume. Note that a pulse pressure magnitude measure can be important to operation of the system. Khi is a compliance and vascular resistance correction factor and is calculated via a multivariate model. Inputs in to the multivariate model include Langewouter's aortic compliance, mean arterial pressure (MAP), variance, skewness, and kurtosis of the arterial pressure curve. Langewouter demonstrated systematic changes in aortic compliance and age, gender, and MAP. By employing and including variables such as compliance and vascular resistance, the monitoring system is able to account for changes in vascular tone. The patient-specific information is employed to account for larger vessel compliance. Pulse pressure is the difference between the systolic and diastolic blood pressure and is comparative to flow. Pulse pressure (arterial pressure) and SV are proportional. Therefore, pulse pressure is incorporated in the algorithm to derive hemodynamic data. Stroke volume variance is then estimated from the arterial waveform with every beat of the heart and stroke volume variance is calculated from the maximum stroke volume value subtracted from the minimum stroke volume value over a specified period of time and then divided by the mean. The resulting variance is then used to as a volume assessment tool to specifically determine fluid responsiveness. FIG. 17 shows how the resulting measurement is used to access volume responsiveness. The Edward's Vigileo™/FloTrac™ is an example of functional hemodynamic monitor that uses a defined stress test by requiring mechanical ventilation, defined tidal volumes, and no spontaneous breathing.

CardioMEMS. The CardioMEMS device is a small wireless sensor that is permanently implanted in the pulmonary artery via a catheter inserted through the femoral vein. The sensor measures pulmonary artery pressure and is paired with a portable electronic transmitter. The system allows patients to wirelessly transmit pressure readings to a secure online database from which treating physicians can access the data. The list price of CardioMEMS is $17,750, which does not include costs associated with surgical implantation or monitoring. The device has demonstrated remarkable clinical efficacy and is included herein to signify both the value of better monitoring for CHF patients as well as the need for less invasive technologies.

Non-Ventilated Patient Investigations in Volume Responsiveness. There has been a long standing desire to determine volume status in patients via spontaneous breathing or more generally in non-ventilated patients. A number of investigators have pursued spontaneous breathing fluid responsiveness determination with varying success and some conflicting results. Although there are a few publications showing positive results the overwhelming consensus is that spontaneous breathing does not work with current processing methods. No existing system can be used on non-ventilated patients. Michael Pinsky, a foremost author and recognized authority in the area of hemodynamic assessment with 48 peer reviewed publication since 2010, published an article devoted to the topic and titled, "Can one predict fluid responsiveness in spontaneously breathing patients?. Pinsky, M. R., Brochard, L., Mancebo, J., & Antonelli, M. (2012). Applied physiology in intensive care medicine 2: Physiological reviews and editorials. Applied Physiology in Intensive Care Medicine 2: Physiological Reviews and Editorials, 1-413. http://doi.org/10.1007/978-3-642-28233-1. Pinsky explains the problems well by stating that historical efforts have failed in non-ventilated patients due to a variety of factors that explain the lack of performance. Spontaneous breathing is associated with variability in tidal volume and associated variances in intrathoracic pressure as shown via the Campbell diagram. Spontaneous inspiratory efforts can increase intra-abdominal pressure because of active compression of abdominal muscles, exaggerating the preload response. Thus, subject-specific breathing variances can influence the measurement results. Additionally, the sudden increases in right ventricular end-diastolic volume can cause a decrease in left ventricular diastolic volume by the process of ventricular interdependence, which cause a decrease in left ventricular stroke volume that is independent of preload-responsiveness. Pinsky also discussed limitation of the standard Valsalva maneuver because the Valsalva maneuver can also affect right and left ventricular afterload, which can contribute to respiratory variations in stroke volume. Buda A J, Pinsky M R, Ingels N B Jr, Daughters G T, Stinson E B, Alderman E L (1979) Effect of intrathoracic pressure on left ventricular performance. N Engl JMed 301:453-459. Pinsky concludes his review of issues by stating "regrettably, $\Delta PP$ and other derived indices cannot be used in spontaneously breathing patients, as slight and sometimes undetected changes in breathing pattern may affect these variables". Thus, a reliable clinical system must address these issues, hereafter referred to as the Pinsky requirements. Prior art will be examined in terms of the Pinsky requirements as well as satisfying the criteria for noninvasive instrumentation. The current invention addresses the Pinsky requirements and is completely noninvasive. The limitations of each investigation are noted.

Muller at al. states that dynamic indices such as arterial pulse pressure or aortic velocities recorded by esophageal Doppler or echocardiography are not valid in spontaneously breathing patients. Muller, L., Bobbia, X., Toumi, M., Louart, G., Molinari, N., Ragonnet, B., . . . Lefrant, J. Y. (2012). Respiratory variations of inferior vena cava diameter to predict fluid responsiveness in spontaneously breathing patients with acute circulatory failure: need for a cautious use. Critical Care, 16(5), R188. http://doi.org/10.1186/cc11672. The authors thus investigated the ability to use inferior vena cava diameter as a metric for fluid responsiveness in spontaneously breathing patients. The investigation used transthoracic echocardiography for vena caval measurements. The results demonstrated an area under the curve of 83% in prediction fluid responders. However, the authors recommend caution as low variations (<40%) of IVC diameter cannot rule out a need for fluid therapy in spontaneously breathing patients with acute circulatory failure.

Heenen at al. investigated the issue in the publication titled, "How can the response to volume expansion in patients with spontaneous respiratory movements be predicted?". Heenen, S., De Backer, D., & Vincent, J.-L. (2006). How can the response to volume expansion in patients with spontaneous respiratory movements be predicted? Crit Care, 10(4), R102. http://doi.org/10.1186/cc4970) The aim of the study was to evaluate the ability of different static and dynamic measurements of preload to predict fluid responsiveness in patients with spontaneous respiratory movements. The study failed to predict the response to volume expansion in spontaneously breathing patients.

The publication by Soubrier at al. Soubrier, S., Saulnier, F., Hubert, H., Delour, P., Lenci, H., Onimus, T., . . . Durocher, A. (2007). Can dynamic indicators help the prediction of fluid responsiveness in spontaneously breathing critically ill patients? Intensive Care Medicine, 33(7), 1117-1124. http://doi.org/10.1007/s00134-007-0644-9. titled "Can dynamic indicators help the prediction of fluid responsiveness in spontaneously breathing critically ill patients?" the authors examine both spontaneous breathing as well as forced expiratory maneuvers in one of the larger studies conducted. The authors designed the forced respiratory maneuver in order to enhance the sensitivity of the indicators. However, the performance during this maneuver was significantly lower than during quiet respiration. The publication concludes that their findings confirm the poor value of clinical signs and/or standard hemodynamic parameters to predict the effects of fluid expansion in spontaneous breathing patients. The results suggest that pulse pressure variation and systolic pressure variation are less effective in predicting fluid responsiveness during spontaneous breathing than in mechanical ventilation. Although Soubrier at al. demonstrated decreased performance with forced exhale, other authors have shown improved results in limited testing. Hong et al. used a breathing protocol in which patients were instructed to take a few breaths that consisted of deep inspiration immediately followed by slow passive expiration. Hong, D. M., Lee, J. M., Seo, J. H., Min, J. J., Jeon, Y., & Bahk, J. H. (2014). Pulse pressure variation to predict fluid responsiveness in spontaneously breathing patients: Tidal vs forced inspiratory breathing. Anaesthesia, 69(7), 717-722. http://doi.org/10.1111/anae.12678. The study utilized an invasive arterial line for determination of pulse pressure variation.

Bronzwaer et al. studied the effect of paced breathing and/or an external respiratory resistance on pulse pressure variance and systolic pressure variance. Bronzwaer, A. S. G. T., Ouweneel, D. M., Stok, W. J., Westerhof, B. E., & Van Lieshout, J. J. (2015). Arterial pressure variation as a biomarker of preload dependency in spontaneously breathing subjects—A proof of principle. PLoS ONE, 10(9). http://doi.org/10.1371/journal.pone.0137364. The study was small with only 10 subjects examined. The study demonstrated increased pulse pressure variance (PPV) and systolic pressure variance (SVV) when using paced breathing with either inspiratory resistance or exhale resistance. The authors conclude, "our data confirmed the lack of predictive value of arterial pressure variations in spontaneously breathing subjects and demonstrated that paced breathing at 6/min in combination with an external respiratory resistance enhanced the magnitude and discriminative value of PPV during progressive central hypovolemia. Manipulation of breathing conditions in the assessment of hypovolemia in non-ventilated subjects is worthy of further study in a perioperative setting." The study does not address subject to subject variance in breathing, specifically differences in inspiration between diaphragmatic versus chest wall expansion. FIG. 2 in the publication shows large inter-subject variances especially for PPV. The publication also used a standard maximal-minimal divided by the average processing method as shown in equation 1 of the publication. Thus, the ventricular interdependence issues noted by Pinsky are not addressed. Although not mentioned by Pinsky, the method is an amplitude based method for PPV variance and will be influenced by changes in blood pressure that can be due to vascular tone and not associated with volume status.

Similar work was conducted by Dahl et al. in anesthetized pigs. Dahl, M. K., Vistisen, S. T., Koefoed-Nielsen, J., & Larsson, A. (2009). Using an expiratory resistor, arterial pulse pressure variations predict fluid responsiveness during spontaneous breathing: an experimental porcine study. Critical Care. London, England, 13(2), R39. http://doi.org/10.1186/cc7760. The results show that arterial pressure variations as measured by catheters placed in the right carotid artery and in the femoral artery can be used to predicted fluid responsiveness in anesthetized pigs. The publication has similar limitations to Bronzwaer but the influence of anesthesia and the use of pigs makes the study hard to translate to ambulatory, awake humans. Also the measurements used for volume assessment were invasively obtained.

Hong et al. in the publication titled, "Pulse pressure variation to predict fluid responsiveness in spontaneously breathing patients: tidal vs forced inspiratory breathing" used a forced inspiratory protocol to identify fluid responders. Subjects were instructed to take a few forced inspiratory breaths, each cycle of which consisted of deep inspiration immediately followed by slow passive expiration. After training, patients were encouraged to perform forced inspiratory breathing for three cycles. The results generated were positive and show the value of an altered breathing process. The protocol and system used do not address the issues defined by Pinsky in terms of a creating a repeatable test as the degree of inspiration is not controlled. The processing was a standard max-min variance method and all measurements were by an invasive catheter. FIG. 2 of the publication shows a limited relationship between pulse pressure variation during forced inspiratory breathing and the change in cardiac index.

Lamia et al. tested whether volume responsiveness can be predicted by the response of stroke volume measured with transthoracic echocardiography to passive leg raising in patients with spontaneous breathing activity. Lamia, B., Ochagavia, A., Monnet, X., Chemla, D., Richard, C., & Teboul, J. L. (2007). Echocardiographic prediction of volume responsiveness in critically ill patients with spontaneously breathing activity. Intensive Care Medicine, 33(7), 1125-1132. http://doi.org/10.1007/s00134-007-0646-7. The results suggest that a passive leg raise is a needed element of the test and demonstrated an overall sensitivity of the 77%.

Lanspa et al. investigated the ability to use dynamic parameters from subjects not receiving mechanical ventilation. Lanspa, M., Grissom, C., Hirshberg, E., Jones, J., & Brown, S. (2013). Applying dynamic parameters to predict hemodynamic response to volume expansion in spontaneously breathing patients with septic shock. Shock, 39(2), 155-160. The authors used transthoracic echocardiography to measure vena cava collapsibility index (VCCI) and aortic velocity variation (AoVV) prior to volume expansion. They also used a pulse contour analysis device via an invasive catheter to measure stroke volume variation (SVV). In spontaneous breathing patients with septic shock the measured parameters were predictive with an area under the curve of 0.83 and 0.92 respectively. The measurement method of a transthoracic echocardiography is not noninvasive but the authors indicate a sensitivity to metrics associated with venous collapse.

Garcia et al. sought to evaluate whether arterial pressure response during a Valsalva maneuver could predict fluid responsiveness in spontaneously breathing patients. Monge Garcia, M. I., Gil Cano, A., & Diaz Monrové, J. C. (2009). Arterial pressure changes during the Valsalva maneuver to predict fluid responsiveness in spontaneously breathing patients. Intensive Care Medicine, 35(1), 77-84. http://doi.org/10.1007/s00134-008-1295-1. The authors concluded that the arterial pressure response during Valsalva predicted fluid responsiveness. The arterial pressure changes during Valsalva were made by an invasive arterial line. All processing is based upon max-min variance assessment. Additionally, the length of the Valsalva at 10 second will be difficult for many patients to perform. The conclusions of Garcia are questioned in an editorial by Rehberg et al. Rehberg, S., Ertmer, C., & Westphal, M. (2009). Valsalva, Valsalva, may you give me a clue, who needs fluids in my ICU? Intensive Care Medicine, 35(1), 7-8. http://doi.org/ 10.1007/s00134-008-294-2.

In the publication by Monett et al. titled "Assessment of Fluid Responsiveness in Spontaneously Breathing Patients" the authors draw two important conclusions. Teboul, J., Lamia, B., & Monnet, X. (n.d.). Assessment of Fluid Responsiveness in Spontaneously Breathing Patients Static Markers of Cardiac Preload as Predictors of Volume, i. First, "Static markers of preload like CVP, RAP, PAOP, RVEDV, LVEDV, and GEDV are not accurate predictors of volume responsiveness in spontaneously breathing patients as they are in patients receiving mechanical ventilation without exhibiting inspiratory efforts." As it relates to dynamic parameters, the authors state, "In spontaneously breathing patients (with or without mechanical ventilation), the prediction of volume responsiveness can be a difficult challenge, in particular in those who have already been resuscitated in the preceding hours or days and in whom continuation of fluid infusion carries risks of pulmonary edema. In these cases, static markers of cardiac preload are generally in the normal range and are rarely helpful for determination of volume responsiveness. Since absolute measures of preload cannot be used effectively to assess volume responsiveness, more dynamic tests need to be employed to improve the utility of these measures. Because of the presence of spontaneous breathing, the indices of volume responsiveness that use heart-lung interactions, such as respiratory variation in arterial pressure and in stroke volume are no longer reliable."

The publication by Vistisen et al. titled "Variations in the pre-ejection period induced by deep breathing do not predict the hemodynamic response to early hemorrhage in healthy volunteers" concluded that in the presence of deep breathing maneuvers that variations in pre-ejection period do not predict cardiac output changes following early hemorrhage. Vistisen, S. T., Juhl-Olsen, P., Frederiksen, C. A., & Kirkegaard, H. (2014). Variations in the pre-ejection period induced by deep breathing do not predict the hemodynamic response to early haemorrhage in healthy volunteers. Journal of Clinical Monitoring and Computing, 28(3), 233-241. http:// doi.org/10.1007/s10877-013-9526-6. Changes in PEP based upon max-min variance assessment. In the discussion, the authors site possible issues with normalization of heart rate, possible problems with the breathing protocol, and the degree of change in the Frank-starling curve. These issues are addressed by the present invention and explained below.

Zollei et al. conducted a study to investigate in spontaneously breathing subjects the changes in hemodynamic parameters during graded central hypovolemia and to test whether slow patterned breathing improved the discriminative value of stroke volume (SV), pulse pressure (PP), and their variations (SVV, PVV). Zöllei, É., Bertalan, V., Németh, A., Csábi, P., László, I., Kaszaki, J., & Rudas, L. (2013). Non-invasive detection of hypovolemia or fluid responsiveness in spontaneously breathing subjects. BMC Anesthesiology, 13(1), 40. http://doi.org/10.1186/1471-2253-13-40. The results of the 20-person healthy subject study showed prediction in ROC analysis relative to stroke volume and stroke volume variance. However, examination of Table 3 shows significant overlap in results between subjects and the stroke volume variance ROC analysis demonstrated only a 75% specificity. Relative to the Pinsky requirements the system and method had no control regarding intrathoracic pressure, no mechanism to compensate for different breathing types, and the results were based upon max-min variance processing.

Investigation into the use of PPG to predict volume responsiveness. The use of PPG as method for determining volume status has been studied by multiple groups. All prior groups have focused on amplitude measures associated with the PPG signal. These efforts are summarized below.

In the publication by Bendjelid K. et al., the authors state that the pulsatile changes in absorption of light between the source and the photodetector of a pulse oximeter create a 'pulse' wave that is assumed to be the result of the beat-to-beat changes in stroke volume transmitted to the peripheral circulation. Bendjelid K. (2008). The pulse oximetry plethysmographic curve revisited. *Current Opinion in Critical Care,* 14(3), 348-353. In this regard, analysis of the respiratory variation in the plethysmographic signal measured from pulse oximetry has been proposed as a technique to assess hemodynamic monitoring.

In the publication by Convertino, V. A. et al., the authors present results on healthy subjects and demonstrate that in their lower body negative pressure test model a non-invasive monitor that provides arterial waveforms coupled with a novel machine-learning algorithm is capable of identifying ongoing loss of central blood volume and thus may predict the point at which individuals will experience hemodynamic decompensation (onset of shock) well in advance of changes in standard or "legacy" vital signs. Convertino, V. A, Moulton, S. L., Grudic, G. Z., Rickards, C. a, Hinojosa-Laborde, C., Gerhardt, R. T., . . . Ryan, K. L. (2011). Use of advanced machine-learning techniques for noninvasive monitoring of hemorrhage. The Journal of Trauma, 71(1 Suppl), S25-S32. The authors point out that additional work is needed to translate these results to "a broad range of actual patients".

In the publication by Lee, Q. Y. v et al., the authors demonstrate the ability to predict stroke volume and systemic vascular resistance by analysis of the PPG signal. Lee, Q. Y., Redmond, S. J., Chan, G. S., Middleton, P. M., Steel, E., Malouf, P., . . . Lovell, N. H. (2013). Estimation of cardiac output and systemic vascular resistance using a multivariate regression model with features selected from the finger photoplethysmogram and routine cardiovascular measurements. *Biomedical Engineering Online*, 12, 19. Predictions were made via a multivariate model using 7 derived features. These features are derived from spectral features at low frequency, mid frequency and high frequency and morphologic features. The morphologic feature was the pulse width. The method does not use pulse transit time or variations in pulse transient time.

In the publication by Marik, P. E. et al., the authors provide a review of various hemodynamic parameters for use in fluid management with significant information on PPG. Marik, P. E., Monnet, X., & Teboul, J.-L. (2011). Hemodynamic parameters to guide fluid therapy. *Annals of Intensive Care*, 1(1), 1. The pulse oximeter plethysmographic waveform differs from the arterial pressure waveform by measuring volume rather than pressure changes in both arterial and venous vessels. As an extension of pulse pressure analysis during mechanical ventilation, dynamic changes in both the peak frequency after an FFT and the amplitude of the pulse oximeter plethysmographic waveform have been used to predict fluid responsiveness. The dynamic changes of the plethysmographic waveform with positive pressure ventilation have shown a significant correlation and good agreement with the pulse pressure variation and have predicted fluid responsiveness in both the operating room and ICU setting. The authors point out that both arrhythmias and spontaneous breathing activity will lead to misinterpretations of the respiratory variations in pulse pressure/stroke volume The publication further states that pulse pressure variation is a reliable predictor of fluid responsiveness only when the tidal volume was at least 8 mL/kg.

In the publication by Middleton, P. M. et al., the authors examined 48 healthy subjects during blood donation and evaluated changes in left ventricular ejection time (LVET) and PTT over the blood donation period. Middleton, P. M., Chan, G. S. H., O'Lone, E., Steel, E., Carroll, R., Celler, B. G., & Lovell, N. H. (2009). Changes in left ventricular ejection time and pulse transit time derived from finger photoplethysmogram and electrocardiogram during moderate hemorrhage. Clinical Physiology and Functional Imaging, 29(3), 163-169. Although terms were observed, the intersubject variation is large. Specifically, the authors state that "a main limitation of using LVETp and PTT as indicators of blood loss is their relatively large inter-subject variations in comparison with the changes induced by blood donation, which means that it is their intra-subject changes rather than their absolute values that are clinically useful, as with most other hemodynamic measurements. In the current study, the use of the absolute values of LVETp and PTT for indication of the lowered central blood volume does not appear to be possible, although the changes in LVETp and PTT over time may still be useful for detecting ongoing blood loss in the initial phase." The inventors have discovered that the inter-subject differences are likely due to breathing differences and other subject dependent issues. The use of a controlled breathing protocol addresses the limitation described by the authors. Also, the authors use a general variance measure versus a respiratory phase measurement.

In the publication by Monnet, X. et al., the authors summarize recent efforts in the use of PPG for volume assessment and provide information on the limitations. Monnet, X., Lamia, B., & Teboul, J.-L. (2005). Pulse oximeter as a sensor of fluid responsiveness: do we have our finger on the best solution? Critical Care (London, England), 9(5), 429-430. The authors state "numerous limitations and pitfalls related to the pulse oximetry method must be highlighted. For technical reasons, the pulse oximetry signal may be of poor quality in the presence of motion, hypothermia or arterial vasoconstriction, although the new generation of pulse oximeters allows one to optimize the recorded signal-to-noise ratio and thus improve the quality of the displayed signal."

In the publication by Moulton, S. L. et al., the authors investigated the ability to calculate a compensatory reserve index based upon hemodynamic parameter including a PPG signal. Moulton, S. L., Mulligan, J., Grudic, G. Z., & Convertino, V. a. (2013). Running on empty? The compensatory reserve index. *The Journal of Trauma and Acute Care Surgery*, 75(6), 1053-9. Testing was conducted via lower body negative pressure tests on healthy subjects. The PPG data was processed via a feature extraction method and evaluated by machine learning techniques. The computer-based methods that underlie the technology were able to tease apart and recognize subtle, beat-to-beat changes within traditional waveform data and predict the compensatory reserve index. The method is based upon PPG data.

In the publication by Pizov, R. et al., the authors conducted a systematic examination of PPG waveforms and their relationship with hypovolemia. Pizov, R., Eden, A., Bystritski, D., Kalina, E., Tamir, A., & Gelman, S. (2010). Arterial and plethysmographic waveform analysis in anesthetized patients with hypovolemia. *Anesthesiology*, 113(1), 83-91. The study examined changes that occurred during autologous hemodilution during surgery. All patients were mechanically ventilated. The paper demonstrated a strong relationship with changes in volume and the delta pulse oximetry plethysmographic waveform amplitude (dPOP). The authors conclude that pulse oximetry ventilator-induced changes in waveform variables are reliable indicators of trends associated with hypovolemia in anesthetized patients. The amplitude of the pulse oximetry plethysmographic waveforms accurately reflected arterial waveforms during more progressive hypovolemia. These results are related to trend characteristics within a single subject experiencing progressive hypovolemia while on mechanical ventilation In the publication by Scully, C. G. et al., the authors present information on the ability to detect blood loss by examining the time-varying spectral amplitude of the photoplethysmographic (PPG) waveform in the heart rate frequency band and/or in the breathing rate frequency band before significant changes occurred in heart rate or arterial blood pressure. Scully, C. G., Selvaraj, N., Romberg, F. W., Wardhan, R., Ryan, J., Florian, J. P., . . . Chon, K. H. (2012). Using time-frequency analysis of the photoplethysmographic waveform to detect the withdrawal of 900 mL of uylood. *Anesthesia and Analgesia*, 115(1), 74-81. The time-frequency spectral method detected blood loss in spontaneously breathing subjects before the onset of significant changes in heart rate or blood pressure. Spectral amplitudes at the heart rate frequency band were found to significantly decrease during blood loss in spontaneously breathing subjects, whereas those at the breathing rate frequency band did not significantly change. Examination of FIG. 3 in the publication shows significant issues with between subject variances.

In the publication by Selvaraj, N. et al., the authors examined the use of amplitude modulation of PPG as an indicator of blood loss when subjects were submitted to a 900 ml blood loss. Selvaraj, N., Scully, C. G., Shelley, K. H., Silverman, D. G., & Chon, K. H. (2011). Early detection of spontaneous blood loss using amplitude modulation of Photoplethysmogram. *Proceedings of the Annual International Conference of the IEEE Engineering in Medicine and Biology Society, EMBS*, 5499-5502. The instantaneous amplitude modulations present in heart rate (AMHR) and breathing rate (AMBR) band frequencies of PPG were extracted from high-resolution time-frequency spectrum. HR and pulse pressure showed no significant changes during the protocol. The AMHR showed decreases between 100 ml through 900 ml blood loss from ear and finger probe sites. The mean percent decrease in AMHR at 900 ml blood loss compared to baseline value was 45.2%, 42.0%, and 42.3% for ear, finger and forehead PPG signals, respectively. In addition, significant increases in AMBR were found due to blood loss in ear and finger PPG signals. Even without baseline AMHR values, 900 ml blood loss detection was shown possible with specificity and sensitivity both 87.5% from ear PPG signals. The technique presented was an amplitude based method.

In the publication by Selvaraj, N., Shelley, K. H., Silverman, D. G., Stachenfeld, N., Galante, N., Florian, J. P., . . . Chon, K. H. (2011). A novel approach using time-frequency analysis of pulse-oximeter data to detect progressive hypovolemia in spontaneously breathing healthy subjects. *IEEE Transactions on Biomedical Engineering*, 58(8), 2272-2279, the methods presented mimic the prior study of Selvaraj et al. but the test subjects were exposed to lower body negative pressure as the mechanism to create hypovolemia. Again the method used for analysis was amplitude modulation.

In the publication by Solem, K. et al., the authors provide results on predicting intradialytic hypotension using PPG data. Solem, K., Olde, B., & Sörnmo, L. (2010). Prediction of intradialytic hypotension using photoplethysmography. *IEEE Transactions on Biomedical Engineering*, 57(7), 1611-1619. The method employs the normalized envelope of the PPG signal, measured at the finger, as an indirect measure of cardiac output and capillary vasoconstriction. A decrease in the envelope of the PPG signal, assumed to reflect capillary vasoconstriction and a decrease in cardiac output, serves as the predictive information for detection of hypotension during dialysis. The method is amplitude based and the results are based upon a small sample group.

In the publication by Solus-Biguenet, H. et al., the authors evaluated the potential predictors of fluid responsiveness obtained during major hepatic surgery. Solus-Biguenet, H., Fleyfel, M., Tavernier, B., Kipnis, E., Onimus, J., Robin, E., . . . Vallet, B. (2006). Non-invasive prediction of fluid responsiveness during major hepatic surgery. *British Journal of Anaesthesia*, 97(6), 808-816. The predictors studied were invasive monitoring of intravascular pressures (radial and pulmonary artery catheter), including direct measurement of respiratory variation in arterial pulse pressure (PPVart), transoesophageal echocardiography (TOE), and non-invasive estimates of PPVart from the infrared photoplethysmography waveform from the Finapres? (PPV-fina) and the pulse oximetry waveform (PPVsat). The PPG signal information did not predict fluid responsiveness in hepatic surgery.

In the publication by Cannesson, M. et al., the authors use changes in pulse oximetry plethysmographic waveform amplitude to predict fluid responsiveness in mechanically ventilated patients. Cannesson, M., Attof, Y., Rosamel, P., Desebbe, O., Joseph, P., Metton, O., . . . Lehot, J.-J. (2007). Respiratory variations in pulse oximetry plethysmographic waveform amplitude to predict fluid responsiveness in the operating room. *Anesthesiology*, 106(6), 1105-1111. The study demonstrated correlation between respiratory variation in the amplitude of the 'pulse' wave (peak-nadir) calculated from variations in the POP waveform (called ΔPOP) and the respiratory variation in arterial pulse pressure recorded with an arterial catheter. The strength of the study is that it takes into account the variation in the amplitude of the pulse wave rather than the peak of the wave. By reflecting the pulsatile changes in absorption of infrared light between the light source and the photo detector of the pulse oximeter, the 'pulse' wave is assumed to be the result of the beat-to-beat changes in stroke volume transmitted to arterial blood.

In the publication by Cannesson, M. et al., the authors examined the ability to use an automatically calculated pulse oximeter plethysmographic waveform amplitude (Delta-POP) to predict fluid responsiveness in mechanically ventilated patients. Cannesson, M., Delannoy, B., Morand, A., Rosamel, P., Attof, Y., Bastien, O., & Lehot, J. J. (2008). Does the pleth variability index indicate the respiratory-induced variation in the plethysmogram and arterial pressure waveforms? *Anesthesia and Analgesia*, 106(4), 1189-1194. The study demonstrated the ability to automatically calculate pulse oximeter plethysmographic waveform amplitude and suggests its value in accessing fluid responsiveness.

In the publication by Convertino, V. A. et al., the authors use the PPG signal to calculate a compensatory reserve index. Convertino, V. a, Grudic, G., Mulligan, J., & Moulton, S. (2013). Estimation of individual-specific progression to impending cardiovascular instability using arterial waveforms. *J Appl Physiol*, 115(8), 1196-202. Testing was limited to healthy individuals with a narrow age distribution. The machine learning approach of the PPG response to central blood volume was able to trend individual specific progression to hemodynamic decomposition.

In the publication by Monge Garcia, M. I. et al., the authors examined the ability to use a Valsalva maneuver to predict fluid responsiveness in spontaneously breathing patients with an invasive radial artery catheter. Monge Garcia, M. I., Gil Cano, A., & Diaz Monrové, J. C. (2009). Arterial pressure changes during the Valsalva maneuver to predict fluid responsiveness in spontaneously breathing patients. *Intensive Care Medicine*, 35(1), 77-84. The study demonstrated that the arterial response during the Valsalva maneuver is a feasible tool for predicting fluid responsiveness in patients without mechanical ventilator support but the measurement was based upon an invasive arterial catheter.

In the publication by Natalini, G. et al., the authors studied mechanically ventilated subjects to compare indices of respiratory-induced variation obtained from direct arterial blood pressure measurement with analogous indices obtained from the plethysmogram measured by the pulse oximeter to assess the value of these indices for predicting the cardiac output increase in response to a fluid challenge. Natalini, G., Rosano, A., Taranto, M., Faggian, B., Vittorielli, E., & Bernardini, A. (2006). Arterial versus plethysmographic dynamic indices to test responsiveness for testing fluid administration in hypotensive patients: A clinical trial. *Anesthesia and Analgesia*, 103(6), 1478-1484. In the population studied, plethysmographic dynamic indices of respiratory-induced variation were just as useful for predicting fluid responsiveness as the analogous indices derived from direct arterial blood pressure measurement.

In the publication by Sandberg, F. et al., the authors provide results on predicting intradialytic hypotension using a PPG signal and ECG signal. Sandberg, F., Hernando, D., Laguna, P., Solem, K., & Technology, I. (2013). Prediction of Intradialytic Hypotension using PPG and ECG, 1227-1230. The method is based upon the examination of PPG amplitude changes. The magnitude of the normalized PPG envelope was used as input data to a test statistic which, when dropping below a fixed threshold, produced a prediction. The method is based upon amplitude changes in the PPG signal.

In the publication by Zimmermann, M. et al., the authors investigated the relationship between invasively determined stroke volume variations during surgery and variations in the pulse oximeter plethysmographic waveform amplitude as evaluated with the noninvasive calculated pleth variability index (PVI). Zimmermann, M., Feibicke, T., Keyl, C., Prasser, C., Moritz, S., Graf, B. M., & Wiesenack, C. (2010). Accuracy of stroke volume variation compared with pleth variability index to predict fluid responsiveness in mechanically ventilated patients undergoing major surgery. *European Journal of Anaesthesiology*, 27(6), 555-561. The PVI was calculated by the Masimo Radical-7 monitor and provides estimation of DPOP. The authors demonstrate that this amplitude based PPG variance showed good agreement with the invasively determined stroke volume variation and both serve as valid indicators of fluid responsiveness in mechanically ventilated patients undergoing major surgery.

Figure 19:
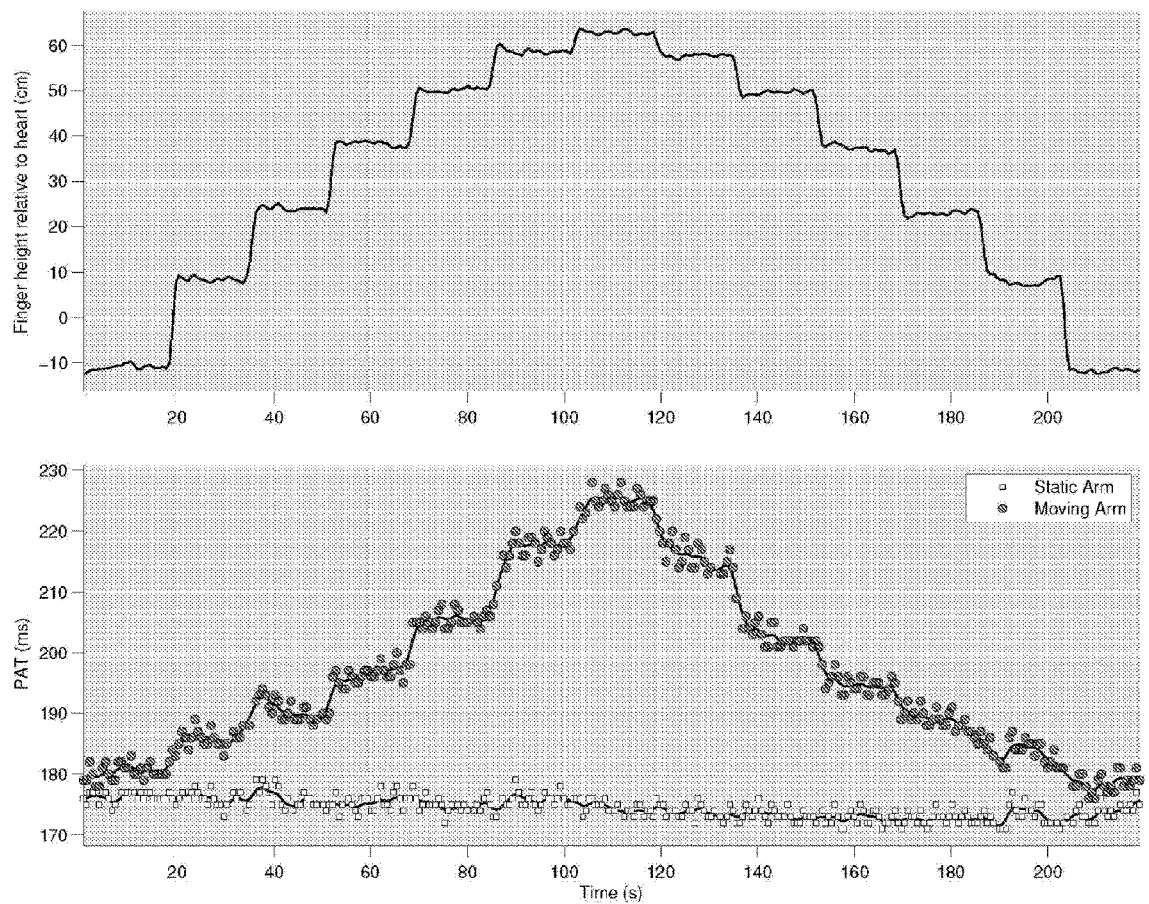
FIG. 19 is a plot of hydrostatic pressure influence on pulse arrival time.
Figure 20:
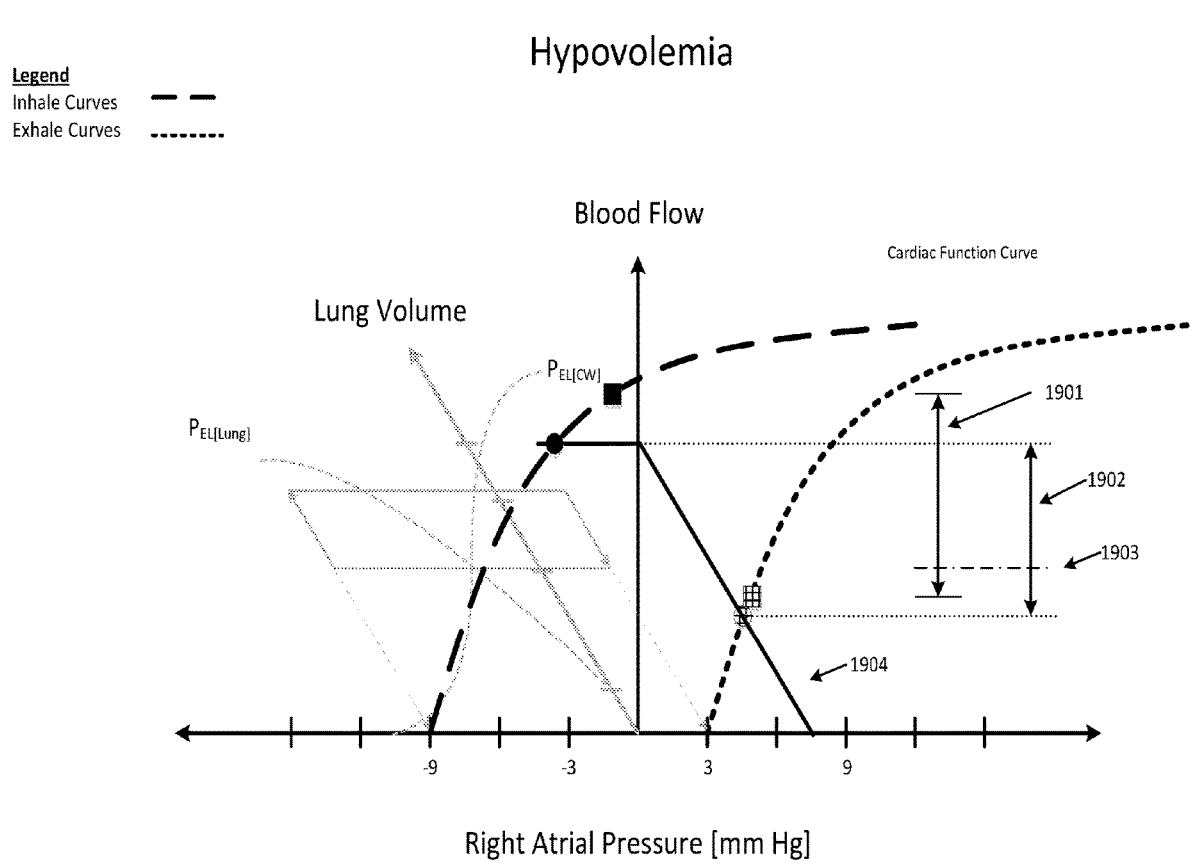
FIG. 20 influence is schematic representation of the combined heart-lung interaction in the presence of hypovolemia.

Sensor Position. Several of the above references use pulse travel times, including pulse arrival time and pulse transit time, to derive diagnostic information. A limitation of prior work has been the inability to determine the position of the finger- or head-based PPG sensors, specifically the sensor's vertical position relative to the heart. Pulse travel times are sensitive to hydrostatic pressure. To illustrate the importance of sensor position, a simple test was conducted. A subject rested in the supine position with both arms flat at the sides. After an initial equilibration period of 5 minutes the subject's left arm was raised up to 90 degrees above the subject's head in increments of 15 degrees, then lowered in the same manner. The arm was held in each position for 15 seconds. The subject's right arm was static, resting at approximately heart level throughout the test. FIG. 19 shows the impact of hydrostatic pressure on pulse arrival times recorded from PPG sensors on the left and right index fingers. Examination of the figure shows stable PAT measurements for the static arm (right arm) while the moving arm (left arm) shows significant changes. The change in PAT is approximately 50 msec over a height change of 70 cm, resulting in a hydrostatic pressure influence of 0.71 msec/cm. Thus, in order for repeatable and comparable pulse transit time measurements to be obtained, the position of the sensor must be measured and or controlled.

Body Pose. Body pose refers to the general position of the body in terms of sitting, standing and laying down (supine) but can include specifics on limb position such a legs raised. The assessment of hemodynamic status is sensitive to body pose due to changes in the distribution of blood. For example, there is a significant difference in the amount of venous that returns to the heart when a patient is placed in Trendelenburg position versus standing. The Trendelenburg position is the placement of the body in the supine position with the feet higher than the head by 15-30 degrees. For repeatable and comparable testing, the body pose of the patient must be measured and or controlled.

Aspects of the Invention. The invention provides methods and apparatuses for the assessment of hemodynamic status. The invention can use an ECG and pulse PPG and/or PCG to estimate parameters associated with vascular tone and stroke volume based upon heart ejection periods, pulse wave velocity, and pulse amplitude. Most parameters utilized in hemodynamic assessment are dynamic parameters and necessitate the use of a perturbation test. The following paragraphs will provide information regarding (1) measurement systems used to obtain physiological data from the patient, (2) how the physiological data can be processed to obtain relevant physiological metrics, (3) what perturbations or observation periods can be used for hemodynamic assessment, and (4) what metrics can be determined and reported to the care provider or patient.

Measurement Systems. The function of the cardiovascular system can be monitored by a variety of methods. Electrocardiography (ECG or EKG*) is the process of recording the electrical activity of the heart over a period of time. Historically, the processes used electrodes placed on the skin, but newer devices no longer use electrodes. The sensors detect the tiny electrical changes on the skin that arise from the heart muscle's electrophysiologic pattern of depolarizing during each heartbeat. Phonocardiography (PCG) is a method of detecting the sounds produced by the heart and blood flow. Similar to auscultation, PCG is most commonly measured noninvasively from the chest with a microphone. Ballistocardiography (BCG) and seismocardiography (SCG) are both methods for studying the mechanical vibrations that coupled to the body and are produced by the cardiovascular system. BCG is a method where the cardiac reaction forces acting on the body are measured. SCG, on the other hand, is a method where the local vibrations of the precordium are measured.

A pulse measurement device is a system that enables the measurement of a pulse due to ejection of blood by the heart. A number of methods and systems can be used and the following is a list of the more common approaches. Photoplethysmography (PPG) is an optical measurement technique that can be used to detect blood volume changes in tissue or has a signal that is related to the cardiac cycle. In addition to the PPG based methods, laser Doppler probes, tonometers and pulse transducers can be used to acquire signals related to the cardiac cycle. Typical pulse transducers use a piezo-electric element to convert force applied to the active surface of the transducer into an electrical analog signal that is related to the cardiac cycle.

Noncontact pulse detection methods have been developed over the past several years and enable pulse determination based upon image analysis. An example of a suitable procedure for remote PPG measure can follow the steps as proposed in McDuet et al. (2014), "Remote Detection of Photoplethysmographic Systolic and Diastolic Peaks Using a Digital Camera". Additional information on the method is available in the article by Li, Xiaobai, et al. "Remote heart rate measurement from face videos under realistic situations" Proceedings of the IEEE Conference on Computer Vision and Pattern Recognition. 2014, which describes a system that can compensate for subject movement and changes in ambient light conditions. These noncontact systems can be used to enhance usability of the system.

Pulse measurement can also be done using the electropneumatic vascular unloading technique based upon the principals originally developed by Czech physiologist Jan Peñáz. The systems measure blood pressure via combined pneumatic pressure system and an optical system. Blood volume changes caused by the pulsation of the blood in the artery (heart activity) are detected by infrared sensors. Counter pressure is exerted from the outside against the finger in such a way that the arterial wall is totally unloaded. This continuously changing outside pressure keeps the arterial blood volume constant all the time and directly corresponds to the arterial pressure. The intra-arterial pressure is therefore measured indirectly. The system represents an alternative method to measuring pulses. The current invention can use a combination of the above to create a unique monitoring system.

Figure 21:
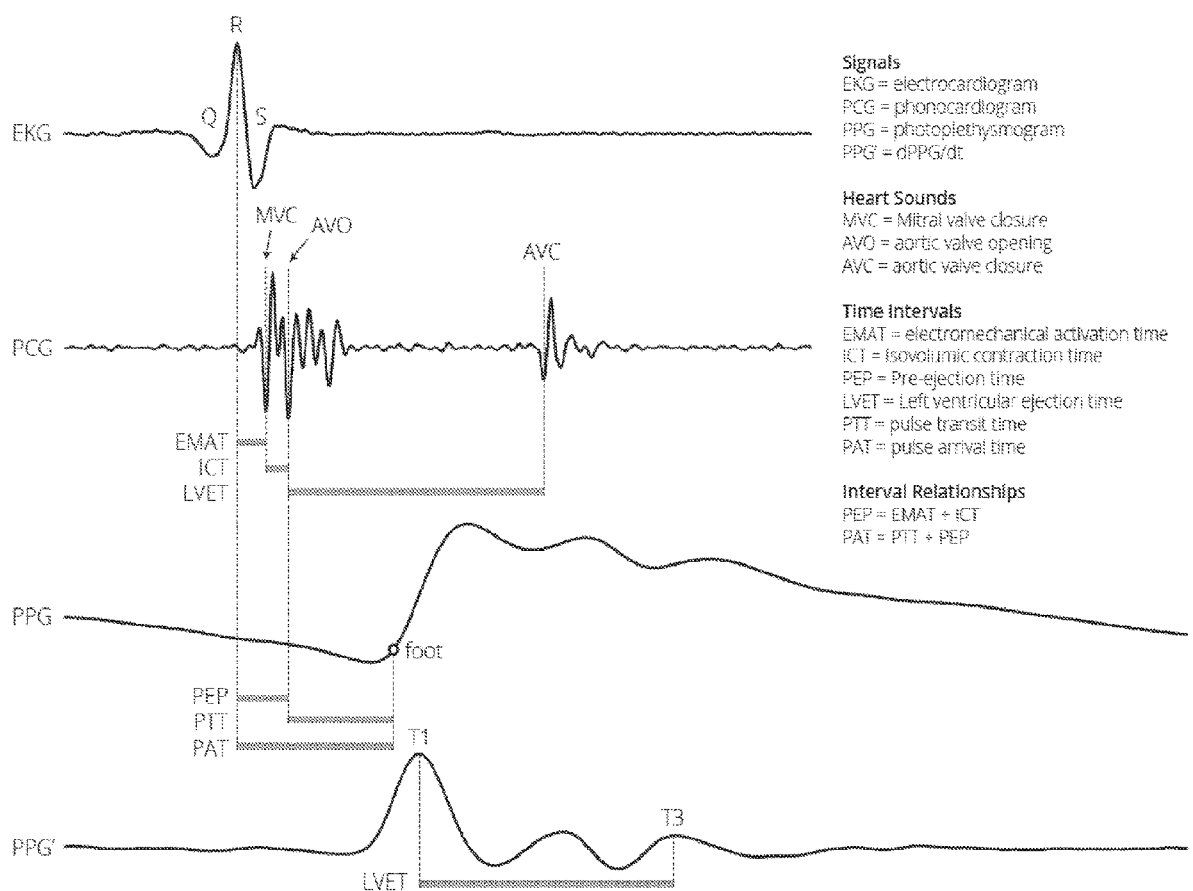
FIG. 21 illustrates the parameters measured by the current invention.

Measured Parameters. FIG. 21 shows the relationships between certain measured parameters and serves a reference for additional terminology.

PAT. The pulse arrival time (PAT) indicates the time from the onset of ventricular depolarization to the arrival of the pulse wave at a peripheral recording site, such as the finger or the forehead. The onset of ventricular depolarization is defined as the first negative deflection (Q wave) in the QRS complex as recorded with an electrocardiogram. However, in practice, this point is often identified as the positive deflection (R peak) in the QRS complex because the R wave is larger and therefore easier to detect. The arrival of the pulse wave in the periphery is measured by PPG and is defined by the "foot" of the wave. Following the method of Gaddum et al., the foot is determined as the intersection between (1) a horizontal projection through a local minimum preceding the wave arrival and (2) a projection through the subsequent local maximal gradient (slope) associated with the pulse wave. Gaddum, N. R., et al. "A technical assessment of pulse wave velocity algorithms applied to non-invasive arterial waveforms." Annals of biomedical engineering 41.12 (2013): 2617-2629. The PAT is decomposed into the pulse travel time (PTT) and pre-ejection period (PEP), according to the following equation: PAT=PTT+PEP. The time intervals PEP and PTT are described below.

PEP. The pre-ejection period (PEP) defines the time interval from the onset of ventricular depolarization to the opening of the aortic valve (i.e., beginning of ventricular ejection). It comprises both the electromechanical activation time (EMAT) and isovolumic contraction time (ICT). The onset of ventricular depolarization is defined as the ECG R wave, as described above, and the opening or the aortic valve is determined from the first heart sound (S1) recorded by PCG. Because aortic valve opening (AVO) lacks a distinct phonological signature in S1, we adopt the method of Paiva et al. and identify AVO using a Bayesian approach. Priors for AVO include (1) a local minimum in the PCG signal during S1, (2) large instantaneous amplitude as determined using the Hilbert Transform, and (3) a Gaussian distribution centered 30 ms after the closure of the mitral valve, which corresponds to the first negative deflection in S1. Paiva, R. P., et al. "Assessing PEP and LVET from heart sounds: algorithms and evaluation." 2009 Annual International Conference of the IEEE Engineering in Medicine and Biology Society. IEEE, 2009. Note from FIG. 21 that PEP may also be defined as PEP=EMS−LVET, where EMS is electromechanical systole (the time interval from ventricular depolarization to the closure of the aortic valve) and LVET is the left ventricular ejection time. This approach is discussed below.

The PEP is a systolic time interval (STI) that allows assessment of ventricular function. As reviewed by Lewis et al., PEP is prolonged when preload decreases and is shortened when preload increases. Lewis, Richard P., et al. "A critical review of the systolic time intervals." Circulation 56.2 (1977): 146-158. Although PEP additionally depends on afterload, and contractility, work by Bendjelid et al. has demonstrated in deeply sedated, mechanically ventilated patients that PEP is predominantly influenced by changes in ventricular preload. Bendjelid, Karim, Peter M. Suter, and Jacques A. Romand. "The respiratory change in preejection period: a new method to predict fluid responsiveness." Journal of Applied Physiology 96.1 (2004): 337-342. Nandi et al. showed that PEP is sensitive to respiration, with a lengthening of PEP during inspiration and a shortening during expiration. Nandi, Priya S., Veronica M. Pigott, and David H. Spodick. "Sequential cardiac responses during the respiratory cycle: patterns of change in systolic intervals." CHEST Journal 63.3 (1973): 380-385. Thus, PEP is a preload-dependent time interval that will lengthen when a fluid responsive subject encounters a preload decrease. As shown by Spodick et al., PEP is largely insensitive to changes in heart rate. Spodick, David H., et al. "Systolic time intervals reconsidered: reevaluation of the preejection period: absence of relation to heart rate." The American journal of cardiology 53.11 (1984): 1667-1670.

LVET. The left ventricular ejection time (LVET) defines the duration of ventricular ejection, i.e., from the aortic valve opening (AVO) to the aortic valve closure (AVC). AVO can be determined from the first heart sound as defined above. AVC is defined as the start of the second heart sound (S2).

Alternatively, the LVET can be determined from PPG pulse waveforms recorded at peripheral sites such as the finger or the ear. As shown by Quarry-Pigott et al., and later by Chan et al., careful analysis of the derivative PPG waveform can identify transition points or peaks that correspond to the opening and closing of the aortic valve. Quarry-Pigott, Veronica, Raul Chirife, and David H. Spodick. "Ejection Time by Ear Densitogram and Its Derivative." Circulation 48.2 (1973): 239-246. Chan, Gregory S H, et al. "Automatic detection of left ventricular ejection time from a finger photoplethysmographic pulse oximetry waveform: comparison with Doppler aortic measurement." *Physiological measurement* 28.4 (2007): 439. In one approach, shown in FIG. 21, LVET is defined as the interval between the first and third peaks in the first derivative of the PPG waveform. In a second approach LVET is defined as the interval between the first and third peaks in the third derivative of the PPF waveform. When LVET can be determined from the PPG, PEP can be computed as PEP=EMS−LVET, where EMS defines the time interval from the ECG R wave to the second heart sound.

The LVET is a second STI that allows assessment of ventricular performance. LVET is strongly affected by preload (and hence stroke volume), with larger stroke volumes lengthening LVET. LVET is also affected by heart rate (HR), with faster heart rates reducing LVET. Weissler et al suggest the use of the left ventricular ejection time index (LVETI), which is computed as LVETI=1.6×HR+LVET, where HR is the heart rate in beats/min. Any hemodynamic assessments based on LVET can also be based on the heart rate corrected index, LVETI.

PTT. The pulse transit time (PTT) indicates the duration required for the pulse wave to propagate through the arterial tree. The PTT begins with the opening of the aortic valve and ejection of blood from the left ventricle, and concludes when the pulse wave foot has reached the peripheral recording site.

PTT is sensitive to the distance (d) traveled by the pulse wave and to the pulse wave velocity (PWV) according to the following equation: PTT=d/PWV. For a single individual and PPG recording site, d is constant. In contrast, PWV will be affected by changes in blood pressure. This is due to the dependence of PWV on arterial compliance and the reduction of arterial compliance at higher distending pressures. In simple terms, a higher blood pressure causes the arteries to become more resistant to stretch, and thus increases the travel velocity of the pulse wave. As shown by Gribbin et al., the relationship between blood pressure and PWV is strongly linear within an individual. Gribbin, Brian, Andrew Steptoe, and Peter Sleight. "Pulse wave velocity as a measure of blood pressure change." Psychophysiology 13.1 (1976): 86-90.

Pulse Amplitude. Pulse amplitude describes the size of the pulse waveform as detected with the PPG. Pulse amplitude can be computed as pulse height, from the foot of the waveform to the peak, or as area under the curve (AUC), the area under the PPG waveform from foot-to-foot. In our experience, AUC can be a more robust measure of pulse amplitude. Over long time periods, changes in pulse amplitude can reflect many factors including vascular tone, body position, and PPG sensor attachment. However, over short time periods (minutes) where body position and vascular tone are relatively constant, the primary factor affecting pulse amplitude is pulse pressure, which is directly influenced by stroke volume.

Pulse Contour. The pulse contour describes the shape of the pulse waveform. The peripheral pulse waveform reflects a summation of the primary wave and secondary waves that arise from various reflections in the vascular tree. Changes in volume status and stroke volume impact the size of reflected waves relative to the primary wave. Thus, pulse contour analysis can be used for hemodynamic assessment. Because the pulse waveform varies in amplitude, frequency, and shape quantification methods vary and include frequency analysis, wavelet transformation, various decomposition methods and curve fitting. An example curve fitting approach uses a mixture of Gaussians which capture the relative timing and amplitude of primary and reflected pulse waves. The resulting model parameters can be used to assess volume status.

Subject Perturbations. As stated previously, dynamic assessment tools have been shown to outperform static measurements for the assessment and management of hemodynamic conditions. In typical applications the perturbation is mechanical ventilation. The current invention does not require mechanical ventilation and is able to obtain clinically relevant information by less invasive perturbations.

Controlled Breathing. Embodiments of the current invention use controlled breathing to create repeatable intrathoracic perturbations. The process does not include mechanical ventilation and is distinguished from common spontaneous breathing in that the breathing activity is volitional. Controlled breathing represents a volitional activity of the patient and includes properties of pace (or rate) as well as pressure. The result is a systematic perturbation that changes intrathoracic pressure in a defined and repeatable manner. The controlled breathing system associated with this invention is differentiated from those represented in the literature by creating a mini-Mueller and mini-Valsalva in a defined manner. Specifically, a pressure change is initially created without a change in lung volume. After a defined pressure is reached, a resistance valve opens allowing for changes in lung volume and exchange of air. The use of a threshold valve that creates a moderately constant pressure despite changes in airflow rate is important. This type of valve is often referred to as a flow-independent pressure valve and helps with the repeatability of the measurement. In contrast, a restrictive valve can be used to create intrathoracic pressure changes but such a valve is dependent upon airflow rate. The pace of controlled breathing can also be important because several of the key measured parameters have time constants or localized measurement periods that occur over several beats.

The value of a controlled breathing process can be well illustrated through use of the Combined Heart-Lung diagram. This process is diagrammed in FIG. 16 with a −6 and +6 mm Hg controlled breathing protocol. Note the "flat" or "box" portion of the Campbell diagram shows the influence of the resistance threshold system. The pressure increases with little change in lung volume until the threshold of the device is obtained. The device then maintains a moderately constant pressure until the exhale or inhale is completed, see 1301 as an example of "flat portion" of inhalation. Note also the large left shift of the cardiac function curve with inhalation, 1302, and the opposite right shift of the cardiac function curve with exhalation, 1303. These changes impact the cardiac operating points as shown in 1304 for inhale and 1305 for exhale. The resulting cardiac operating points cause in a large change in the cardiac output or stroke volume. The change is identified by arrow 1306 which shows the difference in cardiac output between the inhale and exhale. 1307 shows the venous return curve in this schematic. By returning the Guyton venous return curves shown in FIG. 10, one can appreciate how changes in volume status will impact the venous return curve and interact with the entire cardiovascular system.

The above mini-Mueller and mini-Valsalva controlled breathing system can be configured so that pressures are the same on inhalation and exhalation (symmetric) or different on inhalation and exhalation (asymmetric). Note that the resistance pressure can be modified so as to facilitate different defined intrathoracic pressure changes. The resistance pressures can be used to magnify normal changes in intrathoracic pressure leading to larger changes in venous return thus effectively creating an improved signal-to-noise measurement. These larger than normal physiology changes in venous return subsequently create larger changes in stroke volume and facilitate hemodynamic assessment.

Controlled breathing, typically at 6 breaths per minute, can be implemented at zero resistance or at multiple defined levels. A significant benefit of a controlled breathing protocol at different resistance levels is the creation of a moderately consistent breathing process with multiple levels of evaluation. In testing of the system, we have observed that some patients expand their chest while others use a more abdominal breathing mechanism. Kimura et al. demonstrated that changes in inspiration between diaphragmatic versus chest wall expansion influenced inferior vena caval diameter and would thus influence the venous return curve. Kimura, Bruce J., et al. "The effect of breathing manner on inferior vena caval diameter." European Heart Journal-Cardiovascular Imaging 12.2 (2011): 120-123. The invention minimizes the influence of subject breathing type by using information at two different pressure levels to help normalize subject-specific breathing differences. Additionally, as shown in the Campbell diagram previously, changes in lung volume interact with lung and chest wall compliance. Therefore, dramatic changes in tidal volume will have a direct impact on intrathoracic pressure. A benefit of the controlled breathing system is to create repeatable, defined intrathoracic pressure changes where tidal volume differences are minimized.

In summary, embodiments of the invention can utilize a controlled breathing system that creates defined and repeatable intrathoracic pressure changes by utilizing a breathing device that creates mini-Mueller and mini-Valsalva like pressure changes while have the patient breathe at a controlled or defined rate. Physiological parameters can be obtained at multiple pressure setting to facilitate a more accurate dynamic measurement and more completely evaluate the patient's hemodynamic status.

Self-Initiated Positional Changes. In acute circulatory failure, passive leg raising (PLR) is a test that predicts whether cardiac output will increase with volume expansion. By transferring a volume of approximately 300 mL of venous blood from the lower body toward the right heart, PLR mimics a fluid challenge. However, no fluid is infused and the hemodynamic effects are rapidly reversible, thereby avoiding the risks of fluid overload concurrently facilitating moderately constant tidal volume changes. The method for performing PLR is of the utmost importance because it fundamentally affects its hemodynamic effects and reliability. Monnet and Teboul make several recommendations regarding the optimal use of PLR in a clinical setting. Monnet, Xavier, and Jean-Louis Teboul. "Passive leg raising: five rules, not a drop of fluid!" Critical Care 19.1 (2015): 1. In practice, and as illustrated by Monnet and Teboul, the process is implemented via a hospital bed with a mechanical mechanism for movement of the patient. The ability to simulate this define movement without a mechanical bed is almost impossible.

For the purposes of this invention, self-initiated positional changes can be used. The objective is to have the subject execute a maneuver that causes a decrease or increase in venous return in an acceptably repeatable fashion. For example, a significant decrease in venous return can be achieved by have the patient move from the supine position to the seated position to the standing position. The timing of body movements and rate of change can be determined by using inertia measurement unit information or external monitoring systems. An active leg raise process can be used to increase venous return by having a supine patient move the legs from a flat position to raised position, e.g., resting on a chair. Each subject might execute the self-initiated process differently, so a base change in cardiac output can be established and subsequent tests compared to this baseline change. Data on the effectiveness of this simple self-administer test is presented below.

Observation Periods

Embodiments of the invention can also be used to observe trends that occur over time or as result of treatment. For example, the system can examine hemodynamic changes that occur over a dialysis treatment. The dialysis treatment is a defined perturbation to the patient and can be used for hemodynamic assessment. As it relates to management of heart failure, the system can be used to examine the response to diuresis over the course of several days.

Highlighted Elements of the Invention. The invention represents a significant departure from the prior art at least because the invention (1) uses only noninvasive methods to make hemodynamic assessments, (2) uses controlled breathing, (3) exploits the innate asymmetry between inhalation versus exhalation during controlled breathing, (4) capitalizes on response times to different processes during controlled breathing, (5) independently utilizes inhale versus exhale information for respiratory phase processing, and (6) extracts unique information by conducting rapid transition processing. These methods can be applied to data obtained at two perturbation levels via the controlled breathing tests. The utility of the above methods has been demonstrated on real data and the limitations of the existing methods demonstrated.

As noted above, the prior art functional monitoring systems are based upon the fact that peak systolic pressure and arterial pulse pressure are directly related to left ventricular stroke volume and can be used at surrogates of left ventricular stroke volume variance during mechanical ventilation. The processing methods are based upon variance changes or magnitude variances without regard for the phase of the respiratory cycle. Additionally, pulse pressure variation is a more sensitive and specific marker of fluid responsiveness than systolic pressure variation although both are used for hemodynamic assessment.

Inhale-exhale asymmetry. An advantage of the present invention becomes apparent with an awareness that while mechanical ventilation changes are largely symmetric due to the use of positive pressure ventilation, spontaneous or volitional breathing can be highly asymmetric due to limitations in venous return due to vena cava collapse. FIG. 15 in the section on the Campbell comparison between mechanical versus normal breathing shows the magnitude of different in intrathoracic pressure. Examination of FIG. 9 illustrates, that inspiration due to decreased lower intrathoracic pressure can result in venous collapse especially under hypovolemic conditions. Amoore et al. explain that venous return is significantly altered by pressure gradients for blood flow into the thorax resulting from respiratory variations in intrathoracic and intra-abdominal pressures. Amoore, John N., and William P. Santamore. "Venous collapse and the respiratory variability in systemic venous return." Cardiovascular research 28.4 (1994): 472-479. The respiratory pressure variations affect venous flow through their effect on the collapse of the great veins. The great veins are not rigid, but collapse when their extramural pressure exceeds their intra-luminal pressure. When evaluating transmural pressure, care must be taken to examine the pressure gradient across the vessel wall. The thin venous walls offer little resistance collapse with the venous cross-section changing from circular to elliptical and finally to the shape of a figure eight. The presence of venous collapse creates a plateau on venous return to the right atrium.

Once the threshold for venous collapse has been surpassed, additional decreases in intrathoracic pressure have no influence. The differences between mechanical ventilation and spontaneous or volitional breathing are well articulated in the paper by Boson et al. Bodson, Laurent, and Antoine Vieillard-Baron. "Respiratory variation in inferior vena cava diameter: surrogate of central venous pressure or parameter of fluid responsiveness? Let the physiology reply." Critical Care16.6 (2012): 1. The authors state that in mechanically ventilated patients, the objective of studying the inferior vena cava (IVC) is to assess its ability to dilate during tidal ventilation, when intrathoracic pressure is increasing more than abdominal pressure. This dilation actually reflects the ability of the IVC to receive more volume (preload reserve). In spontaneously breathing patients, the situation is completely different. Now, the objective of studying the inferior vena cava is not to evaluate its ability to dilate but its ability to collapse in response to a decrease in intrathoracic pressure and an increase in abdominal pressure. As one can appreciate, the influence of venous collapse during controlled breathing with decreased intrathoracic pressure is markedly different with mechanical breathing due to increased intrathoracic pressure. This asymmetry necessitates a different approach to processing cardiac function variations.

Physiological Time Response Differences. A second important element is to appreciate the time response of key measurement variables. As noted before, position changes or resistance breathing initially influence the right heart, but the system largely measures changes experienced by the left heart. Some changes in right heart function are immediately observable and have a very fast time response while others occur over the course of several beats. Changes that result from ventricular interdependence occur rapidly. Ventricular interdependence is the term used to describe the influence one ventricle on the secondary ventricle via the interventricular septum. The left (LV) and right ventricles (RV) are enclosed in a stiff envelope, the pericardium. They have similar end-diastolic volumes, and there is no free space for acute ventricular dilatation within a normal pericardial space. Thus, when RV end-diastolic volume increases it can only occur at the expense of the space devoted to the left ventricle. Thus, changes in the right ventricle are immediately reflected in the left ventricle. Therefore, the physiological response time due to changes resulting from ventricular interdependence is very fast.

Figure 18:
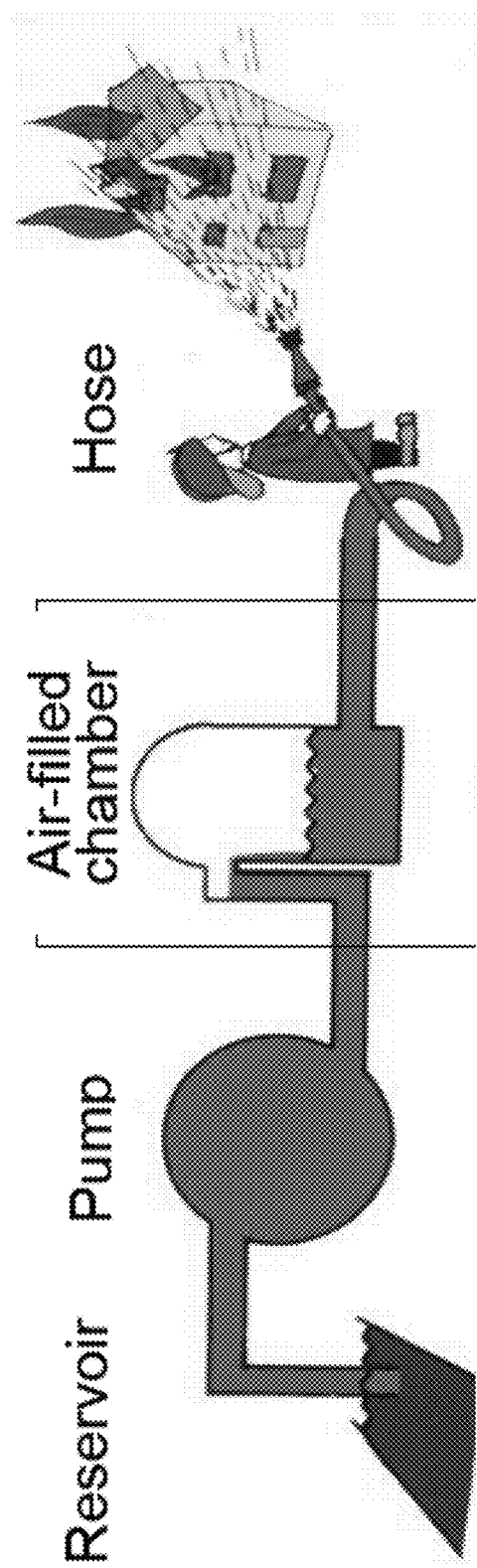
FIG. 18 is a diagram of a Windkessel fire engine.

Changes in left heart stroke volume and pulse pressure have a slower response. Marik et al. note that the "inspiratory reduction in RV ejection during mechanical ventilation leads to a decrease in LV filling after a phase lag of two or three heart beats because of the long blood pulmonary transit time." Marik, Paul E. "Hemodynamic parameters to guide fluid therapy." Transfusion Alternatives in Transfusion Medicine 11.3 (2010): 102-112. A fuller account of the physiology causing the slower response time was described in the 1970s by Niccolass Westerhoff with the Windkessel model, which describes the hemodynamics of the arterial system in terms of resistance and compliance. The basic theory was based upon the Windkessel fire engine, see FIG. 18. As it relates to pulmonary blood flow, blood from the right heart enters the lung, a fluid-air chamber with a high degree of compliance. In the case of increased thoracic pressure, the air and compliance of the lung in combination with the tricuspid value combine to create a moderately constant flow. The result is a damped response to right heart changes. The Windkessel effect of the lung can be best observed in a standard Valsalva maneuver as described in detail later. These changes will have a longer time constant and this difference in timing can be significant when processing the measured signals.

Figure 16:
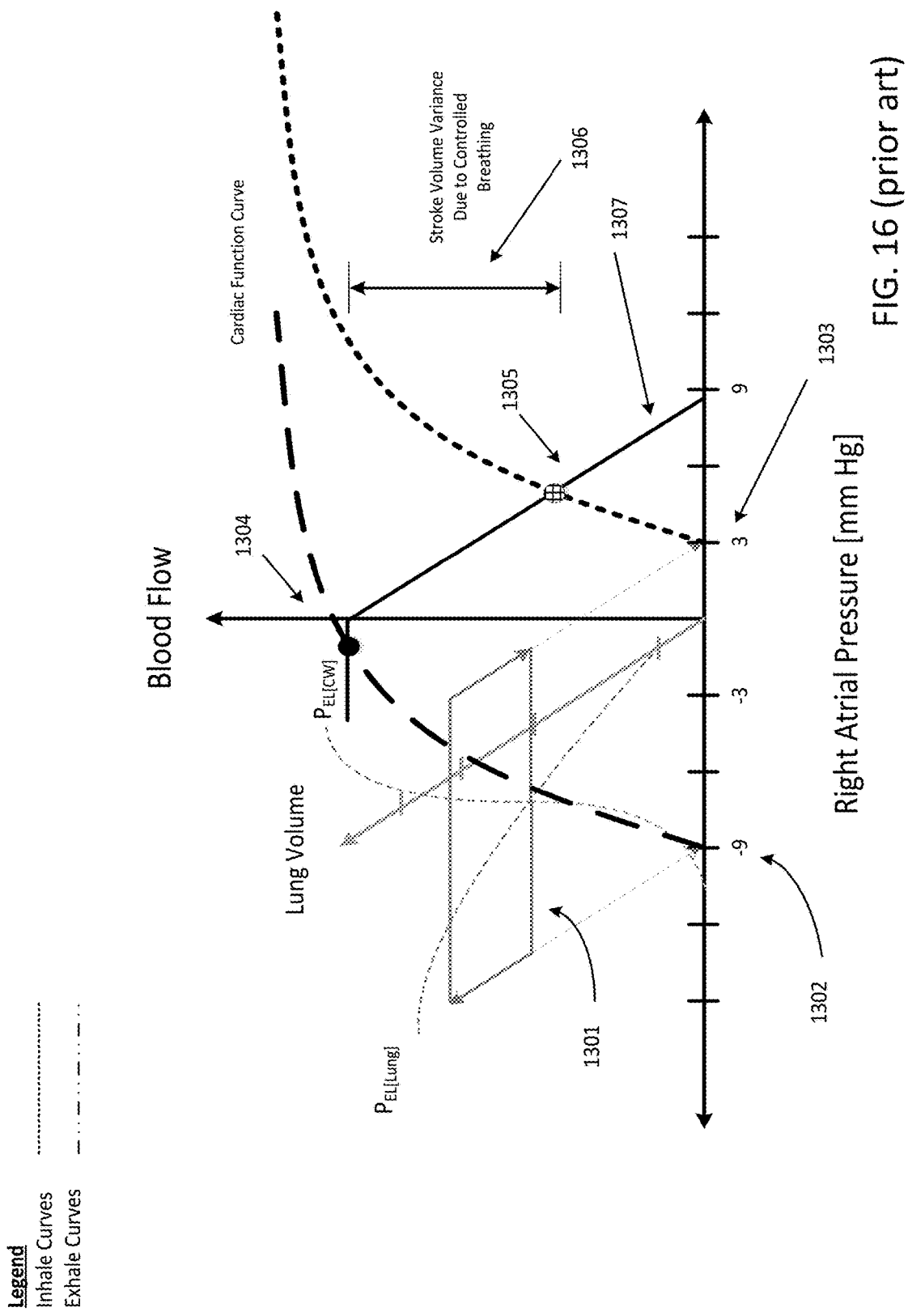
FIG. 16 is a diagram showing the mini-Mueller and Mini-Valsalva aspects of the breathing device.

Respiratory Phase Processing. FIG. 19 demonstrates that changes in stroke volume due to controlled breathing with symmetrical controlled pressure differences will result in an asymmetric cardiac output change as the patient moves from normal volume to hypovolemia. The small squares on the chart are from FIG. 16, representing normal volume conditions. The stroke volume changes for FIG. 16 are shown as arrow 1901. Line 1903 represents the cardiac output point at functional residual capacity or after exhale. Relative to FIG. 16, the venous return curve 1904 has been shifted left to represent a condition of decreased volume. The resting impact of this change is shown via the circular dots. The solid circle is the operating point during inhale and the cross hatched circle is the operating point during inhale. The change in cardiac output or stroke volume is shown in by the arrow 1902. Comparison against line 1903 shows the asymmetric changes present.

Respiratory phase processing recognizes this difference so that inhale information is processed and aggregated independently of exhalation information. In general terms, there is a transition period as the patient moves from one respiratory phase to another. After the transition, information from a given phase can be examined for absolute values, trends, intercepts and other statistical measures. Within a controlled breathing protocol, the patient might complete 5 inhalation activities, for example. These 5 observations can be aggregated together to improve signal quality of overall measurement improvement. Specifically, because the transition period is not synced with the heart rate and heart rates varies, the heart beat will occur at different point relative to the transition period, permitting higher temporal resolution of responses than would be accessible by analyzing the inhalation periods independently. An example will be shown below.

Respiratory Phase Transition Processing. As noted above, there are physiological signals that have fast responses and can be evaluated at the transitions in respiratory phase. For example, signals associated with ventricular interdependence occur rapidly after a respiratory phase transition. In general, rapid transition points are evaluated within about 1.5 seconds of a transition and can be based upon the heart beat before and the heart beat after a transition. Because breathing is not synced with the heart rate the relationship between a transition and heartbeats will vary over time. This variability can be utilized by aggregating and sorting data relative to the phase transition, thus achieving signals with higher temporal fidelity by combining information across respiratory cycles.

Static Clinical Measures. The following static measurements translate the physiological measurements into clinically relevant metrics. Static measurements relate to the average or mean value of a given parameter and are typically processed to remove or average out transient variances due to respiration or changes in venous return. Although dynamic measures are used for fluid management decisions, there is significant value in knowing a patient's general hemodynamic status as defined by static parameters. These parameters enable comparison to other subjects and provide additional information to the care management team. Note that these parameters do not require a perturbation test and can be monitored over time. For example, these parameters can be monitored during sleep, at home, during dialysis, or during patient transport.

Systolic Time Intervals. The three basic systolic time intervals are pre-ejection period (PEP), the left ventricular ejection period (LVET) and the total electromechanical systole (EMS). The critical review by Lewis et al. describes the theoretical basis and validation of the approach. Lewis, Richard P., et al. "A critical review of the systolic time intervals." Circulation 56.2 (1977): 146-158.

In 1963, Weissler et al investigated the volume sensitivity of LVET (and its heart rate corrected index, LVETI) and showed a significant reduction of LVETI during head up tilt, which reduces venous return and stroke volume. Weissler, Arnold M., Leonard C. Harris, and George D. White. "Left ventricular ejection time index in man." Journal of applied physiology 18.5 (1963): 919-923. The authors stated that "a fall in stroke volume (and therefore cardiac output) is reflected in a decrease in left ventricular ejection time and hence a diminution in the ejection time index."

Further work by Stafford et al in 1970 investigated volume sensitivity of additional STI metrics, including LVET, PEP, and EMS. Stafford, R. W., W. S. Harris, and A. M. Weissler. "Left ventricular systolic time intervals as indices of postural circulatory stress in man." Circulation 41.3 (1970): 485-492. The authors demonstrated that decreased venous return caused a prolongation of the pre-ejection period and a shortening of the left ventricular ejection time, while total electromechanical systole diminished minimally. The lengthening of the pre-ejection period and abbreviation of the left ventricular ejection time increased progressively with stepwise reduction in venous return via a head-up tilt protocol.

PEP/LVET is a static measurement parameter that is largely uninfluenced by breathing protocols due to its formulation as a ratio. PEP/LVET shows correlation with ejection fraction and has also been shown to correlate with contractility. Ambrosi, C., et al. "Calculation of the ejection fraction from simultaneously recorded systolic intervals and angiography. Comparative study." Archives des maladies du coeur et des vaisseaux 74.3 (1981): 321-328. Lewis, Richard P., et al. "A critical review of the systolic time intervals." Circulation 56.2 (1977): 146-158. Ahmed, S. Sultan, et al. "Systolic time intervals as measures of the contractile state of the left ventricular myocardium in man." Circulation 46.3 (1972): 559-571. The ratio PEP/LVET combines the (inverse) effects of preload on PEP and LVET. For the purposes of this invention, the metric is simply considered as a general measure of cardiac performance and has demonstrated high correlation with general vascular volume status and changes to sensitivity in decreased vascular volume. Results demonstrating strong correlation with increasing lower body negative pressure are presented below.

Stroke Volume. In cardiovascular physiology, stroke volume (SV) is the volume of blood pumped from the left ventricle per beat. Stroke volume is calculated using measurements of ventricle volumes from an echocardiogram and subtracting the volume of the blood in the ventricle at the end of a beat (called end-systolic volume) from the volume of blood just prior to the beat (called end-diastolic volume). The term stroke volume can apply to each of the two ventricles of the heart, although it usually refers to the left ventricle. In clinical practice, stroke volume is measured by invasive catheter systems or by echocardiography. As communicated above in the studies by Stafford and Weissler, the LVET period is a good surrogate for stroke volume. The work by Harley et al. showed a close and direct linear relationship between the duration of ejection and stroke volume. Harley, Alexander, C. Frank Starmer, and Joseph C. Greenfield Jr. "Pressure-flow studies in man. An evaluation of the duration of the phases of systole." *Journal of Clinical Investigation* 48.5 (1969): 895.

Percent Change in Stroke Volume. The percent change is stroke volume is a measure of change from a subject's baseline stroke volume to the condition observed. Stroke volume is a subject-specific parameter, thus the use of a percentage change from baseline creates a normalized value that can be used for rapid assessment as well as the trend monitoring. The percentage change in stroke volume can be determined from a linear model where the predictive features include but are not limited to the systolic time intervals (PEP, LVET, PEP/LVET), heart rate, and pulse transit time. One of ordinary skill will appreciate that a variety of linear or non-linear models can be formulated to determine the percent change in stroke volume from these features. Results demonstrating the measure across a group of subjects experiencing increasing lower body negative pressure are shown below.

Pulse Arrival Time. Pulse arrival time can be used effectively as a general monitoring tool for acute changes in hemodynamic status. Pulse arrival time (PAT) is a combination of PEP and PTT. PEP is a preload-dependent time interval that will lengthen when a fluid responsive subject encounters a preload decrease or increase. PTT is sensitive to blood pressure changes. In a hemodynamically stable patient the PAT will be stable but will begin to change as the patient begins to encounter hemodynamic issues or has a change in vascular tone. The presence of PAT changes can be used to alert the medical staff to physiological changes that should be examined further.

Dynamic Clinical Measures. Dynamic measurements are those metrics that vary over a given period and are evaluated in a manner that emphasizes that change or variance. Typically, these parameters are focused on the variances observed over a respiratory cycle or cycles. The following dynamic measurements translate the physiological measurements into clinically relevant metrics for effective hemodynamic assessment and treatment. Dynamic measurements can be calculated with awareness of the controlled breathing protocol.

Dynamic Elastance. Arterial elastance is defined as the slope of the arterial volume-pressure relationship. In simple terms it is a ratio of the change in pressure to changes in volume. Arterial elastance is considered an integrative parameter of overall arterial system behavior. More recently, several authors have advocated the assessment of arterial or vascular tone in a dynamic fashion by using cyclic changes in pulse pressure and stroke volume during mechanical ventilation. The proposed measurement referred to as dynamic arterial elastance (Eadyn) calculates the ratio of the pulse pressure variation (PPV) to stroke volume variation (SVV) during positive pressure ventilation, i.e., Eadyn=PPV/SVV. Dynamic arterial elastance has been shown to predict the arterial pressure response to volume expansion (VE) in hypotensive, preload-dependent patients. The studies validating this approach measured PPV from an invasive arterial line while SVV was obtained by esophageal Doppler imaging. Romero, Manuel Gracia, et al. "Dynamic arterial elastance as a predictor of arterial pressure response to fluid administration: a validation study." Critical Care 18 (2014): 626-626. The invention departs from prior work by using completely noninvasive methods to determine Eadyn. The invention calculates dynamic arterial elastance as Eadyn=PAV/LVETV, where PAV is the variation in the pulse amplitude and LVETV is the variation in the LVET. As discussed above, pulse amplitude can be quantified as pulse height or area under the curve (AUC). Measures of variation, PAV and LVETV, can be formulated using the range (i.e., min to max) of these measurements, e.g., $$PAV = \frac{(PA_{max} - PA_{min})}{(PA_{max} - PA_{min})/2} \times 100\%.$$

Alternatively, the variation can follow the definition for coefficient of variation and use the mean and standard deviation, e.g., $$PAV = \frac{PA_{SD}}{PA_{mean}} \times 100\%,$$

or a robust version of this statistic based on the median and median absolute deviation. One of ordinary skill will appreciate that a variety of statistics can be used to quantify variation. Results demonstrating changes in Eadyn in subjects undergoing increasing lower body negative pressure are shown below.

Stroke Volume Phase Relationship. Historical work in the area of fluid responsiveness has focused on variance measures due to perturbation or stress test, typically mechanical ventilation. Stroke volume variance, pulse pressure variance, and systolic pressure variance are commonly cited metrics. An important element of this invention arises from examination of the phase relationship between the change in intrathoracic pressure and the resulting change in stroke volume. As noted above in the heart-lung interactions discussion and shown in FIG. 5, the normal cardiac function has a defined phase relationship.

In the presence of hypervolemia, as seen in heart failure and specifically hemodynamic congestion, the phasic relationship associated with increasing and decreasing intrathoracic pressure is altered. Specifically, to the extent that increased intrathoracic pressure reduces in-systolic volume more than it reduces in-diastolic volume the stroke volume will increase. As an example, consider the relationship between position in the respiratory cycle and LVET. In normal hearts, inspiration will cause an immediate decrease in preload and SV (and LVET). However, in individuals with hemodynamic congestion, inspiration will cause a decrease in preload but no change or increase in SV (and LVET) because of the extreme position of these individuals on the plateau or falling limb of the Frank-Starling cardiac function curve.

The previously referenced work of Stafford does not examine the data from a phasic relationship perspective but careful examination of the data shows that the relationship of venous return and systolic time intervals is altered dramatically in heart failure. FIG. 4A of the publication shows the relationship between PEP and LVET as a function of head tilt (decreasing venous return and preload) for individuals with normal hearts and those with hypervolemia and congestive heart failure. FIG. 4B shows the same information but after diuresis. In individuals with CHF, head up tilt fails to reduce LVET (or increase PEP) despite a decrease in venous return, however diuresis recovers the typical relationships. This information demonstrates that the same stress test will exhibit a different response on the same heart depending upon volume status. The use of phasic relationships has the benefit of being independent of amplitude size and is focused on temporal relationships between signals. The processing is independent of the magnitude of the variance observed. In practice, the use of magnitude-insensitive measures is important because the perturbation done by a heart failure patient at home will have some inherent variances, as an example. One of ordinary skill will appreciate that multiple metrics of vascular volume status can be accessed via an examination or normal versus abnormal phase.

Pattern Recognition for Hemodynamic Assessment. As discussed elsewhere herein, a defined change in venous return through a variety of perturbations creates a measurable change in left heart stroke volume. The measurable parameters contain amplitude information, phase information, and response characteristics. The resulting signals information is information-rich and well-suited to pattern recognition or classification methods.

Figure 22:
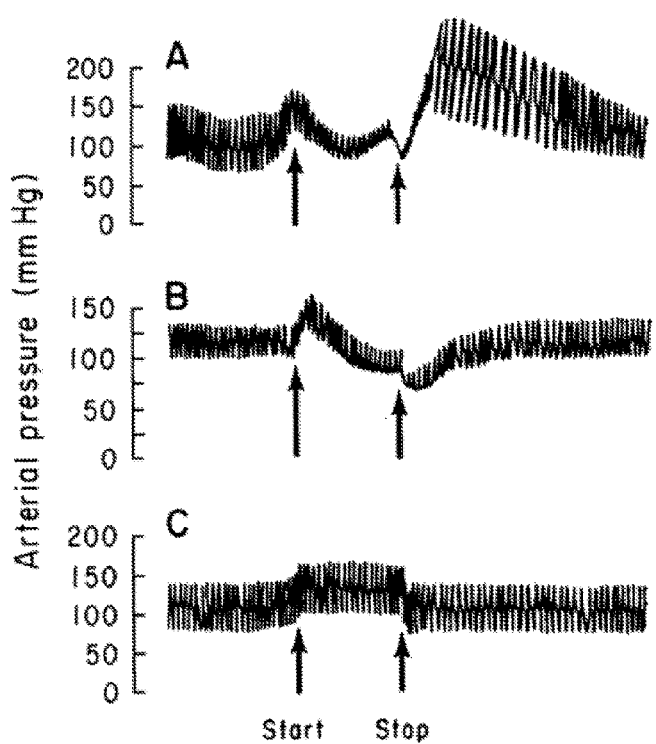
FIG. 22 is data from subjects performing Valsalva with varying degrees of heart failure.

To effectively demonstrate the concept, historical work associated with the Valsalva maneuver will be used. A Valsalva maneuver causes an immediate increase in cardiac output by squeezing blood from the pulmonary circulation to the left heart, but this is very quickly followed by a marked reduction in cardiac output due to reduced right heart filling. More detailed information on the Valsalva maneuver is published in work by Zema at al. Zema, Micheal J., et al. "Left ventricular dysfunction—bedside Valsalva manoeuvre." British heart journal 44.5 (1980): 560-569. FIG. 22 shows the different responses to the Valsalva maneuver due to severity of heart failure. This type of defined response is amenable to current technology machine learning techniques.

A single Valsalva maneuver is a single measurement and is difficult for the subject to complete due to the duration of the maneuver and the moderately high intrathoracic pressures. Embodiments of the present invention address these limitations by using repeatable stress tests such the mini-Mueller and mini-Valsalva controlled breathing test. The breathing test will create changes in venous return and subsequently left ventricular stroke volume that can be measured easily and noninvasively. These measures can be used in raw format or after processing to create a feature vector that enables determination of hemodynamic status including the presence of hypervolemia in heart failure patients.

Exhalation Variance Test. The exhalation variance test (EVT) quantifies changes in stroke volume by examining the minimal stroke volumes obtained via a controlled breathing test at two or more different pressures during the exhale phase. The exhalation variance test is a new functional hemodynamic parameter, using intentionally generated changes in stroke volume via two or more controlled breathing pressures levels. The processing is respiratory phase specific.

An advantage of IVT is in the standardized stimulus that is being used to test fluid responsiveness independent of a pre-defined tidal volume. The uniqueness of the IVT relative to the other functional hemodynamic parameters stems also from the fact that it provides information or estimates on the slope of the Frank-Starling curve by producing sequential incremental challenges to left ventricular filling via a controlled breathing maneuver. In addition, since the IVT is calculated only from the lowest values of a stroke volume measured during exhale, it is not influenced by the early augmentation of the left ventricular stroke volume due to venous flow from the lungs. Perel, A., et al. "Respiratory systolic variation test reflects preload during graded haemorrhage in ventilated dogs." BRITISH JOURNAL OF ANAESTHESIA 74 (1995): A-134. This phenomenon becomes the predominant component of stroke volume fluctuations during hypervolemia and/or congestive heart failure and is not predictive of fluid responsiveness. The fact that conventional metrics of systolic pressure variance and stroke volume variance are based on the difference between the maximal and minimal values of systolic arterial pressure during the mechanical breath might reduce their accuracy in the prediction of volume responsiveness, especially in the presence of impaired left ventricular function.

The exhalation variance test can be used or applied to all measured parameters and has demonstrated reliable results when used with LVET, PEP, and PEP/LVET.

Exhalation Phase Response Test. During a controlled breathing test, the subject will exhale against pressure for approximately 5 seconds. With an average heart rate of about 60 beat per minute, this test will provide four to five unique observations of hemodynamic assessment. As explained above, the cardiac function of the heart will change over the observation period due to an immediate increase in cardiac output by squeezing blood from the pulmonary circulation to the left heart, followed quickly by a reduction in cardiac output due to reduced right heart filling. The trends observed during this period have been should to be highly diagnostic for hemodynamic assessment and specifically volume responsiveness. The calculation involves determining the slope defined by the stroke volume metric (such as LVET, PEP, PAT, PEP/LVET, or other cardiac function metrics) following the respiratory phase change. Slopes with greater magnitudes values represent a strong decreasing stroke volume during elevation of intrathoracic pressure and identify the patient to be in the volume responsive part of the Frank-Starling curve. In patients showing adequate cardiac preload, the slope will be of smaller magnitude. Therefore, additional volume administration in the circumstance of a low slope will not increase stroke volume.

The Exhalation Phase Response as presented above was based upon slope determination but can also be based upon a variety of metrics associated with rate of change, shape characterization, maximum point detection, etc. The Exhalation Phase Response Test can be used or applied to all measured parameters and has demonstrated reliable results when used with LVET.

Inhalation Phase Response Test. The inhalation phase response test is similar to the exhalation phase response test but the physiology and interpretation of the results is different. Examination of the Guyton venous return curve (FIG. 7) shows that increased intrathoracic pressure creates a continuous decrease in cardiac output and the function has no discontinuities. In stark contrast, decreased intrathoracic pressure can result in venous collapse and a plateau in terms of maximal venous return. Therefore, the slope results generated can be influenced by the degree of venous collapse.

As described above, higher slope values represent an increase in stroke volume during decreased intrathoracic pressure and identify the patient as being in the volume responsive part of the Frank-Starling cardiac function curve. Asymmetries in the determined slopes between the exhale phase response test and the inhale phase response test can be used to define the subject's location on the Frank-Starling cardiac function curve. Note that both the Exhalation Phase Response Test and the Inhale Phase Response Test can be conducted at different pressure levels, providing additional information for diagnostic and treatment purposes.

The Inhalation Phase Response as presented above was based upon slope determination but can be based upon a variety of metrics associated with rate of change, shape characterization, maximum point detection, etc. The Inhalation Phase Response Test can be used or applied to all measured parameters and has demonstrated reliable results when used with LVET.

Exhale-to-Inhale Transition Test. In clinical testing conducted, one of the largest changes observed is the change from a forced exhale to an inhale. The decrease in stroke volume and associated metrics including LVET, PEP, PEP/ LVET, and PAT is quite significant. The metric is specific for information at the end of the exhale phase and the start of the inhale phase. In general, rapid transition points are evaluated within about 1.5 seconds of a transition and are largely based upon cardiac function associated with the heart beat closest to the transition. Thus, the metric qualifies the amount of change adjacent to the exhale to inhale transition.

In mechanically ventilated patients, variance-based metrics (such as stroke volume variance [SVV] or pulse pressure variance [PPV]) exhibit increases with decreasing volume status. A significant observation of this invention with controlled breathing is the discovery that the change across the exhale to inhale transition decreases with decreasing volume. Thus, the trend is the opposite of the metrics previously use for volume assessment. This discovery can be important in understanding the inconsistent results that have been published and presented in the prior art.

This discovery is based upon two distinct observations. First, as noted above, the response time associated with ventricular interdependence effects is rapid due to the lack of any air damping. The second is associated with the unbalanced response of the interventricular septum. Based upon published research, changes in the left ventricular size weakly influence the function of the right ventricle. Jardin, Frangois. "Ventricular interdependence: how does it impact on hemodynamic evaluation in clinical practice?." Intensive care medicine 29.3 (2003): 361-363. However, a sizable change in the volume of the right ventricle leads to a decrease in the volume of the left ventricle because of a leftward shift of the interventricular septum. Jessup M, Sutton S G, Weber K, et al. The effect of chronic pulmonary hypertension on the left ventricular size, function, and interventricular septal motion. Am Heart J 1987; 113; 1114-22. In fact, systolic overload of the right ventricle results in the most severe geometric configurational changes of the left ventricle. This systolic overload leads to a maximal leftward displacement of the interventricular septum, or flattening or reversal of septal curvature and compression of the left ventricle.

These nuances of septal movement create a valuable and district feature that can be leveraged for clinical significance. Specifically, at the transition from exhale to inhale, the decrease in intrathoracic pressure fills the right heart resulting in a significant leftward displacement of the interventricular septum, and markedly low stroke volume from the left heart. The amount of displacement is related to the amount of venous return and is maximal when venous collapse is minimal. As demonstrated by the Guyton venous return curve, the amount of venous return will decrease with decreasing volume due to venous collapse. As the subject becomes volume depleted, the influence of septal movement decreases and results in a decreased difference in the stroke volume metric.

Figure 23:
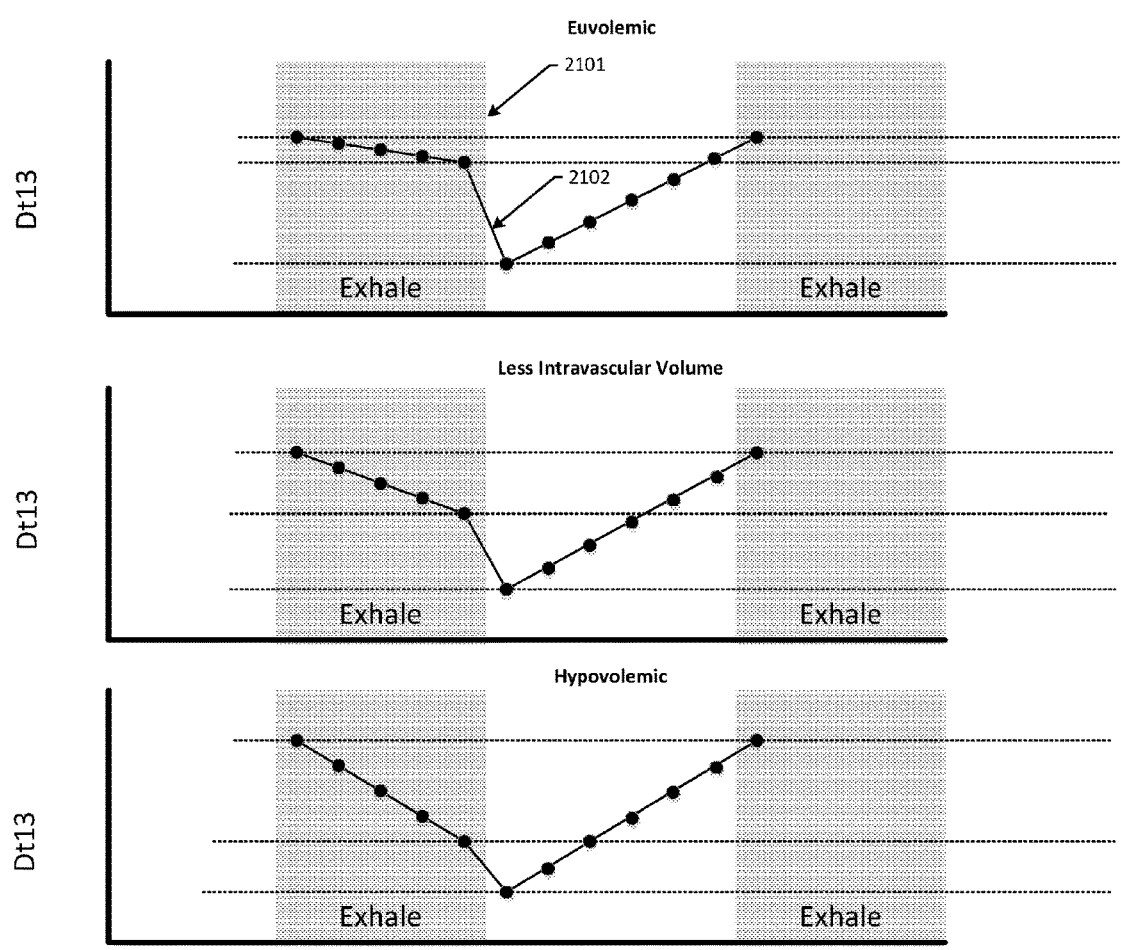
FIG. 23 is a schematic representation of changes in LVET with changing intravascular volume.

FIG. 23 is a schematic representation of the above physiological processes using LVET as the measured cardiac function variable. The top graph is of a euvolemic patient. The exhale to inhale transient is labeled 2101, and the influence of the rapid transition is identified with label 2102. Examination of the plot reveals that the magnitude of change at the rapid transition decreases with decreasing volume while the other metrics increase. The total variance observed (max-min) increases slightly with decreasing intravascular volume but the sensitivity of the measurement is reduced dramatically by the rapid transition change reduction. Note that the rapid transition point change can be increased depending upon heart failure, decreased afterload and other changes. Thus, the analysis of data by respiratory phase as well as at the rapid transitions can be useful for accurate hemodynamic assessment of the patient.

The Exhale-to-Inhale Transition Test can be used or applied to all measured parameters and has demonstrated reliable results when used with LVET.

System Demonstration. The following section will demonstrate the usefulness of example embodiments of the invention on real data and provide comparison information relative to prior art methods.

Datasets Used for Demonstration. Although significant testing of the system has been performed, the demonstration of utility described herein focusses on three different datasets.

The first dataset presented as an example embodiment was obtained from a female patient with end stage renal disease undergoing a dialysis session. This particular patient was selected because she was fluid overloaded at the start of the session, having missed her prior dialysis session, and eventually become hypotensive. With the occurrence of hypotension, ultrafiltration was stopped and 100 ml of fluid administered. The last controlled breathing protocol was during this small fluid administration at the end of the session. Thus, over the course of the therapy, the subject went from being fluid overloaded to slightly hypovolemic and provides a single data set that shows the value of the invention. These data will be referred to as the dialysis dataset hereafter.

The second dataset presented is from a lower body negative pressure (LBNP) test involving eight different subjects. LBNP is a standard experimental approach for inducing decreases in circulating vascular volume. The use of lower body negative pressure pulls blood into the lower body and creates transient hypovolemia that can be reversed rapidly. The subjects examined were subjected to 0, −15, −30 and −45 mmHg of lower body negative pressure. These data will be referred to as the LBNP dataset hereafter.

The third data set used for demonstration purposes was obtained from a 56-year-old female with no known heart disease. The subject moved through four positions, staying in each position for approximately 1 minute. The position sequence was: (1) resting supine with legs raised, (2) resting supine with legs flat, (3) sitting upright, and (4) standing. Each positional change will cause a further reduction to venous return. These data will hereafter be referred to as the positional change dataset.

Figure 24:
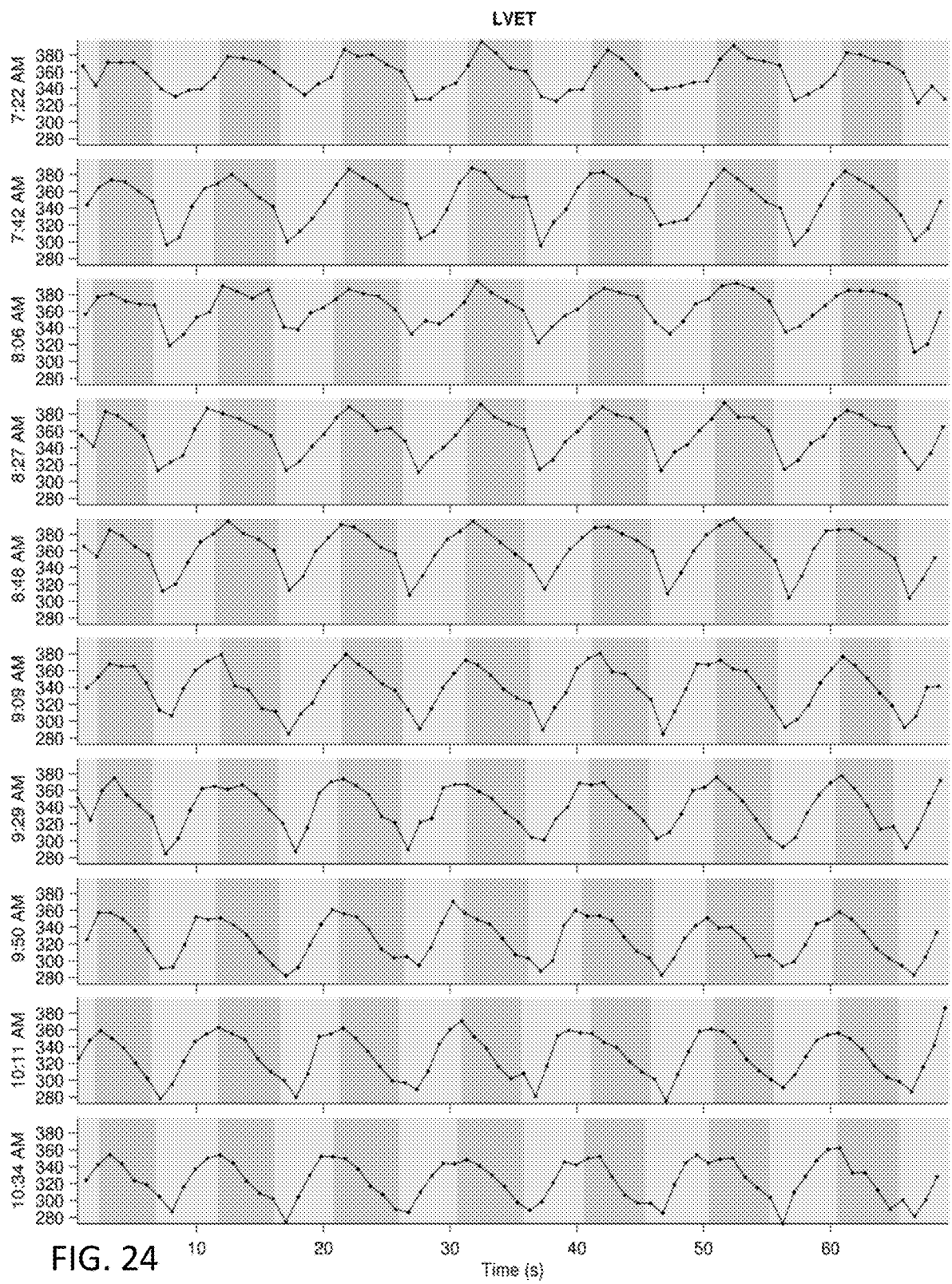
FIG. 24 are LVET plots for the demonstration patient.
Figure 25:
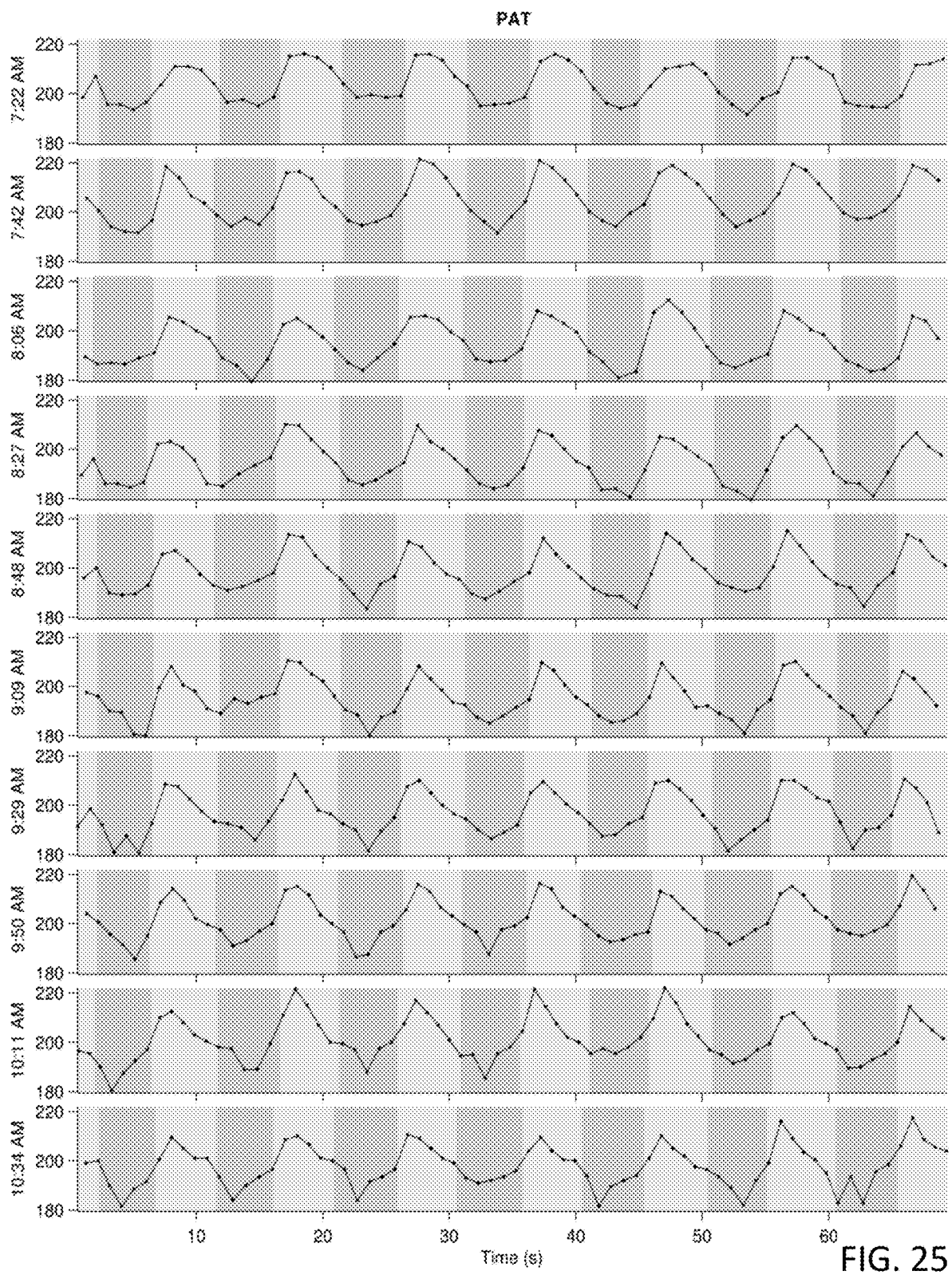
FIG. 25 are PAT plots for the demonstration patient.

Demonstration with Dialysis Data. FIG. 24 shows the LVET for the patient over the dialysis treatment. FIG. 25 shows the PAT trends for the demonstration patients over the dialysis period. The exhale phase is shaded darker on each plot. The plot contains two lines associated with different resistance breathing pressures. The dashed line is associated with data obtained during paced breathing at 6 breathes per minute and an exhale pressure of 5 cm $H_2O$. The solid line was obtained at an exhale pressure of 10 cm $H_2O$.

Examination of FIG. 24 shows that the response to the exhale activity at the start of the study is almost flat. Based upon historical Valsalva work this would suggest that the patient is fluid overloaded and in moderate heart failure. During the dialysis treatment the LVET changes significantly and shows a dramatic decreasing trend during the exhalation phase as the patient loses intravascular volume. In addition, the mean LVET decreases over time, consistent with a decrease in stroke volume. The figure confirms the basic premise that there is good agreement between the different controlled breathing pressures when the patient is on the flat part of the Frank-Starling curve.

Figure 26:
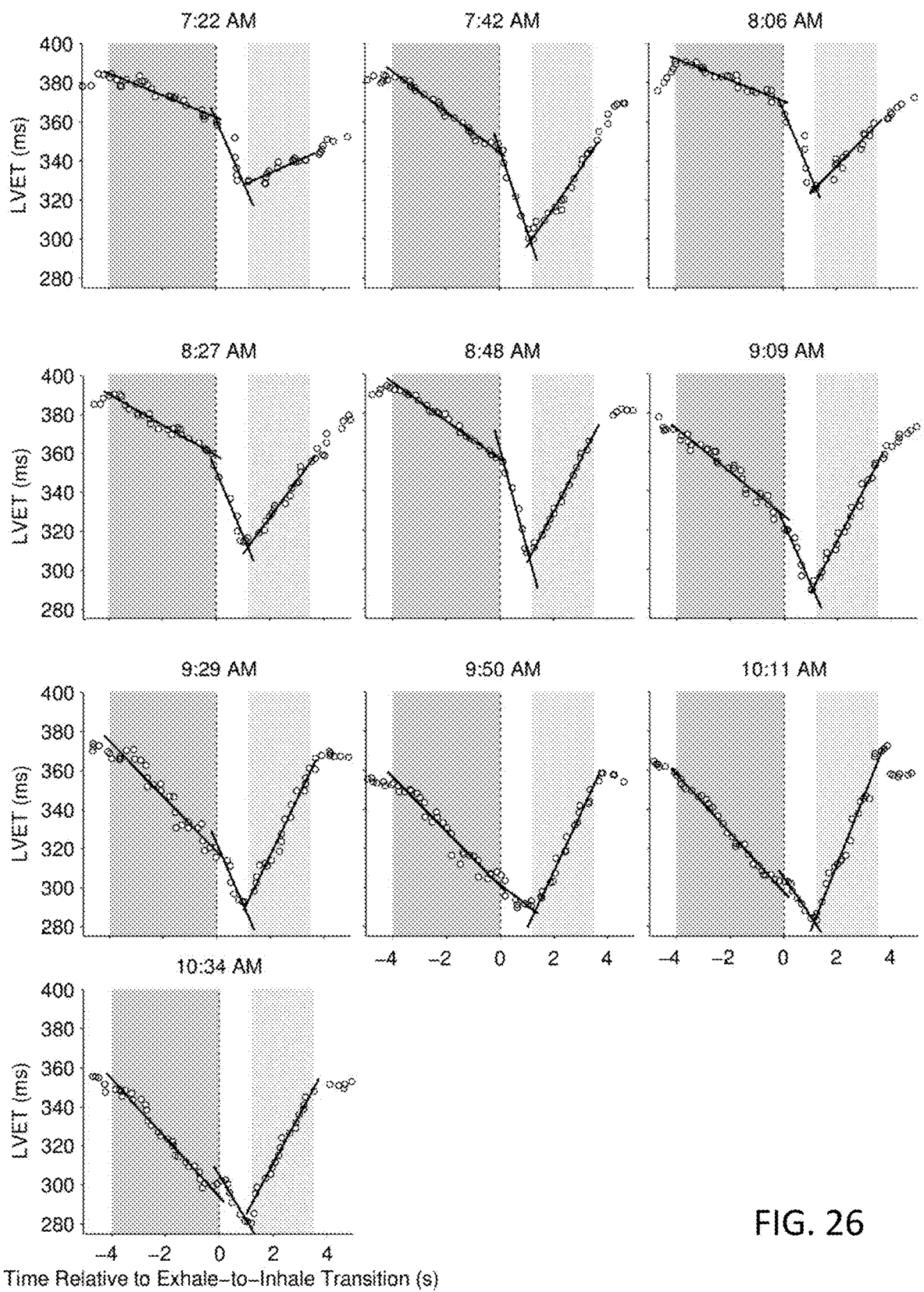
FIG. 26 is a plot of the exhalation phase response test results from the demonstration patient.

FIG. 26 shows the results of the Exhalation Phase Response Test, Inhalation Phase Response Test, and Exhalation-to-Inhale Transition Test using LVET for the demonstration patient and the data aggregation processing approach. With the aggregation processing method, the time of each heartbeat is aligned relative to the Exhale-to-Inhale transition. Because heart beats are not synced with respiratory phase, this alignment effectively increases the temporal resolution; hence, trends and transitions can be studied with greater fidelity than would be afforded by the heart rate (which is roughly 1 beat/second). The Exhalation Phase Response Test tracks the slope of LVET over the exhalation period, which is shown with dark gray shading. Over roughly three hours of dialysis treatment, the slope increased substantially in magnitude, indicating a progressive loss of volume. For the first hour of dialysis, the change during exhalation is roughly 20 msec, however by the end of dialysis the reduction in LVET over exhalation is 60 msec. The Inhalation Phase Response Test tracks the slope of LVET over the inhalation period, which is shown with light gray shading. Over the dialysis period, the slope increases in magnitude, indicating reduced volume. The Exhalation-to-Inhale Transition Test tracks the change in LVET during the transition period, which is shown with white shading. As can be seen from examination of FIG. 26, this change in the transition period decreases over time, a further indicator of volume reduction. For instance, at the start of the dialysis treatment (times 7:22, 7:42 and 8:06 AM) the degree of change during the transition period is 30 to 40 msec, however towards the end of the dialysis session the change has decreased to roughly 20 msec.

Figure 27:
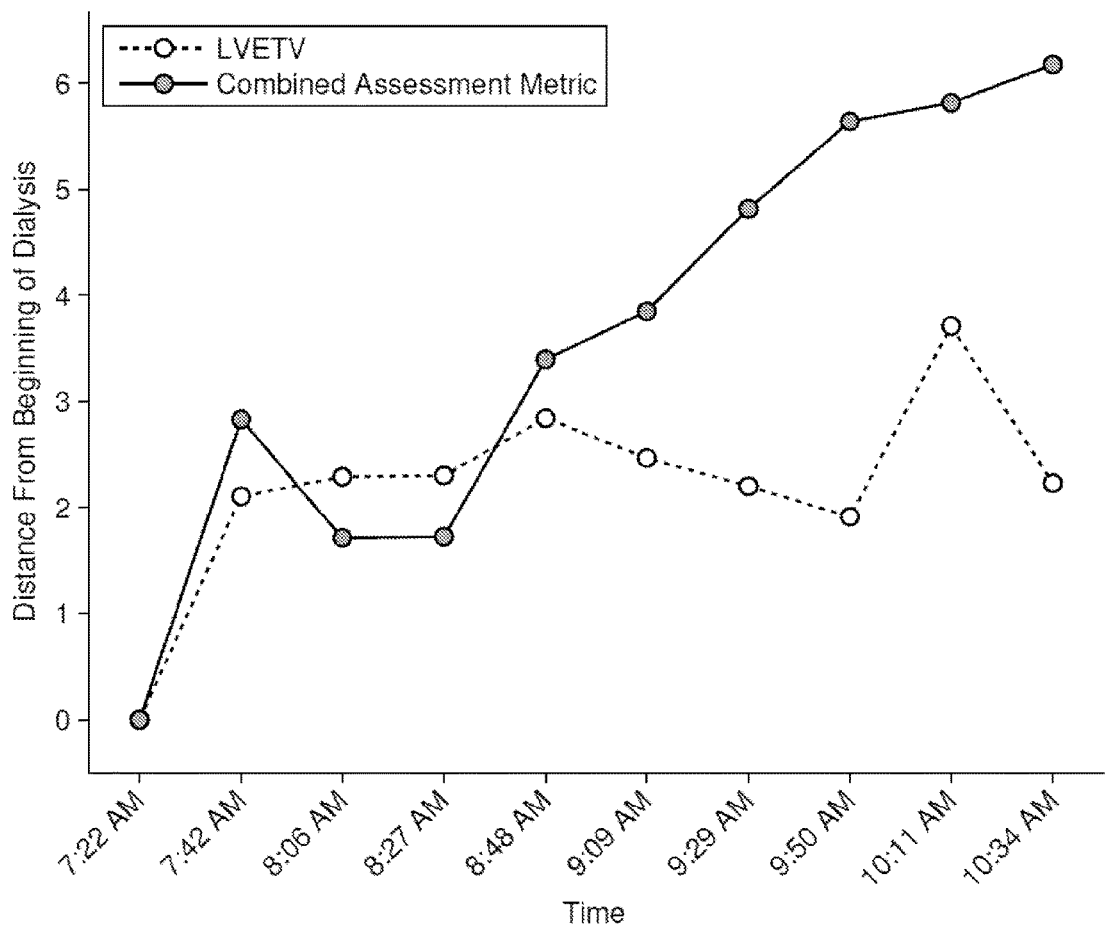
FIG. 27 is a plot an aggregated processing methods versus conventional processing.

The results from the Exhalation Phase Response Test, Inhalation Phase Response Test, and Exhalation-to-Inhale Transition Test can be combined with each other, as well as with any other dynamic or static parameters, to create a Combined Assessment Metric for the determination of volume status and treatment. As an example in the demonstration subject, the dynamic LVET measures from the Exhalation Phase Response Test, Inhalation Phase Response Test, and Exhalation-to-Inhale Transition Test shown in FIG. 26 are combined with the static measure of LVET (mean over several respiratory cycles) to form a multivariate Combined Assessment Metric. The Combined Assessment Metric is calculated for each temporal window throughout the dialysis session and its multivariate distance from the beginning of dialysis is computed, as shown in FIG. 27. These results can be directly compared with those achieved with the conventional variance processing approach. Specifically, the LVET variance (LVETV) is computed from the identical data using the equation $$LVET\ \text{Variance} = \frac{(LVET_{max} - LVET_{min})}{(LVET_{max} - LVET_{min})/2} \times 100\%,$$

and the distance from the beginning of dialysis is calculated. From examination of FIG. 27 it is clear that the sensitivity of the Combined Assessment Metric to volume changes is superior to the conventional processing approach.

Figure 28:
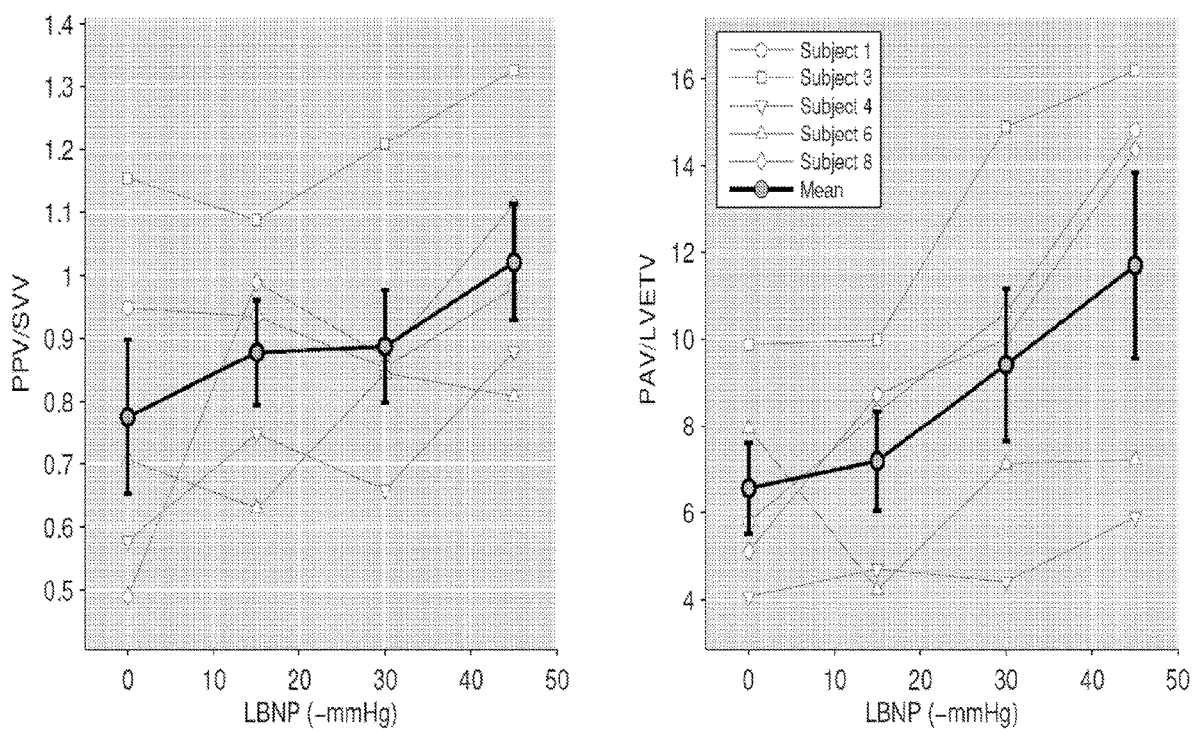
FIG. 28 is a plot associated with dynamic elastance.
Figure 29:
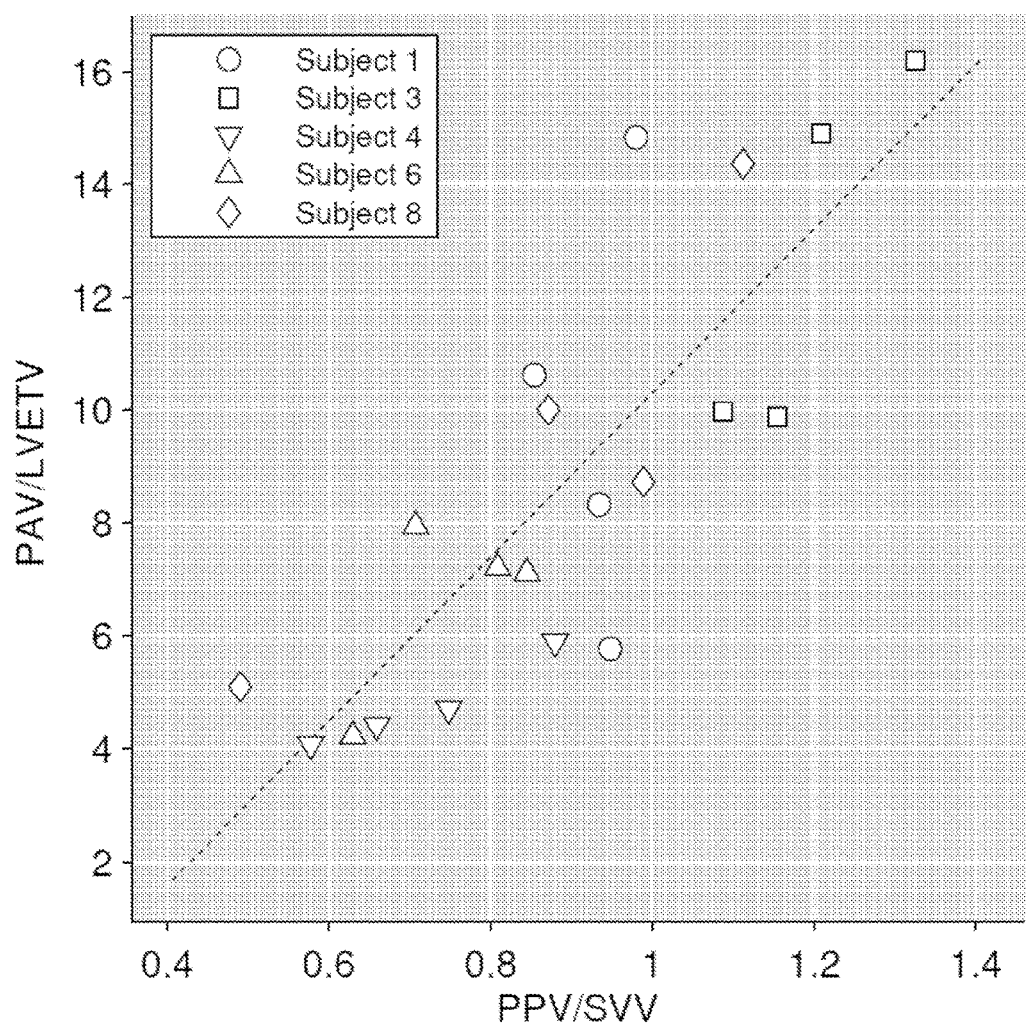
FIG. 29 is a detailed plot of the dynamic elastance results.

Demonstration with LBNP Data. FIG. 28 is a demonstration of dynamic elastance changes as a result of the lower body negative pressure (LBNP) test. As LBNP was increased and subjects lost circulating volume, the autonomic system was activated and responded. The left graph shows the results obtained with a reference instrument, a Finometer, following the equation Eadyn=PPV/SVV. The right graph shows the results obtained with an example embodiment of the present invention, using the definition Eadyn=PAV/LVETV. Both methods show clear increases in vascular tone (vasoconstriction) with increasing LBNP. FIG. 29 provides a direct comparison between the reference instrument and the invention, showing excellent agreement.

Figure 30:
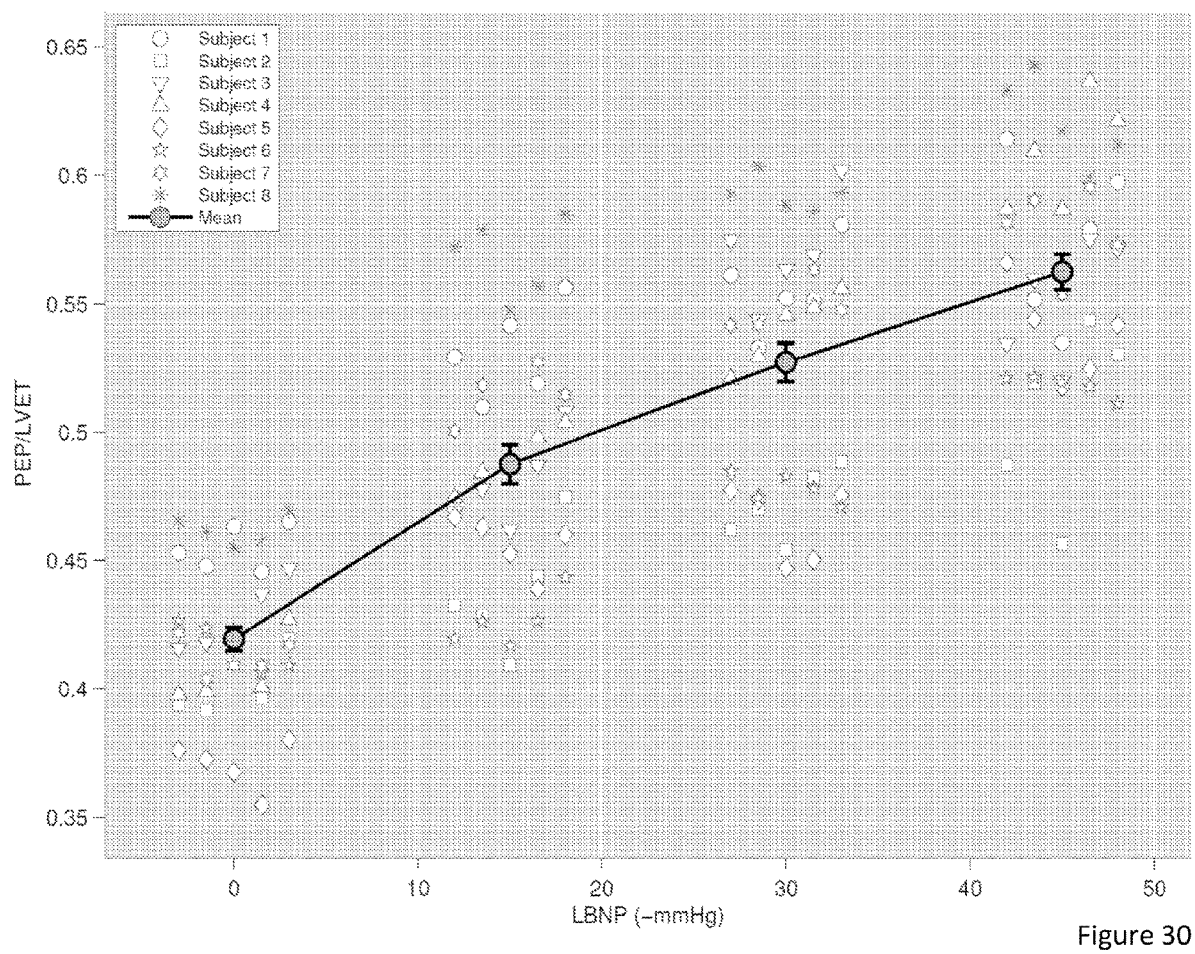
FIG. 30 is a plot of PEP/LVET versus Lower Body Negative Pressure.

FIG. 30 is a demonstration of the sensitivity of PEP/LVET to changes in LBNP across different subjects. At each LBNP level (0, −15, −30, −45 mmHg) five different breathing protocols were performed. Examination of the graph reveals a systematic increase of PEP/LVET at each LBNP and that the measurement is largely insensitive to breathing perturbations.

Figure 31:
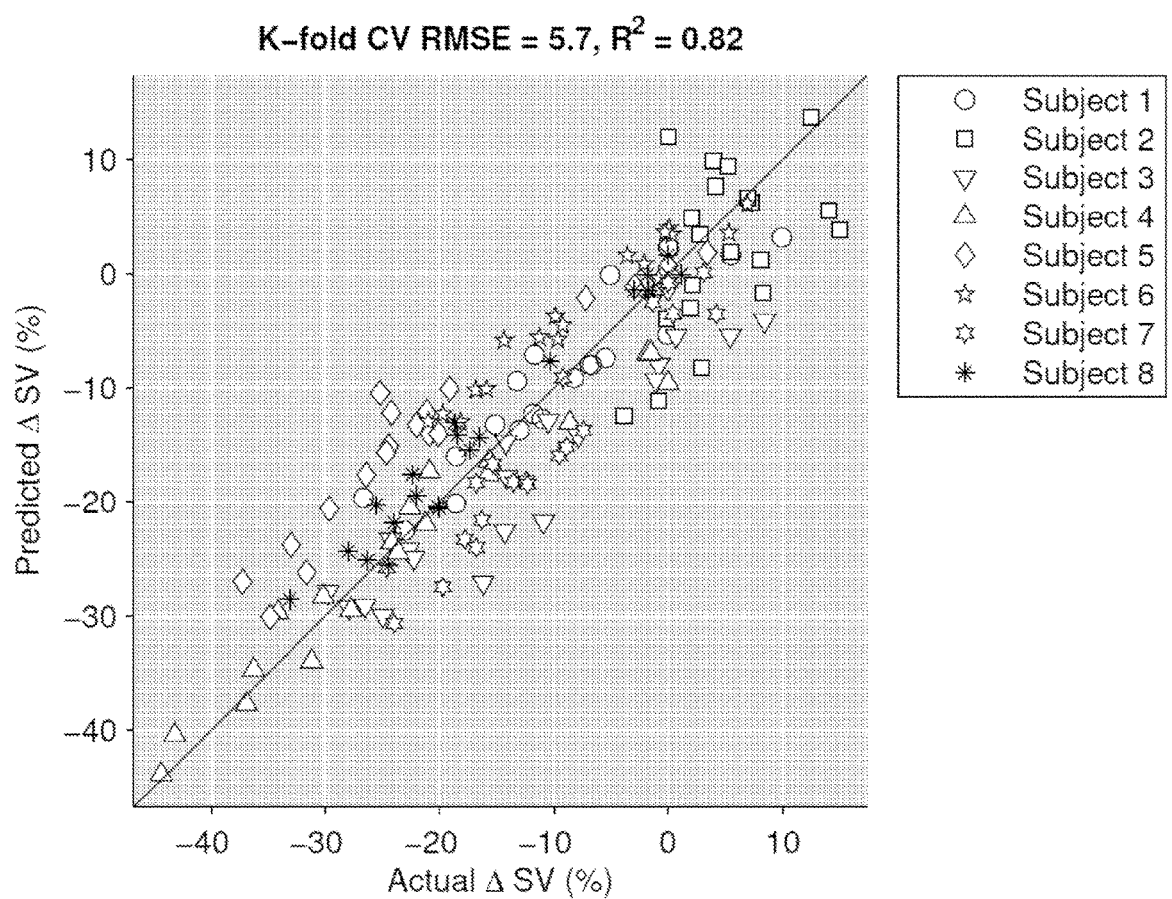
FIG. 31 is a plot of predicted change in stroke volume versus measured changes.

FIG. 31 is a demonstration of the ability to predict the percent change in stroke volume across the subjects studied in the LBNP test. The x-axis is the % change in stroke volume from baseline as measured by a Finometer and the y-axis shows the % change in stroke volume determined by an example embodiment of the present invention.

Figure 32:
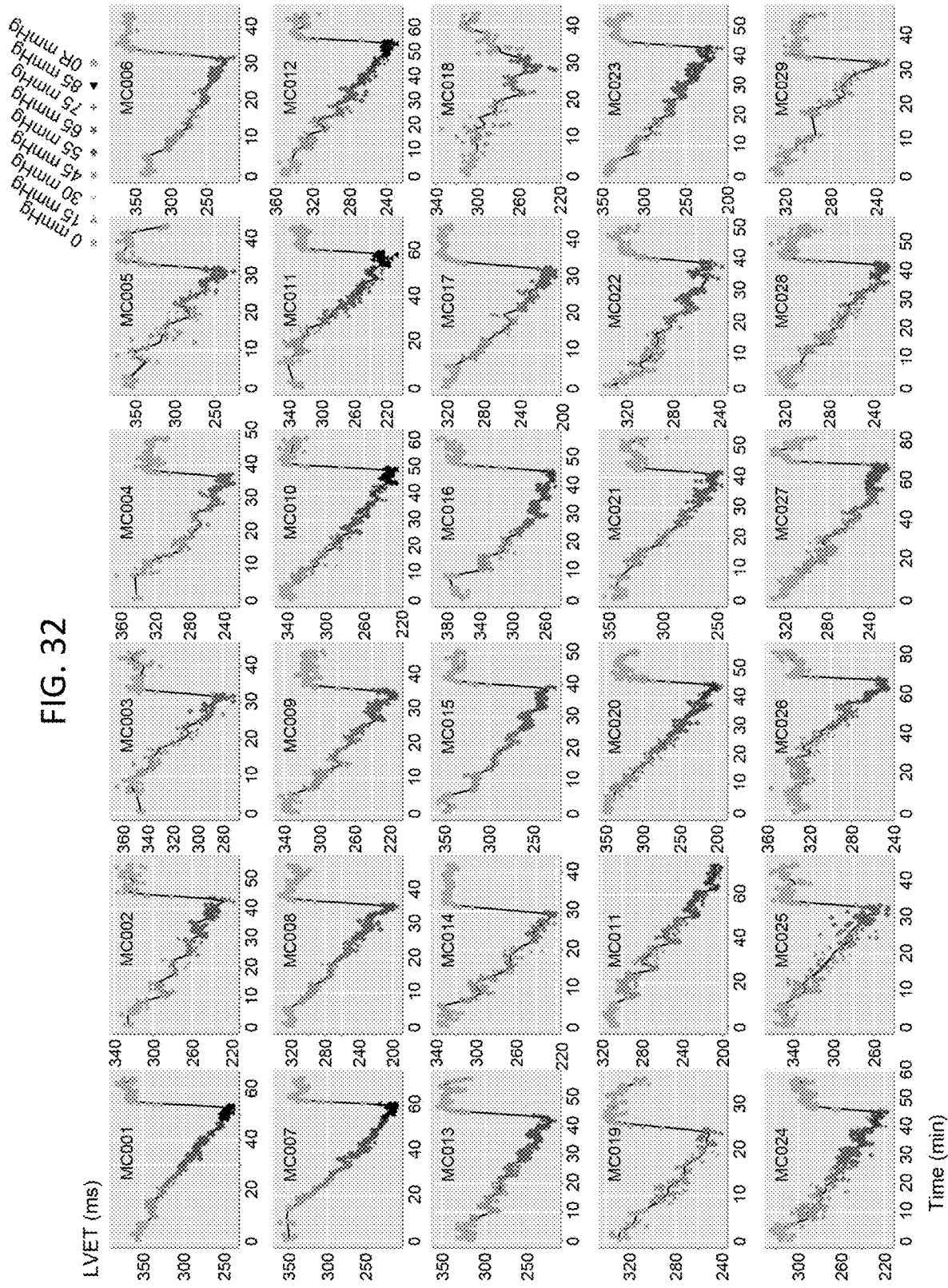
FIG. 32 is a plot of invention-derived LVET changes versus lower body negative pressure.
Figure 33:
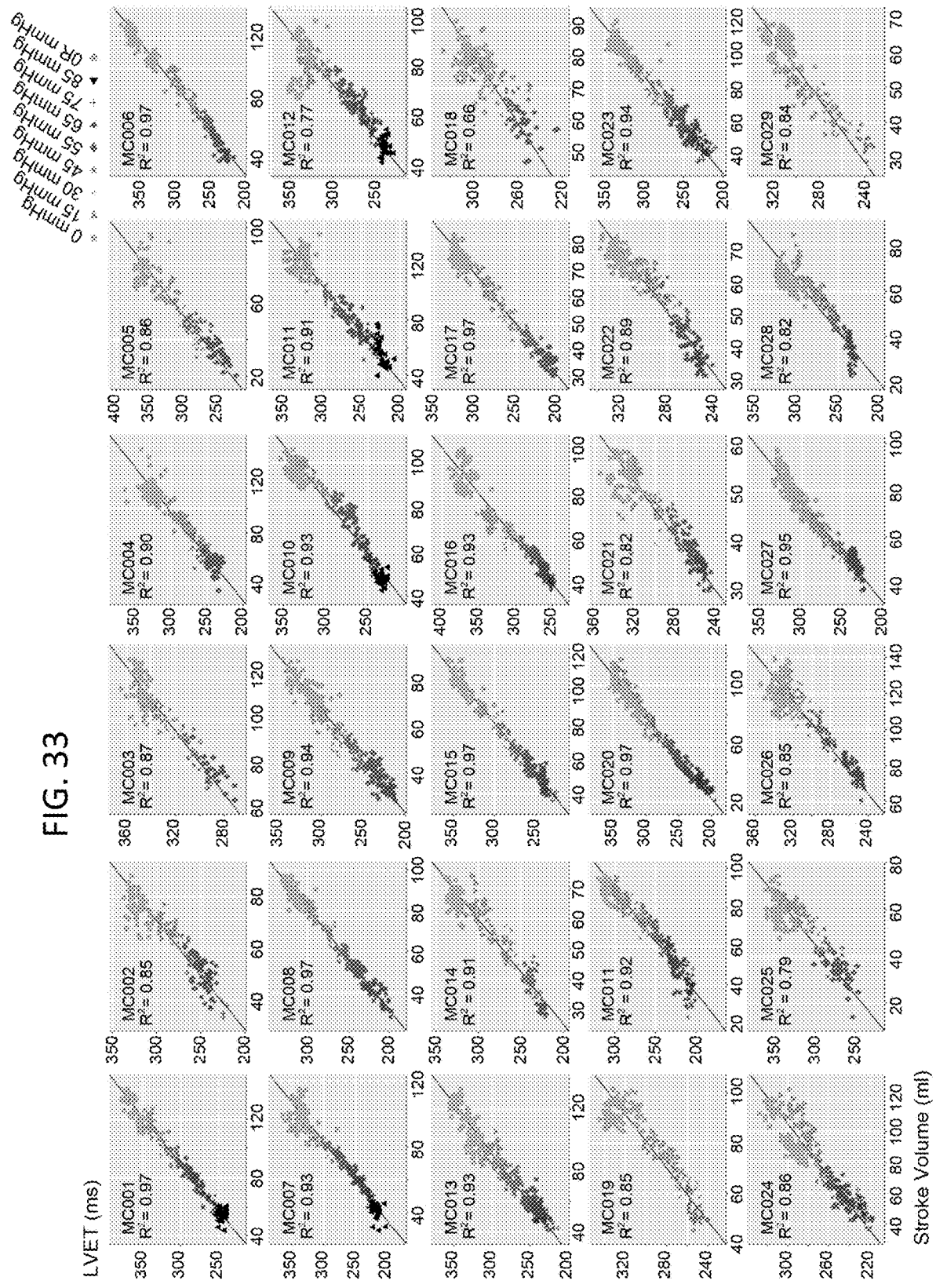
FIG. 33 is a plot of invention-derived LVET changes versus stroke volume.

For purposes of heart failure monitoring within individual subjects, measured parameters should trend with changes in intravascular volume. For the purpose of demonstrating system performance, LVET was estimated based upon the recorded PPG in subjects undergoing a lower body negative pressure test. Lower body negative pressure was increased until the subjects developed pre-syncopal symptoms or experienced hypotension. FIG. 32 shows the results from 30 tests conducted. Examination of the figure shows systematic changes in LVET versus LBNP. The system also shows a fast response during the recovery phase of the study, (denoted as 0R mmHg). FIG. 33 shows the same LVET values from the prior figure but plotted versus stroke volume as determined by a Finometer (reference system) due to changes in lower body negative pressure. Thus, these two plots clearly demonstrate the system's ability to track changes in intravascular volume status within an individual subject.

FIG. 34A shows an example of pulse contour analysis during a lower body negative pressure (LBNP) test. An average PPG waveform is formed from roughly 1 minute of data at each LBNP step and the derivative PPG waveform is computed and normalized to span from 0 to 1. A mixture of Gaussians model, of the form $y=\Sigma_{i=1}^{n} A_i e^{-(x-\mu_i)^2/(2\sigma_i^2)}+c$, is then fit to the data based on minimization of the sum of the squares of the errors. The free parameters are the amplitudes ($A_i$), centers ($\mu_i$) and width ($\sigma_i$) of the Gaussians, as well as the number of Gaussians used in the mixture (n) and an offset (c). In this example, the number of Gaussians is set to three. Examination of the figure shows that as the level of LBNP increases and intravascular volume declines, the pulse contour undergoes several changes that are captured by the fit Gaussians (labeled G1, G2 and G3). In particular, the magnitude of the first reflected wave, is captured by parameter $A_2$, reduces significantly. As shown in FIG. 34B, the ratio between the amplitudes of the first reflection and the primary wave, $A_2/A_1$, exhibits high sensitivity to the loss of blood volume and to the recovery of normal hemodynamic status when LBNP is released (0R mmHg). Pulse contour analysis represents PPG based method for hemodynamic assessment.

Figure 35:
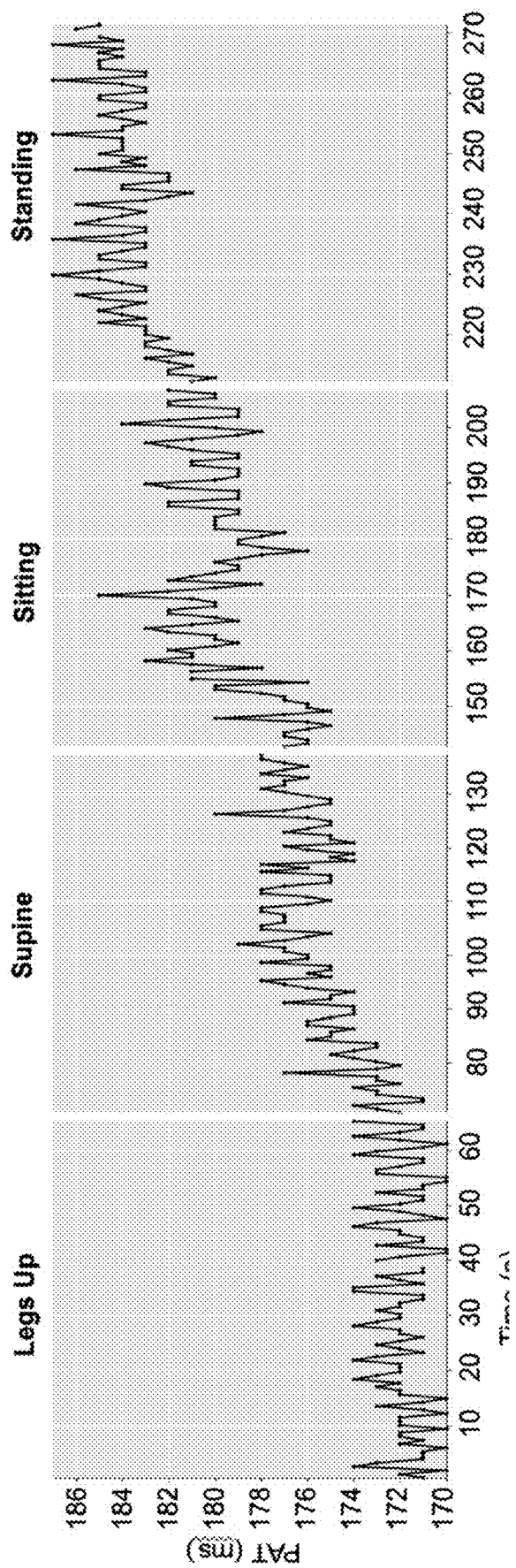
FIG. 35 is the PAT changes observed due to position changes.
Figure 36:
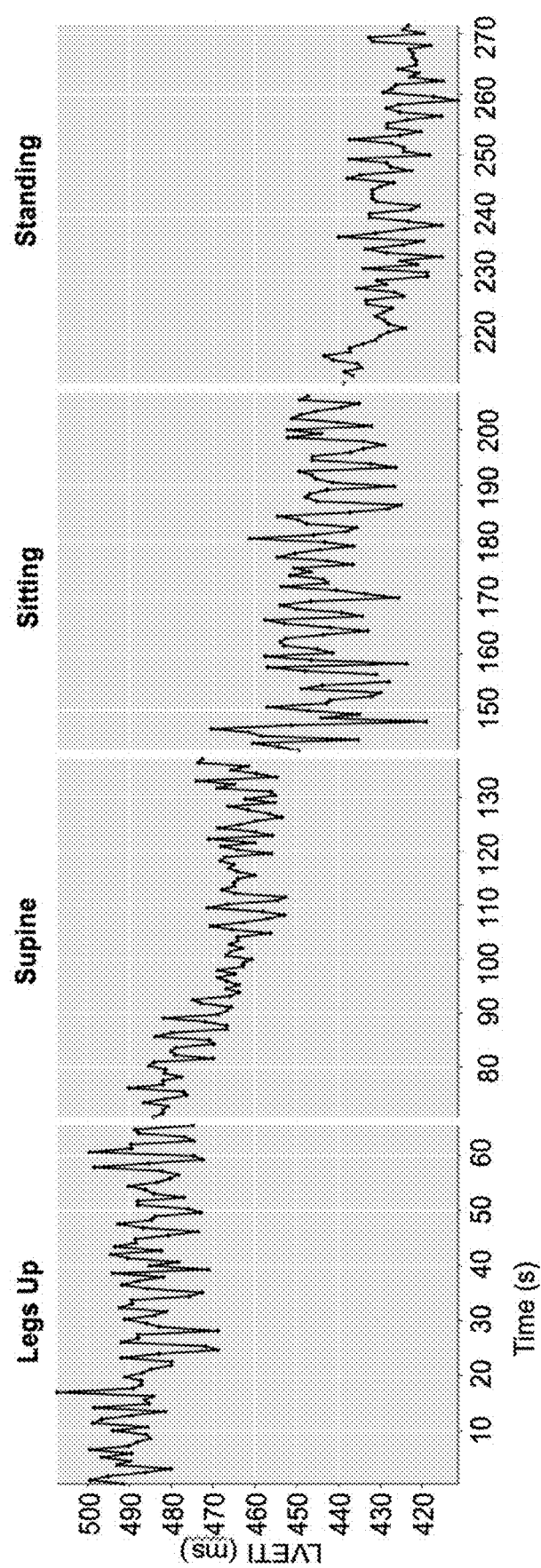
FIG. 36 is the LVET changes observed due to position changes.

Positional Changes. Results from the positional change protocol are shown in FIG. 35 and FIG. 36. The sequence of positional changes will cause a reduction in venous return. As the subject has no heart disease, the overall stroke volume should decrease slightly over the maneuvers. FIG. 35 shows a progressive increase in PAT and FIG. 36 shows a progressive decrease in LVET, both of which are consistent with a decrease in stroke volume, indicating that there is no evidence of fluid overload in this subject.

Example Embodiments

Limitations of current systems. The deployment of a noninvasive hemodynamic assessment system that works reliably and in the presence of known artifacts and noise sources is a significant challenge. Although the system can use other parameters, for the purposes of explaining the embodiments, the following measurements will be used for example purposes: PEP, LVET and pulse amplitude. Conventional configurations will be presented as well as their limitations. This will be followed by several example embodiments that can create a more robust system.

Figures 37, 37A, 37B:
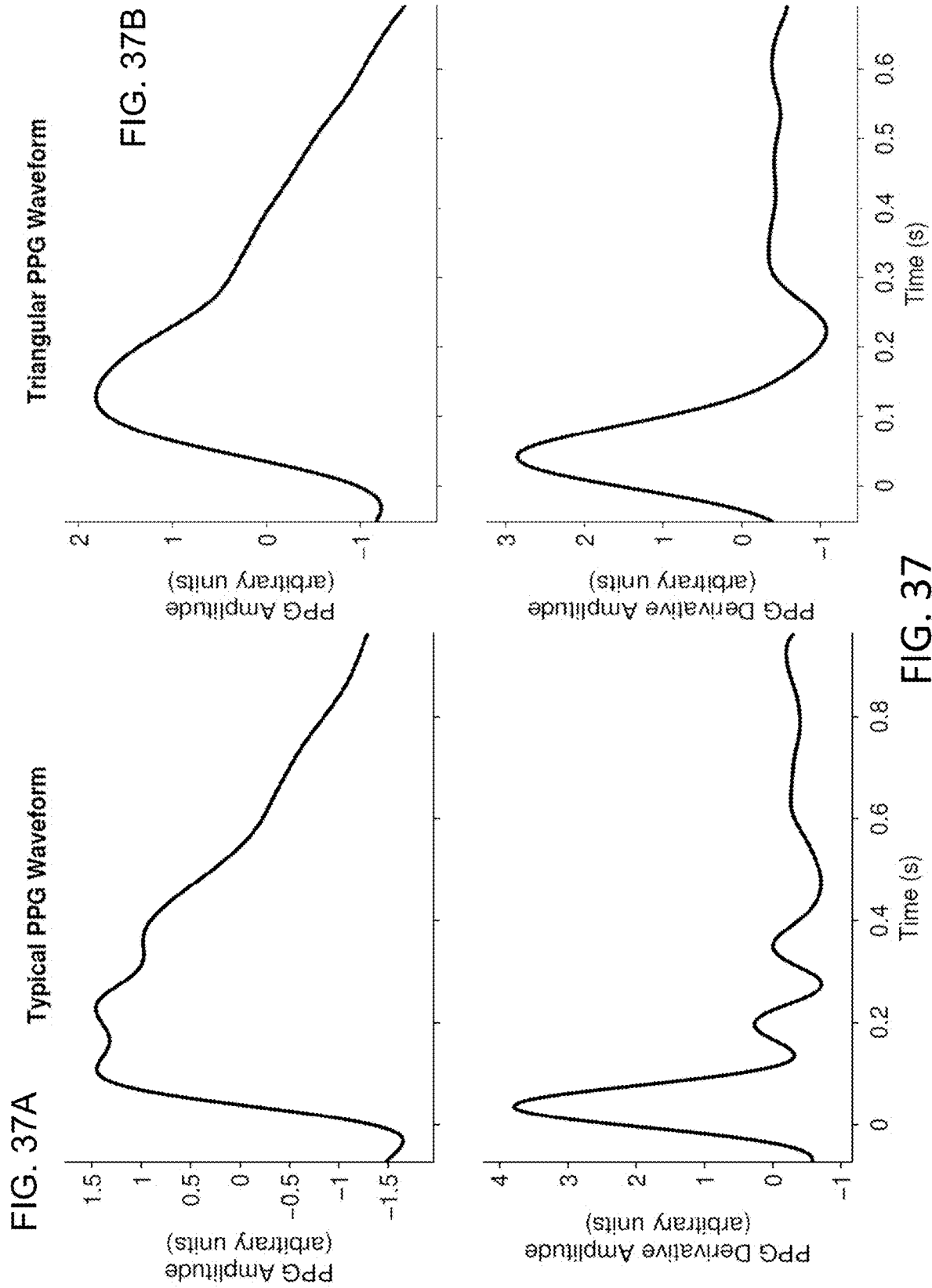
FIG. 37 is a waveform showing poor differentiation of the reflected waves.

A system based upon an ECG and a single PPG has two notable limitations. First, the determination of PEP must be based purely upon PAT measurements with the assumption of constant PTT over the duration of the test. Second, LVET measurement would be determined from PPG pulse waveform typically via a derivative analysis, however this determination is problematic in subjects where derivative features are not easily differentiated. FIG. 37B is an example if such a waveform, hereafter referred to as a "triangular wave" to denote the lack of pulse contour features. In contrast to typical PPG waves (such as that shown in FIG. 37A) where several peaks are clearly evident in the derivatives, in triangular waves, peaks in the PPG derivatives are absent or of low amplitude. Triangular waves are more common in older subjects and dialysis patients, two of the target populations for the system.

Figure 38:
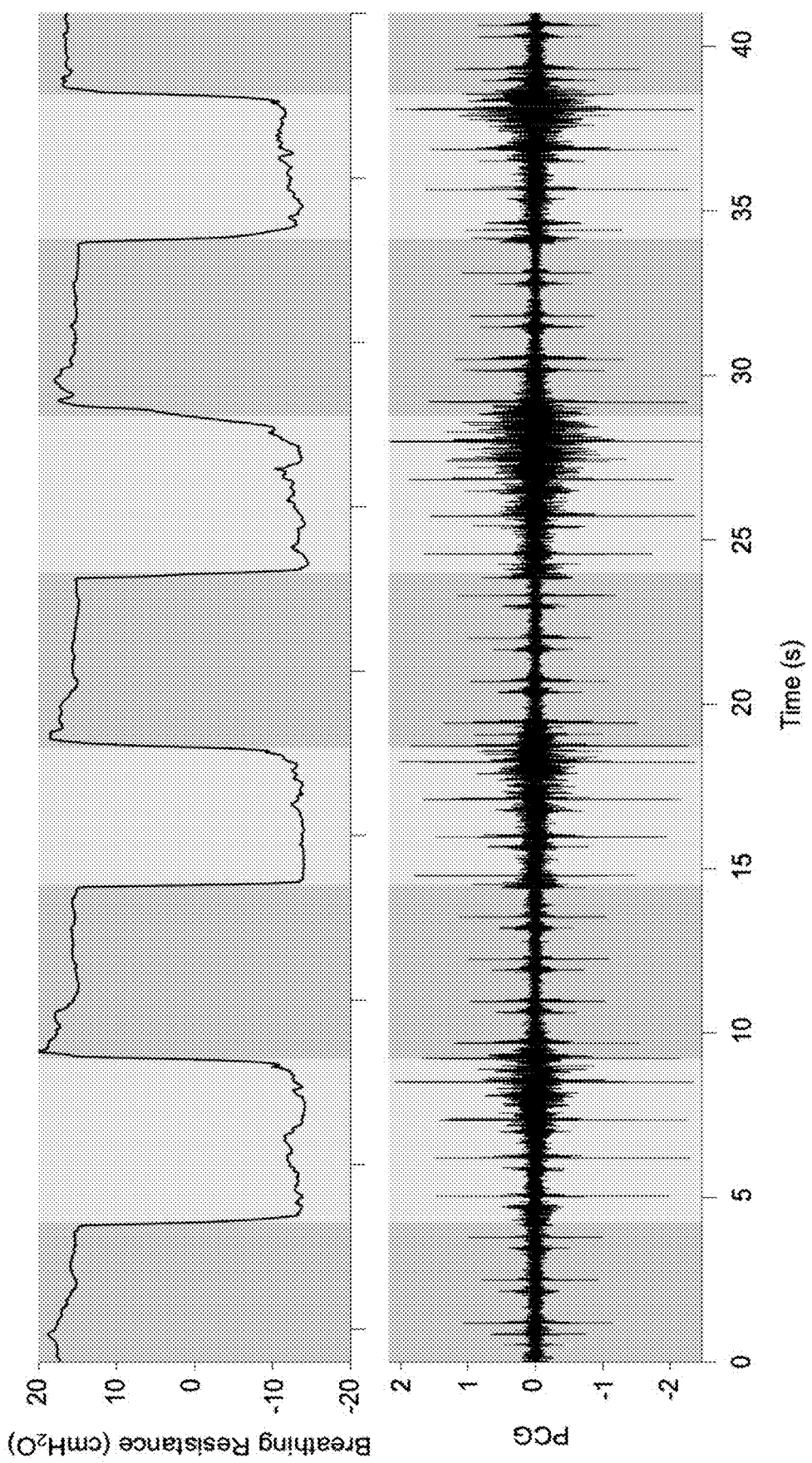
FIG. 38 is a plot showing the noise artifacts during inhale on a PCG recording.

A system based upon an ECG and a PCG also has two limitations. First, identification of the opening of the aortic valve from the PCG alone is challenging because the sound of valve opening is embedded in a series of vibrations associated with blood movement and does not produce a unique signature in the first heart sound. Thus, estimates of PEP and LVET can have inaccuracies. Second, our experience shows that during controlled breathing, inspiration creates a significant degree of noise on the PCG. This noise can limit identification of the heart sounds, and thus determination of PEP and LVET. FIG. 38 is a plot demonstrating the noise artifacts that occur during inhalation. Exhale periods are shaded in dark gray, while inhale periods are shaded with light gray. Noise in the PCG increases notably toward the end of the inhale period and persists through the transition to exhalation.

A system based upon two PPGs and a ECG can be used to help estimate PTT but the estimation must use measured biometric lengths or height assumptions. P. Fung, G. Domont, C. Ries, C. Mott, M. Ansermino, "Continuous noninvasive Blood Pressure measurement by Pulse Transit Time", Proceedings of the 26th Annual International Conference of the IEEE EMBS, September 2004. pp. 738-741. This assumption inherently decreases the accuracy of the system, and the required information can be a nuisance to acquire from a patient.

Improved Embodiments

Combined Instrumentation Processing. The overall performance of the system can be improved by using a novel design with two PPG sensors, an ECG and a PCG with an inventive methodology. To illustrate the value of the invention, the system has the following elements and is used in the following manner: PCG from the heart area, PPG signal taken from the site 1 (denoted as $PPG_1$), PPG taken from site 2 (denoted as $PPG_2$), and an ECG. Combined Instrument Processing capitalizes on the ability to measure LVET from the PCG or PPG and the relationships between time intervals as shown in FIG. 21.

In scenarios where the PCG is too noisy during controlled breathing, the PEP can be determined by considering the relationship between PAT, PTT, and PEP. The initial step is a simple calibration to determine an anthropometric correction factor for PTT signal. The following equations govern the process:

$$PAT_1 = PEP + PTT_{H1} \text{ and} \quad \text{(equation 1)}$$

$$PAT_2 = PEP + PTT_{H2}, \quad \text{(equation 2)}$$

where $PTT_{H1}$ denotes the pulse travel time from heart to site 1 and H2 denotes the travel time from heart to site 2. The difference in travel time between the sites 1 and 2 is:

$$PTT_{12} = PTT_{H2} - PTT_{H1}. \quad \text{(equation 3)}$$

By assuming that $PTT_{H2}$ is proportional to $PTT_{H1}$, we can write:

$$PEP = PAT_2 - [AC] \times PTT_{12}, \quad \text{(equation 4)}$$

where AC is an anthropometric correction factor which relates to the vascular distance between the PPG sites and the pulse wave velocity relationship between the sites. PEP can be measured during quiet breathing directly from the PCG. This value of PEP is used to calculate AC by rearrangement of equation 4. In subsequent noisy periods of the PCG where PEP is not directly accessible, PEP can be determined via equation 4 using the AC value determined earlier.

In patients where the PPG pulse waveform has a triangular waveform and cannot be measured accurately by pulse contour analysis, LVET can be estimated using the relationship between electromechanical systole (EMS) and the STI:

$$LVET = EMS - PEP$$

The EMS is measured based upon the ECG and the second heart sound determined with the PCG. PEP is measured directly by the PCG or with the method shown in equation 4. Thus, determination of LVET and PEP is not based upon pulse contour analysis.

In some situations, there might be noise in a given signal including environmental noise in the PCG, poor or low amplitude pulses, etc. Thus, the ability to have redundant sources of information creates a more robust and reliable system. Additionally, these metric can be observed over time to ensure consistency of the measurements over several respiratory cycles.

Thus, the proposed novel system and processing method addresses two critical issues: (1) triangle waves are not an issue because LVET can be determined from PCG rather than the pulse waveform, (2) PEP need not be determined from the S1 heart sound continuously, and instead can be estimated based on pulse travel times. Since PTT is calculated on a beat-to-beat basis, appropriate compensations can be made for changes in pulse wave velocity due to blood pressure, vascular tone, or others physiological sources and therefore do not adversely impact the accuracy of the measurement.

Continuously Updated PTT Estimate. The system can be simplified to a single PPG, PCG and ECG with some additional assumptions. In this mode of operation, PEP and LVET can be estimated during periods when significant noise is present in the PCG signal by assuming that PTT is relatively constant over the time scale of minutes. First, PEP is determined from the PCG during periods where the patient is breathing quietly or during exhalation segments of the controlled breathing protocol and PTT is calculated as PTT=PAT−PEP. The mean PTT over this period is taken to be constant (PTTc) and subsequent PEP intervals are estimated as PEP=PAT−PTTc. This value of PTTc is used until another PTTc can be determined. A timeline of previous PTTc values can be retained such that the value of a new PTTc is be compared with prior values and an assessment of PTTc deviation calculated. If the deviation is too high the measurement can be repeated. FIG. 40 is a demonstration of the PTTc updating system where the PTTc estimate is updated at points where the PCG enables accurate estimation of aortic opening.

Value of Improved Embodiments. FIG. 39 is an example of the PEP estimation during a controlled breathing protocol where the PCG data contains considerable noise. FIG. 34A shows PEP estimation using the PCG alone; modulations due to respiration are difficult to see given the degree of noise. FIG. 39B shows PEP derived from a combination of PCG and PPG, as PEP=EMS−LVET(PPG). Here, respiratory modulations are visible but still noisy. FIG. 39C uses the Combined Instrumentation Processing method, where the coefficient AC is determined from a minute of normal breathing acquired prior to the breathing protocol. FIG. 34D uses the Continuously Updated PTT Estimate method, where $PTT_c$ is determined from the prior period of normal breathing. The estimated PEP from both the Combined Instrumentation Processing and Continuously Updated PTT Estimate methods shows excellent variation with the respiration cycle and high on a beat-to-beat basis. FIG. 40 shows the same information for LVET estimation. FIG. 40C and FIG. 40D show the strongest respiratory variations, showing the value of the improved embodiments which combine information from the PCG and multiple PPGs and/or incorporate reference information from previously collected data.

Value of Simple system. A simple system of an ECG and PPG has the limitations noted above, but such a system can be used for a number of measurements, specifically the Stroke Volume Phase Relationship. In this test, the subject is subjected a change in preload. If reduced preload results in increased cardiac output as determined based upon PAT or dT13, a phase change relative to normal function then the patient is in an overloaded state. This very important home monitoring test does not require LVET determination or PEP and can be made with accuracy using a simple system. Additionally, the ECG and PPG system can be used for several static measurements. As described above, PAT is a combination of PEP and PTT and can be used a general hemodynamic stability monitor.

Improvements to Heart Sound Discrimination. Heart sound discrimination can be enhanced by removing environmental or physiological noise sources from the PCG signal. Noise sources can be determined via secondary microphones that are positioned close to (but not upon) the chest. This noise signal can then be removed from the primary PCG audio signal using adaptive noise cancellation algorithms, such as those described by Widrow and colleagues. Widrow, Bernard, et al. "Adaptive noise cancelling: Principles and applications." Proceedings of the IEEE 63.12 (1975): 1692-1716. Noise signals can be also learned and removed using blind source separation processing methods, such as independent component analysis (ICA), which separate mixed signals based on assumptions regarding their mutual statistical independence. ICA may be applied to the audio signals acquired with multiple microphones, or to an audio signal from a single microphone in what is known as single channel ICA, as demonstrated by Mijović et al. Mijovic, Bogdan, et al. "Source separation from single-channel recordings by combining empirical-mode decomposition and independent component analysis." IEEE transactions on biomedical engineering 57.9 (2010): 2188-2196. Additionally, standard auscultation by a physician utilizes different placements for the emphasis of breath versus heart sounds. A PCG system comprising multiple microphones can also be used with the techniques above to create improved signal quality.

Example Embodiments

Figure 41:
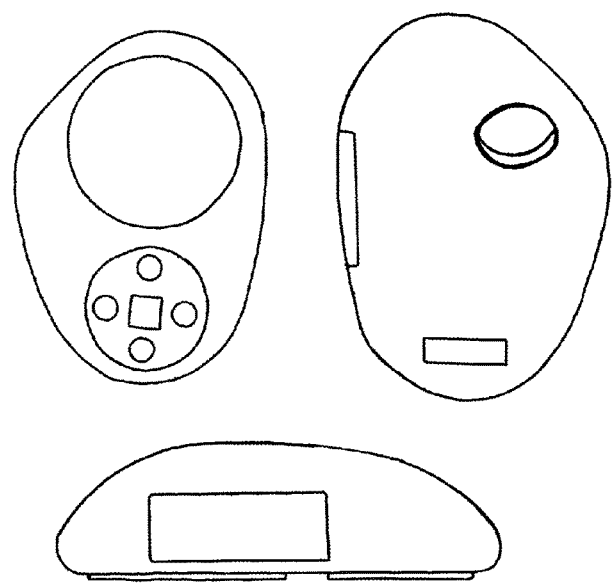
FIG. 41 is a schematic of the operational components of hemodynamic assessment system.
Figure 42:
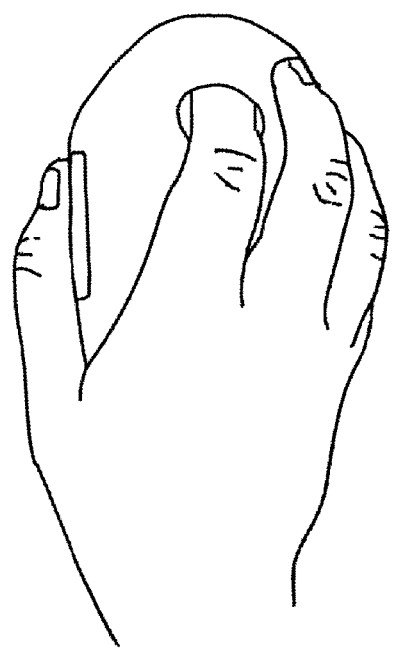
FIG. 42 is a schematic of the subject hand on the hemodynamic assessment system.
Figure 43:
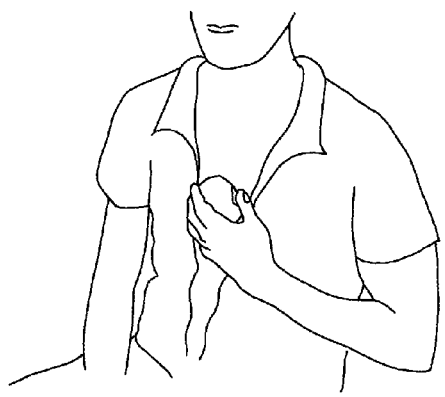
FIG. 43 is a schematic of the hemodynamic assessment system in use.

First Example Embodiment and Operation. The example method and apparatus creates a simple test that enables determination of hemodynamic status and subsequent determination of appropriate treatments for subjects that might be hemodynamically compromised. The device shown in FIG. 41 includes the following measurement systems:
A ECG measurement system, for example from the right thumb
A PPG measurement system, for example on the index finger of the patient,
A PPG measurement system on the bottom of the device for chest PPG measurements; and
A PCG measurement system located on the bottom of the device The device as pictured can resemble the typical computer mouse in terms of size and ergonomics. The patient can place the device over the heart as shown in FIG. 43. The system can ensure that a quality phonocardiogram signal is obtained and provide feedback to the user regarding correct placement of the device. The system can also assess the quality of both the ECG and PPG signal before initiating a measurement. One ancillary benefit of the system is the fact that the hand is located in the same position so hydrostatic differences are minimized. Because pulse arrival time is dependent on hydrostatic pressure, it is desirable to have the hand in the same location for consistency across different measurement periods.

The example embodiment can also utilize different wavelengths for obtaining the PPG signal at the chest and finger. For example, the chest sensor can use a wavelength with high hemoglobin absorbance such as in the 500 to 650 nm range, while the finger PPG sensor wavelength can be in the 800 to 950 nm range.

As presented above, the measurement process can involve simply acquiring these physiological signals for comparison with previously recorded values or with predetermined thresholds. For the purpose of heart failure, monitoring day-to-day trend information in parameters such as LVET, PEP, PEP/LVET, or PAT can be valuable for accessing hemodynamic congestion.

If a hemodynamic assessment with greater fidelity is desired, the test procedure can involve a defined perturbation test. Such a test can involve a controlled breathing test at one of more levels of resistance. The previously presented data demonstrates the effectiveness of two breathing levels to include the possible use of zero resistance at a paced breathing rate of 6 breaths per minute. Instructions on the breathing test can be displayed on a secondary monitor or communicated verbally to the patient. Given the importance of respiratory phase transition times as well as adherence to the protocol, the controlled breathing device can communicate with the hand held measurement device or a remote data acquisition device.

A perturbation test can also include patient positional changes, singularly or combined with the controlled breathing test. The patient can move from the supine to seated to the standing position or other variances. Other possible variances include leg raises, etc. as one of skill in the art will appreciate; the perturbation test simply needs to create a change in venous return that can be repeated.

The resulting measurement information can be processed on the device and displayed to the subject. An alternative scenario involves transfer of the data to a remote data processing and storage site. Such a centralized and connected site can process the information, generate results and send the results to the patient as well as others such as health care providers.

The system shown can also have components of an inertial measurement unit (IMU) to facilitate determination of the subject position as well as changes in position. Much like the breathing test, understanding the time of a given positional change as well as the speed of the change can be important from a repeatability perspective. For example, the IMU can be used to determine the degree of tilt that is present when the subject is in the sitting position. The system can communicate with the controlled breathing system (not shown) as needed based upon the clinical situation. The system has the functional capability to enable hemodynamic assessment for heart failure, avoidance of hypotension during dialysis, and for patient assessment in the ambulatory clinic, urgent care, emergency department, ICI and operating room.

Figure 44:
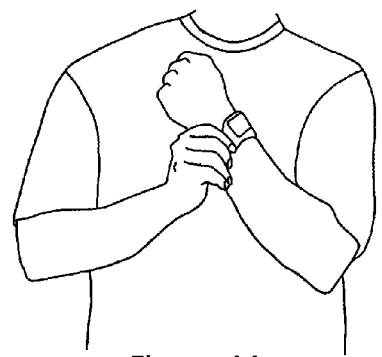
FIG. 44 is a schematic of a hemodynamic assessment system using a watch.

Second Example Embodiment and Operation. A simplified system can be based upon only an ECG and PPG signal. The system can be as simple as a watch and ECG measurement band as shown in FIG. 44. Multiple companies make pulse detection systems that work on the wrist for the determination of heart rate. These systems can be used to determine pulse arrival time at the wrist while the subject ECG is obtained. Additionally, many watches have accelerometer and gyros (IMUs) so the motion of the patient can be recorded. The patient can do a controlled breathing protocol or a position location protocol. The system can be used for point measurements and also for trend monitoring (e.g., over multiple days or during a dialysis session). Because PTT is influenced by hydrostatic measurement, awareness of arm location can be important. The subject can simply locate the arms at heart level for the duration of the measurement.

Given the size and convenience of this system, a patient can sleep with the watch system attached and make measurements prior to getting out of bed. The measurement process can be as simple as awakening, making a measurement, sitting on the side of the bed for a brief time, and then rising to a standing position.

The system can communicate with the controlled breathing system (not shown) as needed based upon the clinical situation. Additionally, the system can communicate with a PCG system (not shown) as required.

Figure 45:
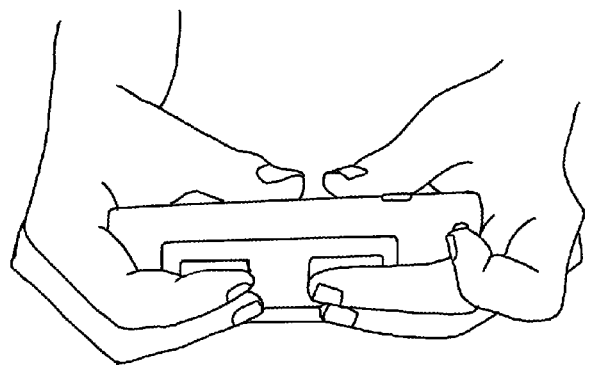
FIG. 45 is a schematic of a hemodynamic assessment system using a mobile phone.

Third Example Embodiment and Operation. This example embodiment leverages the general capabilities resident in a cellular phone, including a camera, IMU, and data communication capabilities. FIG. 45 shows the device in operation with the ECG obtained from the finger and a finger placed over the camera for pulse detection. The use of a mobile phone has a number of advantages including integrated communication and display capabilities.

The system can communicate with the controlled breathing system (not shown) as needed based upon the clinical situation. Additionally, the system can communicate with a PCG system (not shown) as required.

Figure 46:
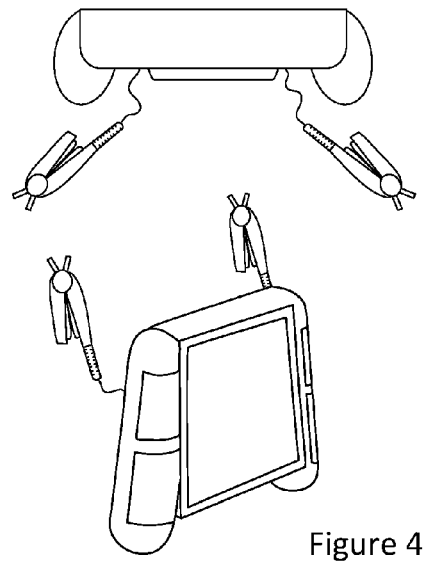
FIG. 46 is a schematic of a hemodynamic assessment system using a dedicated device.

Fourth Example Embodiment and Operation. An example embodiment of the system is shown in FIG. 46 as a dedicated measurement system. The device contains one or more PPG measurement devices and a screen to communicate with the patient. The handles of the device enable ECG measurement. The system can communicate with the controlled breathing system (not shown) as needed based upon the clinical situation. Additionally, the system can communicate with a PCG system (not shown) as required.

Fifth Example Embodiment. An example embodiment of the system is shown in FIG. 47. This example system utilizes a PPG measurement device located on the ear with an ECG measurement system on the chest or other locations. (not shown). This system can be used with or without resistance breathing or other changes such a passive leg raises. The example embodiment shown in FIG. 47 can also utilize different wavelengths for obtaining the PPG signal. For example, the ear sensor can use a wavelength with high hemoglobin absorbance such as in the 500 to 650 nm range, while the transmission wavelength can be in the 800 to 950 nm range.

Sixth Example Embodiment. Two PPG measurements and an ECG can be obtained with the use of a standard mobile phone when equipped with a ECG device as described in U.S. Pat. No. 8,301,232. The phone can be placed face down or held against the chest of the patient. The front facing camera can record the chest PPG, while the rear facing camera records the finger PPG. The ECG measurement can be made from the back of the phone as shown in FIG. 48.

Seventh Example Embodiment. The above system can be used to acquire a head or face based PPG, a finger PPG and a ECG. Noncontact PPG measurements can be made using the face or hand and enable additional flexibility in the measurement process, as shown in FIG. 49.

Eighth Example Embodiment. Additional information in the form of a seismocardiogram (SCG) can be obtained with a standard mobile device. The device is placed on the chest and SCG measurements are made concurrently with obtaining chest PPG data. Because the device will be sensitive to movement, contact between the hand and the device is likely to create noise artifacts. Thus, a second PPG can be obtained by holding the hand above the camera, as illustrated in FIG. 50. Other physiological measurements such as PCG can be recorded via the breathing device or another device. The SCG measurement enables calculation of PEP and LVET, while the concurrently obtained PPG provides additional valuable information.

Ninth Example Embodiment. The mobile system used above can be used to acquire a PCG signal directly or via an additional attachment as shown in FIG. 51. The attachment can be a diaphragm to improve detection of heart sounds while using the devices microphone or a separate microphone and system for heart sound detection. The system can be held on the chest while a PPG and ECG signal are obtained from the holding hand. The secondary camera on the phone can make PPG measurements from the throat or head based upon alignment (as shown) or from the hand holding the device.

Controlled Breathing Device. FIG. 52 is a schematic illustration of a position determination system FIG. 53 shows a subject engaged in controlled breathing. Device 4101 is an example of a resistance breathing device. The device can take a variety of forms depending upon the exact resistance breathing protocol defined. A mask or mouth piece system can be used. As illustrated, the subject will breathe through the breathing device 4101 that creates one or more changes in intrathoracic pressure. As previously noted the protocol can include but is not limited to one of the following: inhalation resistance, exhalation resistance, or both, and resistance breathing can include normal breathing, paced breathing, or event based breathing. Event based breathing is where the subject does a particular resistance activity followed by a recovery period.

Communication of Respiratory Phase. As described above, the determination of respiratory phase can be important from a processing perspective. The breathing device can communicate with other elements of the system via circuitry, antennas, wireless communication (typically via electro mechanical means) such as Bluetooth etc. However, such elements can add substantial cost and complexity. The phase of the breathing cycle, the duration of the breathing cycle, and adherence to the breathing cycle can be communicated to other system components through the use of an air movement sensor that generates vibrations or sound, specifically sounds removed from the heart sounds including as an example ultra-sonic sounds. The controlled breathing device can have a sound generation device that is activated during exhale or inhale. The mechanism can operate in a manner similar to a harmonica for example. The typical harmonica is a free reed wind instrument. A harmonica reed is a flat elongated spring typically made of metal but can be plastic. The reed vibrates due to air movement over the reed. An inhalation reed and exhalation reed can be tuned to individual pitches that do not impact system performance. Specifically, the reeds can create a pitch distinct from heart sounds, e.g., ultra-sonic waves or pitches that are easily heard by the user for audio feedback during use.

In practice, the device can be configured to only generate sound after the resistance threshold is satisfied and air is moving out of or into the device. Thus, the generation of sound is specific for air flow and can be used to determine the start and stop of exhale with high resolution. In testing, it can be advantageous from a repeatability perspective to have the patient breath at a constant flow rate. As the intensity of sound is proportional to air flow, this creates an inherent measure of consistency. Inhale and exhale can be differentiated by generating a distinct sounds or frequencies associated with inhale or exhale. Thus, the system can determine inhale and exhale by the frequency of sound generated. The sound generated can be either in the audible range or at a frequency above human hearing, defined as ultra-sound. For patient convenience, avoidance of ambient noise, and separation from the heart sounds, the use of ultrasonic frequencies can be desirable. Additional sounds associated with the breathing system can be used in a similar manner. For example, the opening of the exhale threshold valve creates a distinctive spike on the PCG signal as observed in testing.

The sounds generated with inhalation and exhalation can be detected by a microphone with appropriate sensitivity or by the phonocardiogram. For example, the mobile device of example embodiment #3 can record the breathing system sounds for determination of start and stop times as well as general compliance with the test. Example embodiment #1 can be equipped with a microphone or it can use the PCG system.

In some test situations, it is desirable to use two pressure levels. The different pressure levels could use two separate devices or a single device where the change in pressure also changes the sound generation device. For example, the rotation of components within the device can also be used to change the frequency generated by the air flow movement sensor. Thus, the airflow movement sensors are sensitive to threshold pressure, flow, and flow rate based upon the frequency and intensity of sound produced.

Additional capabilities can be added to the controlled breathing device for communication of this information via electromagnetic communication as well as sound based communication via classic modem techniques for example. The information communicated can include but is not limited to the following time varying information: pressure, air flow, tidal volume, and respiratory rate.

In some of the embodiments above, a camera or a mobile device camera is used for PPG measurement. The same camera can be used to detect visual signals associated with inhalation and exhalation. In a simple form, a small streamer or pinwheel-like device can provide information regarding the presence of flow as well as the consistency of flow.

The capabilities of the controlled breathing device can be expanded to include a measure of airflow direction and speed. Multiple anemometer methods can be used such as a rotating vane anemometer and as a hot wire anemometer. The determination of air speed or flow in combination with time enables the determination of tidal volume. Hager et al. discusses four different methods for making such a measurements and multiple approaches exist. Hager, David N., et al. "Four methods of measuring tidal volume during high-frequency oscillatory ventilation." Critical care medicine 34.3 (2006): 751-757.

The above embodiments are intended to be examples but one of ordinary skill will appreciate that many different combinations are possible depending upon the hemodynamic assessment needed and the clinical situation.

Variable Pressure System. FIG. 54 shows a variable pressure system. The system has the ability to change the controlled breathing pressure during operation. Specifically, the system can allow the patient to start the study with no or minimal resistance but with a defined breathing rate. The system can then add resistance in a defined manner, in a linear, or stepped fashion for example. Resistance can be added on the inhale only, exhale only or both. FIG. 54 is a schematic representation of a subject holding the device. The system contains a ECG detection system located under thumb, a PPG system (not shown), a method for determining flow, and a method of changing breathing pressure. The breathing device has a disposable component that can be changed when used on different patients. The device can contain an air flow measurement device to measure direction and speed of flow, such as a hot wire anemometer. A hot wire anemometer uses a very fine wire (on the order of several micrometres) electrically heated to some temperature above the ambient. Air flowing past the wire cools the wire. As the electrical resistance of most metals is dependent upon the temperature of the metal, a relationship can be obtained between the resistance of the wire and the flow speed. The resistance used in the controlled breathing can be changed by the device or changed manually. The system can be equipped with communication capabilities such that information is transfer from the device to a central device, the internet or the patient's electronic medical record.

Position Determination. Due to hydrostatic pressure influences and blood volume distribution changes due to body position, the ability to determine sensor position and body pose are important elements of the system. For purposes of explanation, body position will include the general ability to access body pose and sensor position, or either measurement independently. A "position sensor" comprises any device or system that can indicate the absolute or relative position of the position sensor or another device or system. For example, a position sensor for a PPG device can indicate the position of the PPG device relative to the heart, in the vertical dimension or in other dimensions. A "pose sensor" comprises any device that can indicate the relative position, angles, or both of various parts of the body. There are many approaches for the determination of position and pose but the methods can be viewed as falling into three general categories: (1) external assessment, (2) attached assessment and (3) combination systems.

External Position Assessment System. External assessment is similar to observing a person and determining their body position, but the process is implemented via machines. The position of the subject can be determined with the use of a conventional camera via the use of vision based activity recognition. Vision based activity recognition is the process of labeling video or camera information containing human motion with action, activity or position labels. The area of human action recognition is closely related to other lines of research that analyze human motion from images and video. The recognition of movement can be performed at various levels of abstraction. Different taxonomies have been proposed by Poppe in the article titled "A survey of vision-based human action" provides an exceptional overview of the general area of activity recognition. Poppe, Ronald. "A survey on vision-based human action recognition." Image and vision computing 28.6 (2010): 976-990. In the article, Poppe adopts the hierarchy used by Moeslund et al.: action primitive, action and activity. Thomas B. Moeslund, Adrian Hilton, Volker Krüger, A survey of advances in vision-based human motion capture and analysis, Computer Vision and Image Understanding (CVIU) 104 (2-3) (2006) 90-126. An action primitive is an atomic movement that can be described at the limb level. An action consists of action primitives and describes a, possibly cyclic, whole-body movement. Finally, activities contain a number of subsequent actions, and give an interpretation of the movement that is being performed. For example, "left leg forward" is an action primitive, whereas "running" is an action. "Jumping hurdles" is an activity that contains starting, jumping and running actions.

The hemodynamic assessment system can determine body position using a variety of vision capture technologies to include both video and cameras. It should be noted that infrared cameras are also applicable. Additionally, the system may utilize a fisheye lens, to completely capture the scene and be less sensitive to alignment issues. The system can also use structured light or 3D camera system such as the Microsoft Kinect, Orbbec Astra, Intel Realsense, Stereolabs Zeb stereo camera and others. These systems operate by different principles but are able to measure 3-dimensional space. Multiple systems are capable of doing skeletal tracking for the creation of a skeleton stick figure that captures the "skeletal" location of the subject to include hands and fingers. Han et al. Han, Fei, et al. "space-time representation of people based on 3d skeletal data: a review." arXiv preprint arXiv:1601.01006 (2016). have recently written a review article that presents a comprehensive survey of existing space-time representations of people based on 3D skeletal data, and provides an informative categorization and analysis of these methods from the perspective of: information modality, representation encoding, structure and transition, and feature engineering.

In addition to the use of vision based activity recognition, face detection can be a valuable tool in the processing method. Face detection is a computer technology being used in a variety of applications that identifies human faces in digital images. In 2001, Paul Viola and Michael Jones invented a new framework for detecting arbitrary objects and refined it for face detection. The algorithm is now known as the Viola-Jones framework. The Viola-Jones method has a very high accuracy rate and does not require significant processing power. As used in the invention, face detection can locate the face in the image and provide information associated with body pose and sensor location relative to the face.

In summary, multiple hardware options exist for effectively capturing image information for determination of body position to include body pose and senor location. Such systems can be located in a central data transmission system, a charging system or a device with a designated purpose.

Figure 3:
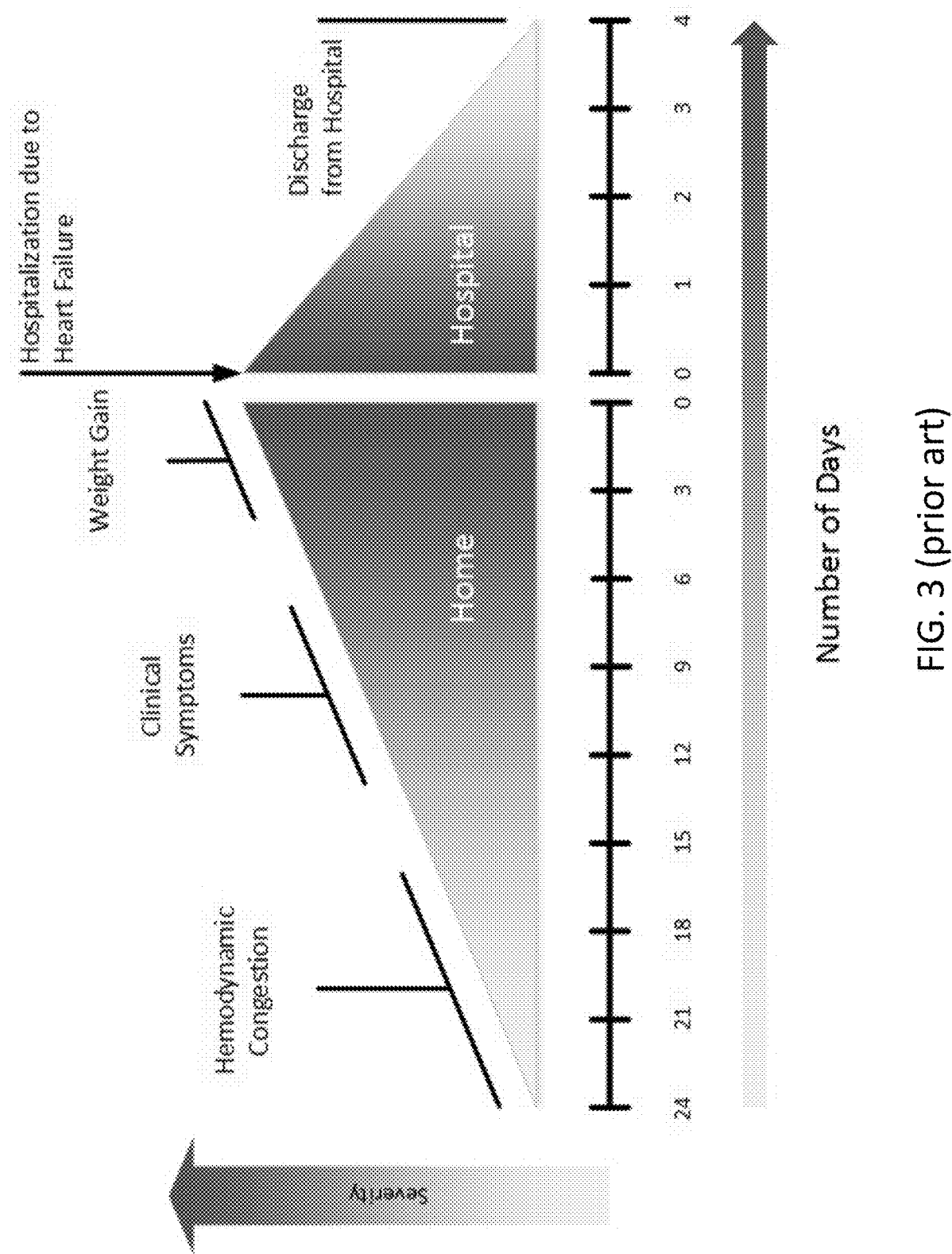
FIG. 3 is a schematic illustration of the clinical course of hemodynamic congestion in heart failure.

Attached Position Assessment System. Body position assessment by attached assessment represents a broad category for position assessment and is based upon sensors attached to the individual. The process is akin to determining one's (self) position based upon sight, balance and physical motion. Height differences can be determined using a manometer type approach when the pressure exerted by a fluid column can be used to determine height changes. In addition to fluid pressure measurements, recent developments in motion tracking has created a variety of effective body position sensing methods. For example, activity tracking in the elderly as well as motion tracking in sports have spurred the development of systems and methods in this area. For example, Najafi et al. demonstrated a new method of physical activity monitoring that demonstrated the ability to detect body postures (sitting, standing, and lying) and periods of walking in elderly persons using only one kinematic sensor attached to the chest. Najafi, B., Aminian, K., Paraschiv-lonescu, A., Loew, F., B??la, C. J., & Robert, P. (2003). Ambulatory system for human motion analysis using a kinematic sensor: Monitoring of daily physical activity in the elderly. IEEE Transactions on Biomedical Engineering, 50(6), 711-723. http://doi.org/10.1109/TBME.2003.812189. Other examples include position determination for EKG monitoring. Jason et al. demonstrated the ability to determine a patient's position (lying down, sitting, standing, or changing from one position to another) during Holter monitoring for the evaluation of common symptoms such as dizziness, palpitations, and syncope. Akhtar, S., Matei, V., London, M. J., & Barash, P. G. (2011). Electrocardiographic Monitoring. Kaplan's Cardiac Anesthesia: The Echo Era, 60208, 452-465. http://doi.org/10.1016/B978-1-4377-1617-7.00017-0. IMU system have also been used to track arm motions in space for sports and physical exercise. These systems may use a sequence of events to confirm the body position. For example, the subject may do a test in the seated position and then stand. The transition from sitting to standing can be used to evaluate chest position in the seated position. FIG. 3 in the Najafi article includes descriptive information on the process of using two positions for accurate body position assessment.

The ability to determine the location of an object on the body or a sensor on a finger can be done via a camera and IMU data. Several variances exist in this approach, but the best known is Tango (formerly named Project Tango in-testing). Tango is a technology platform developed and authored by Google that uses computer vision to enable mobile devices, such as smartphones and tablets, to detect their position relative to the world around them without using GPS or other external signals. Project Tango is able to determine a device's position and orientation within the environment. The software works by integrating three types of functionality: (1) motion-tracking: using visual features of the environment, in combination with accelerometer and gyroscope data, to closely track the device's movements in space, (2) area learning: storing environment data in a map that can be re-used later, shared with other Project Tango devices, and enhanced with metadata such as notes, instructions, or points of interest and (3) depth perception: detecting distances, sizes, and surfaces in the environment. Together, these generate data about the device in "six degrees of freedom" (3 axes of orientation plus 3 axes of motion) and enable the position of the device to known in absolute coordinate space.

Such a position sensor can, for example, be part of the PPG system and determine the position changes from the storage cradle to placement on the finger. Such information can be used to ensure that PPG senor is placed in the same location for each measurement. A similar scenario exists for body pose where the system can determine body pose. Such a system can be used to determine relative position as well as absolute position relative to the floor, heart or other body locations.

Sound Based Position Assessment. In addition to dimensional determinations of position, the location of a sensor relative to the heart can be done by accessing the magnitude of the heart sounds. If the sensor is located significantly above or below the heart, the magnitude of the sounds is diminished significantly. Thus, the magnitude of the heart sounds can be used as a mechanism to ensure that the PPG sensor is in the correct position relative to the heart.

Breathing Movement Based Position Assessment. The location of the sensor can also be assessed by the movement of the sensor due to cardiac activities or breathing activities. The beating of the heart creates vibrations and movements that can be assessed by ballistocardiography (BCG) and seismocardiography (SCG) systems. Additionally, breathing motion can be used to access the location of the sensor as chest movement is different than abdominal motion and varies across the chest wall.

The above body position system for sensor position and body pose system can be located in the various hardware embodiments previously discussed. For example, embodiment #1 could have a camera as part of the watch system. The camera and IMU system in the watch system can determine sensor position relative to the heart based on prior motion as well as test specific motion. Embodiment #2 contains a PPG and IMU, so several methods of position assessment are possible.

Motion Tracking Position Assessment Systems. Combination systems involve an external camera for scene capture and markers places on the subject. Optical-passive approaches use retroreflective markers that are tracked by infrared cameras and represent the most flexible and common method used in motion tracking industry. Optical-active techniques use LED markers. Active or passive markers can be placed in the sensor systems or on the subject as needed to facilitate body position determination.

Combination System. The ability to combine elements of the various body position systems enables the creation of user-friendly but accurate position system. For illustration purposes consider FIG. 52 which shows a position determination system. A subject is seated with arms crossed and the sensor positioned over the heart as shown in FIG. 43. Electronic system 5101 displays instructions for the subject and has a camera in the top. In use, the camera obtains images from the locations defined by rays 5102 and 5103. The information from location 5102 is used for face detection followed by pupil detection and distance determination. This anatomical feature is then used to determine the distance to the electronic device 5101. The information from the location defined by rays 5103 contains an image of the sensor. The sensor has a two blinking LEDS of different colors and at defined on-off frequencies. The different colors enable determination of orientation of the sensors and the defined blink frequencies facilitate location determination. The geometric relationships between the eyes, the eye location, the sensor location, and the distance between the sensor LEDS enables determination of the distance between the eyes sensor and the ability to determine if the body position or pose is vertical. The above description is a singular example of how body position to include sensor position and body pose can be determined by the elements of the invention.

System Use Examples. The following use cases are provided so that the value and inventive nature of the system can be appreciated. The three use cases presented comprise an urgent care scenario, an ambulatory patient with heart failure, and the dialysis clinic.

Urgent Care. This scenario comprises a patient presenting at an urgent care clinic with nausea and diarrhea that has persisted for several days. The patient has a normal blood pressure but the physician is concerned with possible dehydration. The system described in FIG. 54 provides a convenient and easy method to perform a hemodynamic assessment in such a scenario. The following is an example use scenario but one can appreciate many variances associated with the use of such a system. The device is provided to the patient, and ECG and PPG signals of sufficient quality are confirmed. The subject begins breathing at a defined rate of 6 breaths per minute. The subject continues to execute the breathing protocol until a constant breathing pattern is obtained as assessed by breath timing and air flow characteristics. Based upon testing, most individuals need time to get comfortable with the system. The system can provide feedback to the user as needed. The base condition has a low level of resistance at 2 cm H2O on both inhalation and exhalation. Following procurement of a consistent breathing profile, the system adds some inhalation exhalation resistance in a slow and systematic manner. Resistance can be added at a rate of 5 cm H2O per minute or at a rate of 5 cm H2O per 6 breaths. The result is a 3-minute test that creates continuous curve of changing intrathoracic pressure with a maximum exhale pressure of 15 cm H2O. If instabilities in the measurements are observed, the system can prompt the subject to repeat the measurement/breath at the prior pressure.

Figure 55:
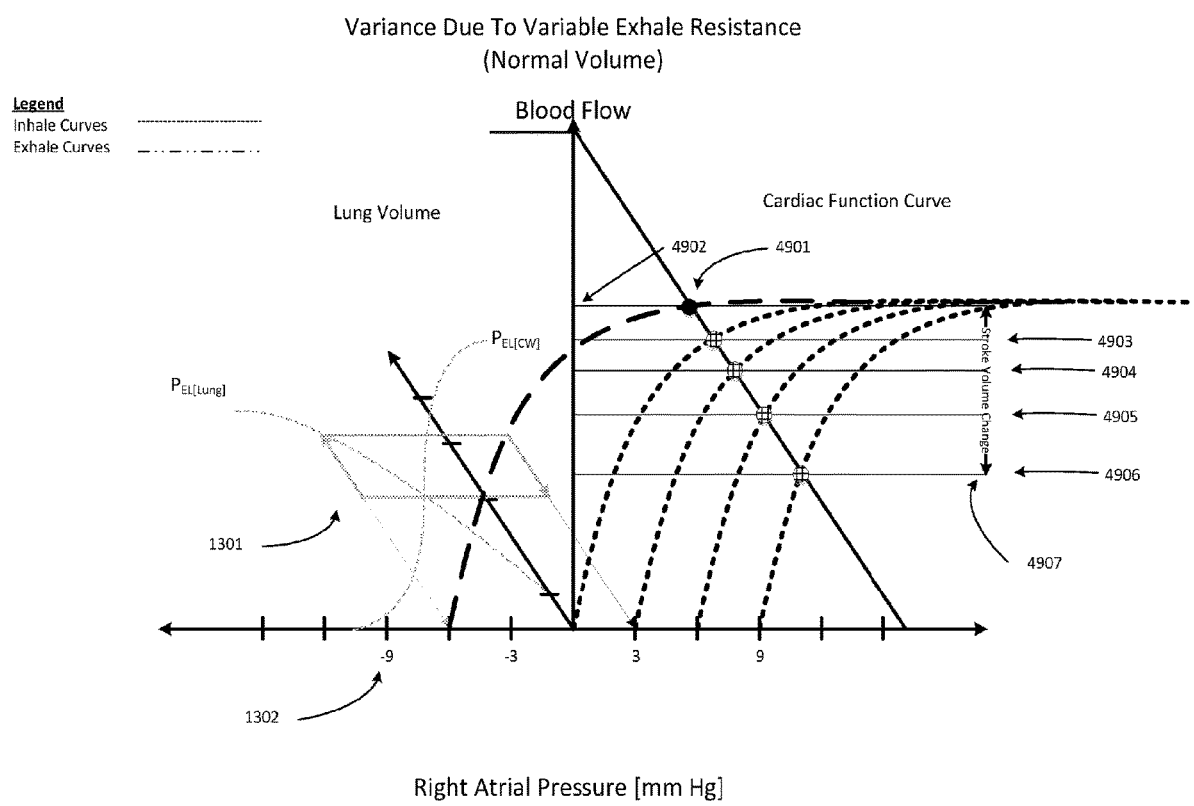
FIG. 55 is a schematic representation of Guyton representation of a variable pressure test at normal volume.
Figure 56:
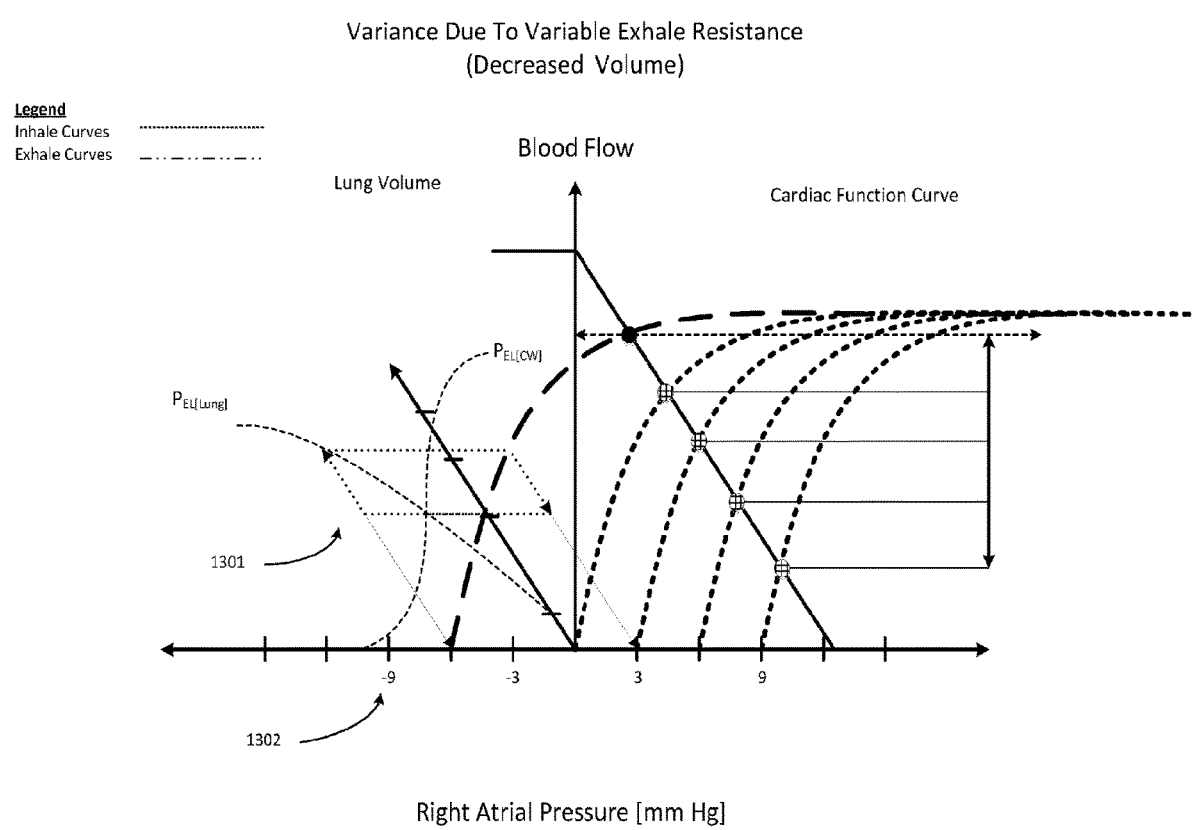
FIG. 56 is a schematic representation of Guyton representation of a variable pressure test at decreased volume.
Figure 57:
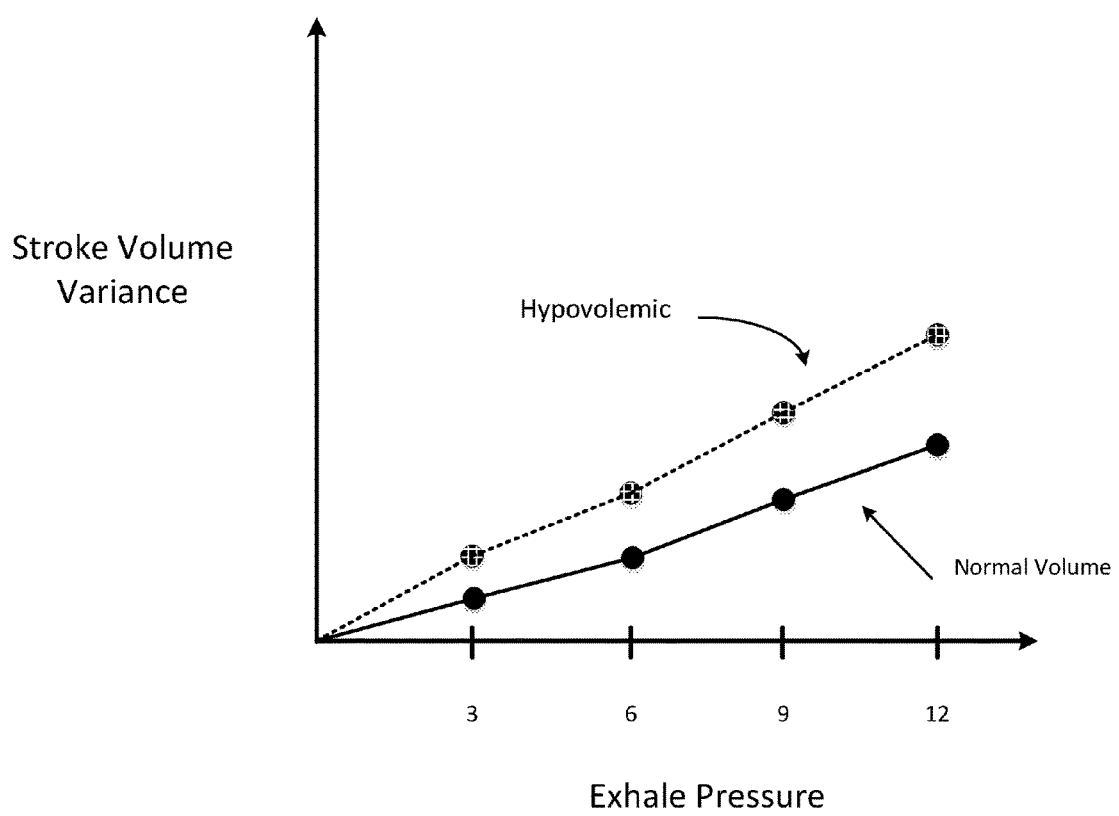
FIG. 57 is a schematic representation of response difference due to a variable pressure test.

The value of the above method, in addition to patient convenience, can be shown via use of the Guyton curves previously presented. FIG. 55 is a combined heart-lung graph showing variable exhalation pressure under a condition of normal volume. 4901 represents the cardiac operating point for the inhale condition which remains fixed over the test. The resulting cardiac output is shown on the y-axis as point 4902. Line 4903 shows the cardiac output during the first exhale pressure. 4904 is the second exhale pressure, 4905 the third and 4906 the fourth. The resulting change in stroke volume is illustrated by arrow 4907. With increasing exhalation pressure, the change in stroke volume increases. Because the illustrated subject is on a relatively flat portion of the Frank-Starling curve the changes in stroke volume and the resulting variance in stroke volume is moderately small. In contrast, FIG. 56 is a combined heart lung-lung graph showing exhalation pressure under a decreased volume condition. The intersection point between the venous return curve and the cardiac function curve occurs in an area of increased slope. This interaction creates larger changes in stroke volume for the same amount of intrathoracic pressure change. FIG. 57 shows the variance in stroke volume versus the change in intrathoracic pressure for the two conditions illustrated. The slope of the curve generated in the hypovolemic cases is greater than the normal volume condition.

The above figures demonstrate the use of increasing exhalation pressure while maintaining inhalation pressure. The use of an asymmetric profile has the advantage of minimizing venous collapse and creating a more continuous response curve.

Note that the above protocol can be stopped at any point once a definitive determination of volume responsiveness has been obtained. For example, in a subject that is hypovolemic, larger stroke volume changes will be observed so a shorter protocol might be used. The ability to start with a low resistance value and only increase resistance pressure until a measurement results is obtained creates a subject friendly system, especially when compared with current technology that involves a ventilator and invasive arterial line.

Figure 58:
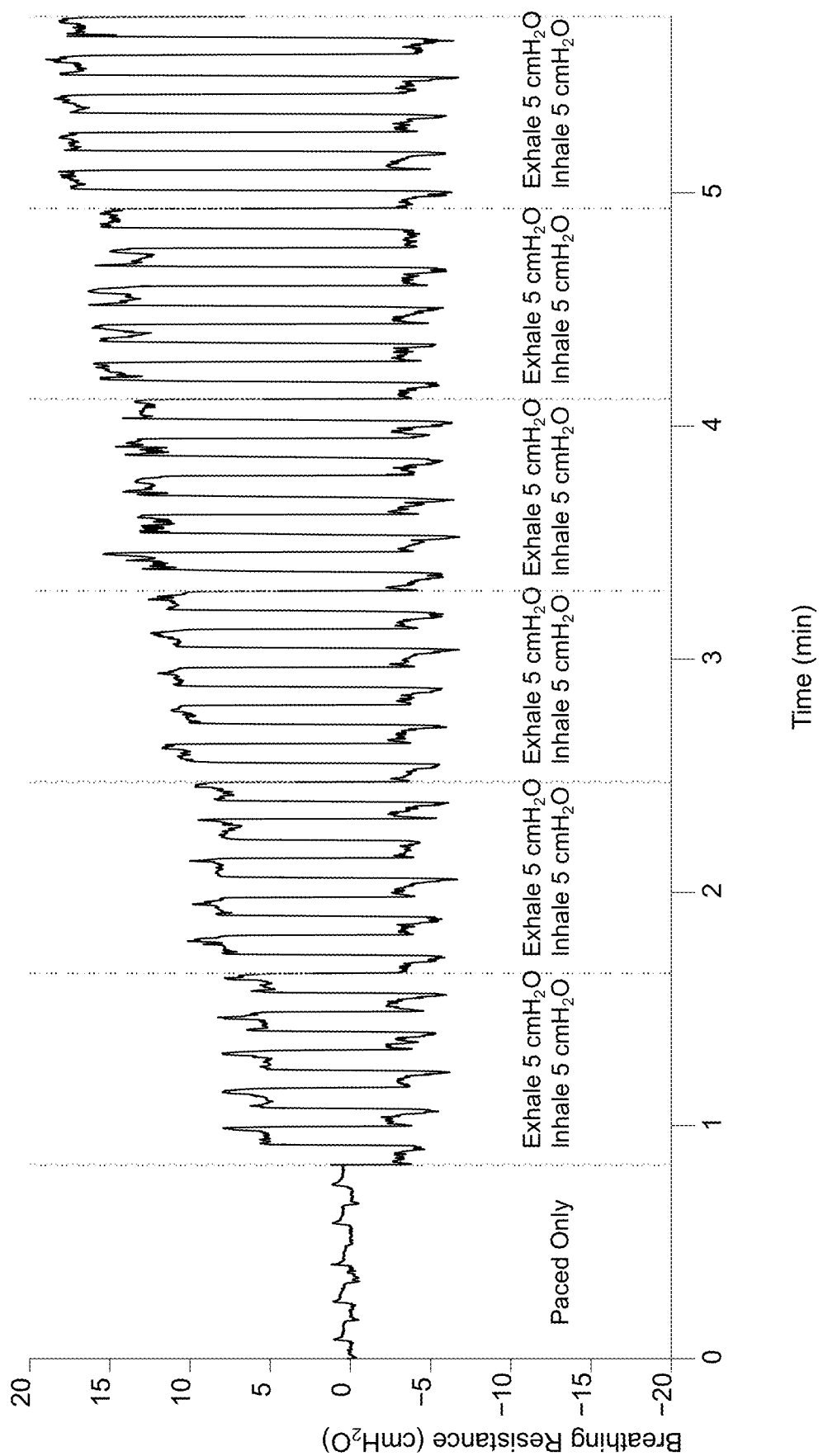
FIG. 58 is a plot of the pressure profile used during testing.

The above method was validated during a lower body negative pressure test. Specifically, the subject was subjected to 4 different levels of lower body negative pressure to create different levels of circulating volume. The levels used were 0, −15, −30, and −45 mmHg. In the test conducted, the controlled breathing protocol used was 6 breaths per minute, starting with no resistance (paced breathing only), then adding 5 cmH$_2$O inhale and 5 cmH$_2$O exhale of resistance and subsequently increase of exhalation resistance 2 cmH$_2$O after several breaths. FIG. 58 shows an example of the breathing sequence.

Figure 59:
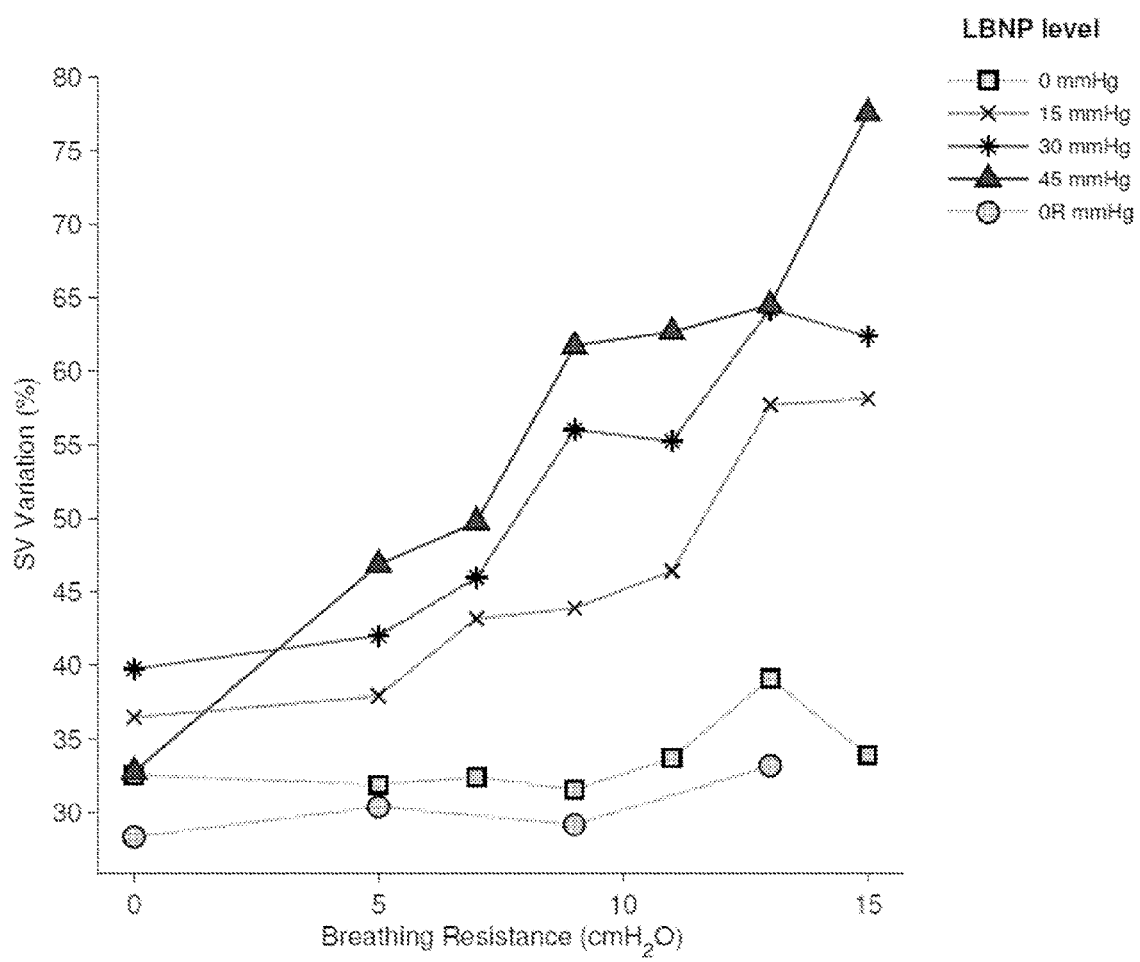
FIG. 59 is a schematic representation of the stroke volume results obtained via a variable pressure test.

FIG. 59 demonstrates the value of the resistance breathing protocol approach by showing the relationship between exhalation resistance and % changes in stroke volume variation as a function of LBNP. The plot shows the value of using several resistance pressure levels for testing because the systematic changes provide definitive information regarding the volume state. The curve labeled "0R mmHg" shows the response after the LBNP has been released and the subject is in recovery.

Figure 60:
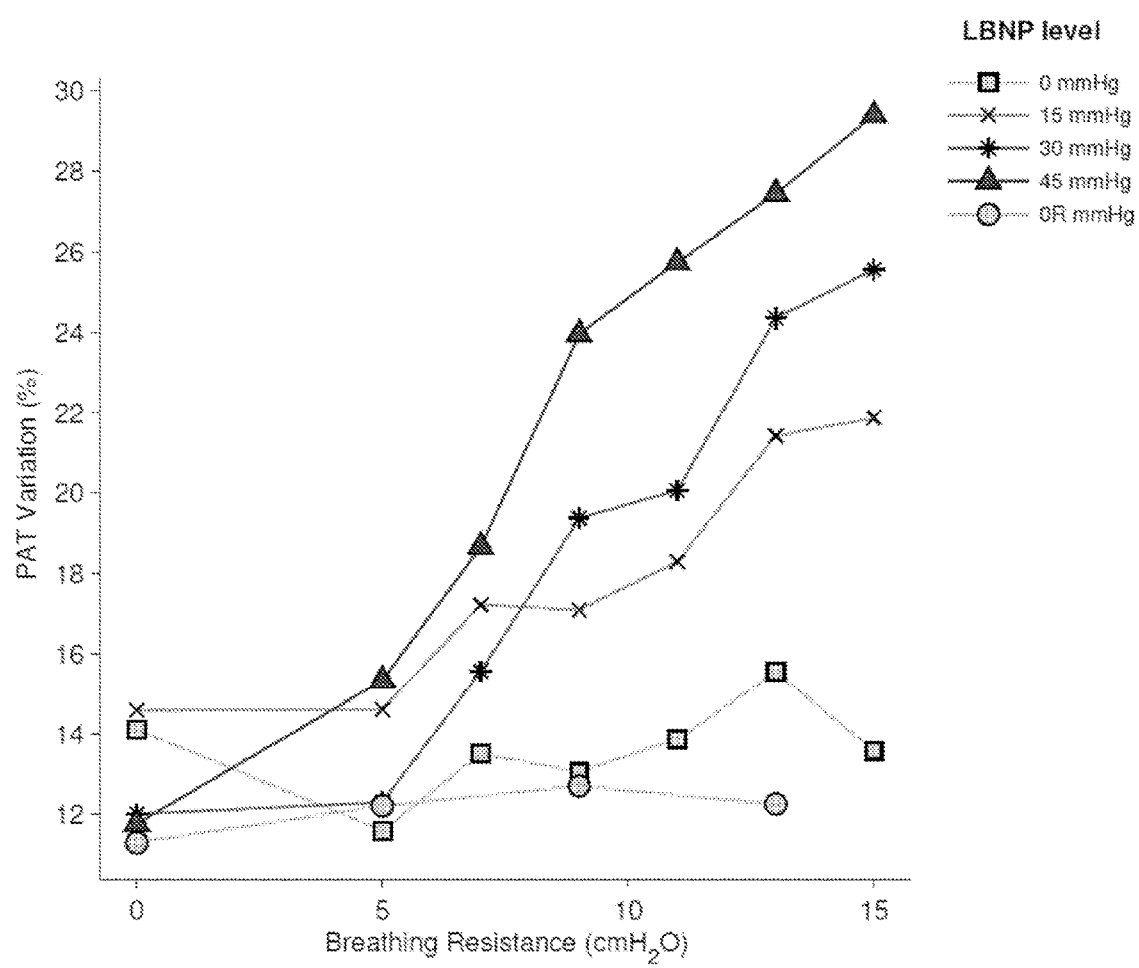
FIG. 60 is a schematic representation of the results obtained using the invention.

FIG. 60 shows similar results to FIG. 59 by the results are generated a system having the capabilities associated with example embodiment #1. The measured parameter is PAT variation. The results show excellent correspondence with the reference stroke volume. The combination of the inventive instrumentation and the variable resistance breathing protocol provides a multi-parameter assessment tool for accessing hemodynamic status.

The resulting data can be processed in many ways and the following is provided as an example. Because individuals differ in their breathing approach, chest versus diaphragmatic, the variance in stroke volume can be compared to the initial baseline data. For example, a slope can be calculated relating the percentage variance change in stroke volume to the change in exhale pressure as shown in FIG. 59. In terms of implementation, the test can be stopped when the % change has hit 20%. The pressure needed to obtain such a change is related to the hemodynamic status of the subject.

Ambulatory Patient with Heart Failure. The objective in managing this type of patient is to pick up hemodynamic congestion at the earliest point of occurrence so treatment can be initiated. In this use scenario, example embodiment 2 is used. The system is held by the patient with the arms located on the chest while in a supine position. The patient with heart failure does a minute or two of monitoring with no particular manipulation. As described elsewhere herein, the pulse measurements are sensitive to changes hydrostatic pressure and blood volume distribution. For illustration, consider if the patient failed to place the arm on the chest but instead kept the hands on the bed. The measurements would be impacted due to a change in hydrostatic position relative to prior measurements. The system has the ability to access position and specifically to determine the sensor position relative to the heart to ensure consistency of the measurement. Additionally, the sensors in embodiment 2 can access body pose. For illustration, if the bed is elevated relative to prior tests, the body pose would be different so a direct comparison of results is not possible. The system has the capabilities to ensure correct PPG senor position and body pose as well as ensure that quality signals are being measured. The system then determines one or more of the following LVET, PEP, PEP/LVET, and PAT, and compares this with prior values. If the measured values are within an acceptable tolerance of optimal values for this patient (as determined by care provider or via other methods), no further testing is required. However, if there are concerns regarding the development of possible congestion the patient is instructed to perform a subsequent test. For example, an equilibration period followed by a measurement period of 1 minute is initiated. Following the 1 minute period, the patient is requested to move to a sitting position. The compliance with the transition and the timing of the transition is assessed by the body pose determination system. The external or attached system will access the body pose and ensure acceptable compliance. Assuming correct body pose, a second measurement period is initiated for 1 minute. Following the second measurement period, the patient is instructed to stand. Again the body pose and sensor position system ensure that the body and sensors are in the correct position followed by data acquisition.

The resulting data can be processed as described in connection with FIG. 35 and FIG. 36. A normal response for the subject at an optimal hydration status can be stored in the watch. Variances relative to the baseline as well as changes consistent with fluid overload can be identified. The resulting test information can be communicated to a care provider team to assure patient compliance with testing and to address any changes in hemodynamic congestion.

The system proves the ability to measure one or more physiological processes over time and to compare these physiological signals or values with previously recorded values or with predetermined thresholds. For the purpose of heart failure, monitoring day-to-day trend information in parameters such as LVET, PEP, PEP/LVET, or PAT can be valuable for accessing hemodynamic congestion.

Hemodialysis Patient. The dialysis patient represents a different situation because the patient can be monitored over the course of the dialysis treatment and the patient effectively starts in a fluid overloaded condition. The care objective is to prevent the subject from suffering a hypotensive event. The system as shown in example embodiment #1 can be used for this purpose. Upon initiation of dialysis treatment, the subject is requested to breath at a rate of 6 breaths per minute. In one possible system, the phonocardiogram (PCG) can be used to detect heart sounds so compliance with the breathing protocol can be confirmed. The baseline measurement defines a starting set of cardiac performance measures that can be assessed over the treatment period. On a periodic basis, re-measurements can be initiated and trends defined. If the hemodynamic assessment shows variances or trends consistent with significant hypovolemia and pending hypotension, the rate of fluid removal can be decreased or stopped until the patient becomes more hemodynamically stable. The system effectively serves as an early warning system for hypotensive events.

Post-surgical monitoring. The current practice of medicine trends toward discharging more patients home post-surgery. This can reduce costs, but a patient at home is more difficult to monitor for post-surgical bleeding. The present invention can be used to assess cardiovascular function during one or more breathing test or during one or more changes in body position tests. An unexpected hemorrhage can result in hemodynamic changes that can be detected by the present invention. The patient's compliance with post-surgical care, for example drinking enough fluids, can also be reflected in hemodynamic changes that can be detected by the present invention.

Those skilled in the art will recognize that the present invention can be manifested in a variety of forms other than the specific embodiments described and contemplated herein. Accordingly, departures in form and detail can be made without departing from the scope and spirit of the present invention as described in the appended claims.

We claim:

1. A method of determining the volume status of a patient comprising: (a) causing a patient to perform a breathing protocol comprising causing the patient to breathe through a resistance breathing device having one or more flow-independent pressure valves, where the resistance breathing device allows inhalation airflow after the inhalation pressure exceeds a predetermined first inhale pressure threshold, and where the resistance breathing device allows exhalation airflow after the exhalation pressure-exceeds a predetermined first exhale pressure threshold;
(b) while the patient is performing the breathing protocol, noninvasively determining one or more time intervals within the patient's cardiac cycle over a first plurality of heartbeats of the patient, where each time interval corresponds to the time between predetermined events in the systolic phase of the patient's cardiac cycle;
(c) determining a first variance of the time intervals over the first plurality of heartbeats;
(d) determining the intravascular volume status of the patient from the first variance.

2. A method as in claim 1, wherein step (a) comprises causing the patient to inhale and exhale according to a paced breathing protocol.

3. A method as in claim 1, wherein the one or more time intervals is one or more of PAT, PEP, LVET, PTT, EMAT, and ICT.

4. A method as in claim 1, wherein step (c) comprises determining a variance of the time intervals within a specific respiratory phase.

5. A method as in claim 1, further comprising repeating steps (a), (b), and (c) with a second inhale pressure threshold, distinct from the first inhale pressure threshold, and a second exhale pressure threshold, distinct from the first exhale pressure threshold, and determining a second variance of the time intervals over a second plurality of heartbeats while the patient performs the breathing protocol; and wherein step (d) comprises determining the volume status of the patient from the first variance and from the second variance.

6. A method as in claim 5, wherein the second inhale pressure threshold is greater than the first inhale pressure threshold; the second exhale pressure threshold is greater than the first exhale pressure threshold; or both.

7. A method as in claim 1, wherein steps (a), (b), and (c) are performed with the patient in a first body position, and further comprising repeating steps (a), (b), and (c) with the patient in a second body position distinct from the first body position; and determining a second variance of the time intervals over a second plurality of heartbeats while the patient performs the breathing protocol; and wherein step (d) comprises determining the volume status of the patient from the first variance and from the second variance.

8. A method as in claim 1, wherein the exhale pressure threshold is no less than 5 cm H2O.

9. A method as in claim 1, wherein the inhale pressure threshold is no less than 5 cm H2O.

10. A method as in claim 1, wherein the breathing protocol and resistance breathing device cause the patient to maintain a constant intrathoracic pressure during inhalation and exhalation after each pressure threshold has been satisfied.

11. A method as in claim 1, wherein the time intervals are determined from at least one of an electrocardiogram, photoplethysmogram, and phonocardiogram.

* * * * *